(12) United States Patent
Allen et al.

(10) Patent No.: US 7,608,759 B2
(45) Date of Patent: Oct. 27, 2009

(54) SCARECROW-LIKE STRESS-RELATED POLYPEPTIDES AND METHODS OF USE IN PLANTS

(75) Inventors: Damian Allen, Cary, NC (US); Lori V. Mills, Willow Springs, NC (US); Nocha van Thielen, Durham, NC (US); Oswaldo da Costa e Silva, Neustadt (DE)

(73) Assignee: BASF Plant Science GmbH (DE)

( * ) Notice: Subject to any disclaimer, the term of this patent is extended or adjusted under 35 U.S.C. 154(b) by 0 days.

(21) Appl. No.: 12/169,126

(22) Filed: Jul. 8, 2008

(65) Prior Publication Data

US 2009/0031446 A1    Jan. 29, 2009

Related U.S. Application Data

(62) Division of application No. 11/665,890, filed as application No. PCT/US2005/037478 on Oct. 19, 2005, now Pat. No. 7,423,196.

(60) Provisional application No. 60/620,601, filed on Oct. 20, 2004.

(51) Int. Cl.
*A01H 5/00* (2006.01)
*C12N 15/82* (2006.01)
*C12N 15/87* (2006.01)
*C12N 5/14* (2006.01)
*C12N 15/63* (2006.01)
*C07H 21/00* (2006.01)

(52) U.S. Cl. .................... 800/295; 435/320.1; 435/419; 435/468; 800/278; 800/306; 800/312; 800/314; 800/320; 800/320.1; 536/23.1; 536/23.6

(58) Field of Classification Search ....................... None
See application file for complete search history.

(56) References Cited

U.S. PATENT DOCUMENTS

2007/0039070 A1* 2/2007 Bloksberg et al. ........... 800/284

* cited by examiner

*Primary Examiner*—Vinod Kumar
(74) *Attorney, Agent, or Firm*—Patricia A. McDaniels

(57) ABSTRACT

A transgenic plant transformed with an SLSRP coding nucleic acid, wherein expression of the nucleic acid sequence in the plant results in increased growth under water-limited conditions and/or increased tolerance to an environmental stress as compared to a wild type variety of the plant. Also provided are agricultural products, including seeds, produced by the transgenic plants. Also provided are isolated SLSRPs, and isolated SLSRP coding nucleic acids, and vectors and host cells containing the latter.

18 Claims, 12 Drawing Sheets

```
                   151                                                                                            225
SEQ ID NO:8   (83) LTEF-----------------------------------------------------------QAYNQTNNNRNHVLSNLLLRSVKRRTSLYHESMDEP
SEQ ID NO:6   (78) ASDN-----------------------------------------------------------GQRMSAGWSSASYQSES-------SSHSDGSLEGPGK
SEQ ID NO:4   (62) QPEP--------------------------------------------------TSVLDLQASPGRSCSSSTSLSSGTDSPHSISTDSDNFSTT
SEQ ID NO:2  (136) QAQG-------------------------------------------------LRDYDRHASTERSLSDSLIQQSDDSLDFSDLGPLSVSNSES
SEQ ID NO:28 (128) PSSS-------------------------------------------S------ASSVDHPERLASDSPDGSCSGGAFSDYASTTTTSSDSHWS
SEQ ID NO:29 (102) PVDD-------------------------------------------S------DQPLTTTSLAQLVSSPGGS-------SYASSTTTSSDSQWS
SEQ ID NO:25 (130) PPPS-------------------------DQPSMYNNPS-----------PETPDSNIYVKSSSSN----------SINSVVTSGNWA
SEQ ID NO:26 (150) PYSGGSSVESPDGSSAANSCNSLSPCNCSSSSDGLGAVPQTPVLEFPTAAFSQTPQLYGDLIPTGGMVESGGAWP
SEQ ID NO:27  (56) PSSS-------------------------------------------------KETAINGDSQADYPDNGS-------SSYHEQACSGSEV
SEQ ID NO:30 (123) PPSP----------------------ER-----------------NLAFAERNSENLDRVVPGNYTGGDCIGFGNGGIKPLSSGFI
SEQ ID NO:31 (151) P                                                  S          AS      S         SS   S   SSS     FS 226                                                                                            300
SEQ ID NO:8  (123) VPEMQNQNLYSNQTQRFG------------------------------VPLLHQLRPQPMNLPNNGPVPMTGPNFGYRNSN
SEQ ID NO:6  (112) IEEADYYGRQHRHGEQLIG-----------------------------SVAYHNTPSSVERPMGYPAETAQAYQMPNYQQAV
SEQ ID NO:4  (106) VQQVEPVDIASWVDCMALP-----------------------------EFEDCDRHLEEVKSDIDFASTDDEGFELTSLD
SEQ ID NO:2  (181) RPSAQPGR-GLFEDDLSYICSAYGSRPSASEYELSAEVEQEKTPLFEYLTDIEMDENVEKKCMFIEMSAYQAMA
SEQ ID NO:28 (174) VDGIENR--PSWLHTPMPSNFVFQSTSRS-NSVLGGGGGNSAVYGSSGFGDDLVSNMFKDDELAMQLKKGVEEAS
SEQ ID NO:29 (143) LDCIENNRPSSWLQTPIPSNFIFQSTS------TRASSG--NAVFGSSFSGDEMSNMFNDTDLANQLKKGMEEAS
SEQ ID NO:25 (172) EGAIELPQNYLIPVDYSS---QSSFGSTN-----SVHNAIEGLGEPT--MTNIEARDQFSESMLAEQFMRGVEEAR
SEQ ID NO:26 (225) YDPTEFYQLQHKPVRENLPSQSSSFASSNGSSVHFSEGFESLLSPAGVLPDVSENDFVVQNQQAYQERRGHQEAS
SEQ ID NO:27  (91) SDLLGSQDAHSITTDWSS---------------------N-----------------EFDRLAMQFRRGVEEAK
SEQ ID NO:30 (170) LDFRNPQSCSSILSVPQS--------------------------GLITIYGDGIDESSKNNRENHQSVWLERELEAN
SEQ ID NO:31 (226) VD LE    S                         T                        D  LL         ALQFRRGVEEAA
```

FIGURE 3-1C

```
                     301                                                                                    375
SEQ ID NO:8  (174)   LGLPQNQNR---------------------------------------VRVSLPVSVPVQVHS-----------SEPEKKIMDHRLLELEKQLLEDND
SEQ ID NO:6  (165)   RYIPEEQ-----------------------------------------YAQSQSNYAQRNP-----------EMAHMLQVLESALLDDDGADLPGSL
SEQ ID NO:4  (159)   HCSVVTEHG---------------------------------------YSVSLLSEFLGDP-----------DENLELPESFHDAKRLQEIMDDSLSS
SEQ ID NO:2  (255)   KELGDLISYDPPMP----------------IPETRRSDPHFEEDVRFVDSWIDEILSGPLPADRTDSPGAEAKLDI
SEQ ID NO:28 (246)   KFIMPKSSQLFIDVDSYIPMNSGSKENGSEMFVKTEKKDETEHHHHHSYAPPPNRETGKKKSHWRDEDEDFVEERSN
SEQ ID NO:29 (210)   KFLEKSS-----------------------------------Q-----IVIDNS----------------VP-NRETGKKKSHWREE-EHITEERSK
SEQ ID NO:25 (238)   KFELPKEDKLVINLE--------DNGISLPPKLMYDNGLNEVKEEE------KEYTAYGSRGRKNRHSDELDEDEGRSN
SEQ ID NO:26 (300)   KFELPDESKLVIDVDKLYSGDEGSRFLGEVRQEKKLVKVKTET-----SDVESAGHRGKKHFYGDDLDAEEGRCS
SEQ ID NO:27 (126)   RFIPNIEKLVDDPE---------------K-------NGLYACKQTETTEQR-----GKHENKERNHPDPHVEHIEMEARNS
SEQ ID NO:30 (224)   RENEENE---------------------------------------EIVNFR------------EENCVSKARKNSSRDEICMEEERSS
SEQ ID NO:31 (301)   KFLP                                              L                        EN LS  K H    DD DLEE RS 376                                                                                    450
SEQ ID NO:8  (222)   DEGEADAASVITTSEWSETYQNLISPSP---------------VQKPVLTTTSPLSSTTSSTS-------------SSSSV
SEQ ID NO:6  (211)   GNGHDPASEGNWADTEEFMAADASPAD-----------SSTVLSATTPPEYGKQCRNGSTNNYTGAATARVEEPPPQKL
SEQ ID NO:4  (206)   MLSEVRSSGDSGSSVPTTVEEARLVES-----------LPCSDLRRHGGVDTKHHHHHSRSESWGSTSKLQTLQH
SEQ ID NO:2  (316)   KHGSSPEELYSHTDADRGSSWNDTASDTASYLHPDSTLSPVDFGNSHALENGSGGSLQVGTRHLSSISSSNGNG
SEQ ID NO:28 (321)   KQSAVYVEE-SELSEMFDKILRVCGPGK----------PVCHLNQNFPTESAKVVTAQSNGAKIRGKKSTSTSHSNDS
SEQ ID NO:29 (248)   KQSAIYVDETDELIDMFDNILTFGEAKE---------QPVCILNESFPKEPAKASTFSKS------PKGEKPEASGNSY
SEQ ID NO:25 (302)   KQSAVDYTEETLRSEMSDLVRDCPNCDG----------KEGVSSKTWTQNEATRSPQNG-----HTRGSGSSKSRGKKPS
SEQ ID NO:26 (369)   KHSAQGIDTDHLVRDEMDKVIECNGETC----------SKGVKELREALQHDVAKHSGGG----HGKGSSHGKGRGKQP
SEQ ID NO:27 (184)   K-HMAISTSETIRDEMFDSHLECNRQLP----------GEVANLRGMMAKEASDNPKKFQS---KGYGKGQRKPHSSKKK
SEQ ID NO:30 (263)   K-LPAVFGEDILRSDVVDKELVHVPGGESMKEFNALRDVLKKGVEKKKASDAQGKRRARGRGRGRGRGGGGQN
SEQ ID NO:31 (376)   K SA    E    SEM D ILL              I                       A            G  G  G
```

```
                      901                                                                           975
SEQ ID NO:8  (652) -------------------------------------------------------------------------------
SEQ ID NO:6  (658) -------------------------------------------------------------------------------
SEQ ID NO:4  (644) -------------------------------------------------------------------------------
SEQ ID NO:2  (775) -------------------------------------------------------------------------------
SEQ ID NO:28 (818) GYDVSFLPTSIPDLGFGVPSSSDFDLRMDQYYHQPSIWVPDQDHHFSPPADEIDSENTLLKYVNQLLMEESLAE-
SEQ ID NO:29 (717) GFEY-----------------------------------------FDG------NPNLLTDPMEDQYPPPS------DTLLKYVSEILMEESNGDY
SEQ ID NO:25 (749) -------------------------------------------------------------------------------
SEQ ID NO:26 (819) -------------------------------------------------------------------------------
SEQ ID NO:27 (630) -------------------------------------------------------------------------------
SEQ ID NO:30 (719) -------------------------------------------------------------------------------
SEQ ID NO:31 (901) -------------------------------------------------------------------------------

976                                                                          1050
SEQ ID NO:8  (652) -------------------------------------------------------------------------------
SEQ ID NO:6  (658) -------------------------------------------------------------------------------
SEQ ID NO:4  (644) -------------------------------------------------------------------------------
SEQ ID NO:2  (775) -------------------------------------------------------------------------------
SEQ ID NO:28 (892) KQSIFYDSLALRQTEEMLQQVISDSQTQSSIPNNSITTSSSSNSGDYSNSSVRIENEVLFDNKHLGDSGVVS
SEQ ID NO:29 (760) KQSMFYDSLALRKTEEMLQQVITDSQNQSFSPADSLITNSWDASGSIDESAYS------
SEQ ID NO:25 (749) -------------------------------------------------------------------------------
SEQ ID NO:26 (819) -------------------------------------------------------------------------------
SEQ ID NO:27 (630) -------------------------------------------------------------------------------
SEQ ID NO:30 (719) -------------------------------------------------------------------------------
SEQ ID NO:31 (976) -------------------------------------------------------------------------------
```

FIGURE 3-3B

```
                       1051                                                              1125
SEQ ID NO:8    (652) ------------------------------------------------------------------
SEQ ID NO:6    (658) ------------------------------------------------------------------
SEQ ID NO:4    (644) ------------------------------------------------------------------
SEQ ID NO:2    (775) ------------------------------------------------------------------
SEQ ID NO:28   (967) FPGSNMLRGGEQFGQPANEILVRSMFSDAESVLQFKRGLEEASKFLPNTDQWIFNLEPEMERVVPVKVEEGWSAI
SEQ ID NO:29   (813) ------ADPQPVNEIMVKSMFSDAESALQFKKGVEEASKFLPNSDQWVINLDIERSERRDSVKEEMGLDQ
SEQ ID NO:25   (749) ------------------------------------------------------------------
SEQ ID NO:26   (819) ------------------------------------------------------------------
SEQ ID NO:27   (630) ------------------------------------------------------------------
SEQ ID NO:30   (719) ------------------------------------------------------------------
SEQ ID NO:31  (1051) ------------------------------------------------------------------

1126                                                              1200
SEQ ID NO:8    (652) ------------------------------------------------------------------
SEQ ID NO:6    (658) ------------------------------------------------------------------
SEQ ID NO:4    (644) ------------------------------------------------------------------
SEQ ID NO:2    (775) ------------------------------------------------------------------
SEQ ID NO:28  (1042) SKTRKNHHEREEEEDDLEEARRRSKQFAVNEEDGKLTEMFDKVLLLDGECDPQIIEDGENGSSKALVKKG---
SEQ ID NO:29  (877)  LRVKKNHER------DFEEVRS-SKQFASNVEDSKVTDMFDKVLLLDGECDPQTLLDSEIQAIRSSKNIGEKGKK
SEQ ID NO:25  (749) ------------------------------------------------------------------
SEQ ID NO:26  (819) ------------------------------------------------------------------
SEQ ID NO:27  (630) ------------------------------------------------------------------
SEQ ID NO:30  (719) ------------------------------------------------------------------
SEQ ID NO:31 (1126) ------------------------------------------------------------------
```

FIGURE 3-3C

```
                          1201                                                                      1275
SEQ ID NO:8     (652)   ------------------------------------------------------------------------------
SEQ ID NO:6     (658)   ------------------------------------------------------------------------------
SEQ ID NO:4     (644)   ------------------------------------------------------------------------------
SEQ ID NO:2     (775)   ------------------------------------------------------------------------------
SEQ ID NO:28  (1112)   RAKKKSRAVDFRTLLTLCAQSVSAGDKITADDLLRQIRKQCSPVGDASQRLAHFFANALEARLEGSTGTMIQSYY
SEQ ID NO:29   (945)   KKKKKSQVVDFRTLLTHCAQAISTGDKTTALEFLLQIRQQSPLGDAGQRLAHCFANALEARLQGSTGPMIQTYY
SEQ ID NO:25   (749)   ------------------------------------------------------------------------------
SEQ ID NO:26   (819)   ------------------------------------------------------------------------------
SEQ ID NO:27   (630)   ------------------------------------------------------------------------------
SEQ ID NO:30   (719)   ------------------------------------------------------------------------------
SEQ ID NO:31 (1201)   ------------------------------------------------------------------------------

1276                                                                      1350
SEQ ID NO:8     (652)   ------------------------------------------------------------------------------
SEQ ID NO:6     (658)   ------------------------------------------------------------------------------
SEQ ID NO:4     (644)   ------------------------------------------------------------------------------
SEQ ID NO:2     (775)   ------------------------------------------------------------------------------
SEQ ID NO:28  (1187)   DSISS-KKRTAAQILKSYSVFLSASPFMTLIYFFSNKMILDAAKDASVLHIVDFGILYGFQWPMFIQHLSKSNPG
SEQ ID NO:29  (1020)   NALTSSLKDTAADTIRAYRVYLSSSPFVTLMYFFSIWMILDVAKDAPVLHIVDFGILYGFQWPMFIQSISDRKDV
SEQ ID NO:25   (749)   ------------------------------------------------------------------------------
SEQ ID NO:26   (819)   ------------------------------------------------------------------------------
SEQ ID NO:27   (630)   ------------------------------------------------------------------------------
SEQ ID NO:30   (719)   ------------------------------------------------------------------------------
SEQ ID NO:31 (1276)   ------------------------------------------------------------------------------
```

FIGURE 3-4A

```
                          1351                                                                          1425
SEQ ID NO:8    (652)  ------------------------------------------------------------------------
SEQ ID NO:6    (658)  ------------------------------------------------------------------------
SEQ ID NO:4    (644)  ------------------------------------------------------------------------
SEQ ID NO:2    (775)  ------------------------------------------------------------------------
SEQ ID NO:28 (1261)  LRKLRITGIEIPQHGLRPTERIQDTGRRLTEYCKRFGVPFEYNAIASKNWETIKMEEFKIRPNEVLAVNAVLRFK
SEQ ID NO:29 (1095)  PRKLRITGIELPQCGFRPAERIEETGRRLAEYCKRFNVPFEYKAIASQNWETIRIEDLDIRPNEVLAVNAGLRLK
SEQ ID NO:25  (749)  ------------------------------------------------------------------------
SEQ ID NO:26  (819)  ------------------------------------------------------------------------
SEQ ID NO:27  (630)  ------------------------------------------------------------------------
SEQ ID NO:30  (719)  ------------------------------------------------------------------------
SEQ ID NO:31 (1351)  ------------------------------------------------------------------------

1426                                                                          1500
SEQ ID NO:8    (652)  ------------------------------------------------------------------------
SEQ ID NO:6    (658)  ------------------------------------------------------------------------
SEQ ID NO:4    (644)  ------------------------------------------------------------------------
SEQ ID NO:2    (775)  ------------------------------------------------------------------------
SEQ ID NO:28 (1336)  NLRDVIPGEEDCPRDGFLKLIRDMNPNVFLSSTVNGSFNAPFFTTRFKEALFHYSALFDLFGATLSKENPERIHF
SEQ ID NO:29 (1170)  NLQDETGSEENCPRDAVLKLIRNMNPDVFIHAIVNGSFNAPFFISRFKEAVYHYSALFDMFDSTLPRDNKERIRF
SEQ ID NO:25  (749)  ------------------------------------------------------------------------
SEQ ID NO:26  (819)  ------------------------------------------------------------------------
SEQ ID NO:27  (630)  ------------------------------------------------------------------------
SEQ ID NO:30  (719)  ------------------------------------------------------------------------
SEQ ID NO:31 (1426)  ------------------------------------------------------------------------
```

FIGURE 3-4B

```
                     1501                                                                        1575
SEQ ID NO:8   (652)  ---------------------------------------------------------------------------
SEQ ID NO:6   (658)  ---------------------------------------------------------------------------
SEQ ID NO:4   (644)  ---------------------------------------------------------------------------
SEQ ID NO:2   (775)  ---------------------------------------------------------------------------
SEQ ID NO:28 (1411)  EGEFYGREVMNVIACEGVDRVERPETYKQWQVRMIRAGFKQKPVEAELVQLFREKMKKWGYHKDFVLDEDSNWFL
SEQ ID NO:29 (1245)  EREFYGREAMNVIACEEADRVERPETYRQWQVRMVRAGFKQKPVEAELVQLFREKMKKWGYHKDFVLDEDSNWFL
SEQ ID NO:25 (749)   ---------------------------------------------------------------------------
SEQ ID NO:26 (819)   ---------------------------------------------------------------------------
SEQ ID NO:27 (630)   ---------------------------------------------------------------------------
SEQ ID NO:30 (719)   ---------------------------------------------------------------------------
SEQ ID NO:31 (1501)  ---------------------------------------------------------------------------

1576            1592
SEQ ID NO:8   (652)  -----------------
SEQ ID NO:6   (658)  -----------------
SEQ ID NO:4   (644)  -----------------
SEQ ID NO:2   (775)  -----------------
SEQ ID NO:28 (1486)  QGWKGRILFSSSCWVPS
SEQ ID NO:29 (1320)  QGWKGRTLYASSCWVPA
SEQ ID NO:25 (749)   -----------------
SEQ ID NO:26 (819)   -----------------
SEQ ID NO:27 (630)   -----------------
SEQ ID NO:30 (719)   -----------------
SEQ ID NO:31 (1576)  -----------------
```

ID

SEQUENCE LISTING

```
<160> NUMBER OF SEQ ID NOS: 24

<210> SEQ ID NO 1
<211> LENGTH: 2685
<212> TYPE: DNA
<213> ORGANISM: Physcomitrella patens
<220> FEATURE:
<221> NAME/KEY: CDS
<222> LOCATION: (152)..(2476)
<223> OTHER INFORMATION: Scarecrow-like gene PpSCL1 (EST 386)

<400> SEQUENCE: 1
atcccgggag acaagctaag caagtaagca agagctgaat tagggaaaag aagaccataa        60
gctcaatgca agagcgtacc tttatttgta agcacaggga aacgctaaag gtcgagtata       120
ttccgaaccc tttcacgtgg taattacggc a atg gct gga agt aag cat gag         172
                                  Met Ala Gly Ser Lys His Glu
                                  1               5 aga tcg ggg gat tcc cct gta gga aca gga gag gtg tct cca ctt gct         220
Arg Ser Gly Asp Ser Pro Val Gly Thr Gly Glu Val Ser Pro Leu Ala
 10              15                  20 gca caa ctt cag caa gca tgg ctt caa acg cag atg ccc aaa gct cag         268
Ala Gln Leu Gln Gln Ala Trp Leu Gln Thr Gln Met Pro Lys Ala Gln
25                  30                  35 aag cgg agt ttt acc tcg gtt gca aat gcg cag aac caa ctt cct cgg         316
Lys Arg Ser Phe Thr Ser Val Ala Asn Ala Gln Asn Gln Leu Pro Arg
40                  45                  50                  55 ttg tca ccg cca ggt cct ggg tct gag atg tcc gca tcc tcg aaa cca         364
Leu Ser Pro Pro Gly Pro Gly Ser Glu Met Ser Ala Ser Ser Lys Pro
60                  65                  70 cca tca tcc tct gta ctg aag tcc ttg tcg act ctt ttt ccc gag ctt         412
Pro Ser Ser Ser Val Leu Lys Ser Leu Ser Thr Leu Phe Pro Glu Leu
75                  80                  85 gca aac gtt caa gag aag aag gag gca aag atc tct tct gtt ttt gaa         460
Ala Asn Val Gln Glu Lys Lys Glu Ala Lys Ile Ser Ser Val Phe Glu
90                  95                 100 gaa gga gag caa cca att cca att cac cca gaa tta cgc cag aag aaa         508
Glu Gly Glu Gln Pro Ile Pro Ile His Pro Glu Leu Arg Gln Lys Lys
105                 110                 115 gct gaa tgc tta gag gtg atg ttt ggt caa gac gtt gtt gag cag acg         556
Ala Glu Cys Leu Glu Val Met Phe Gly Gln Asp Val Val Glu Gln Thr
120                 125                 130                 135 caa gct cag ggg ctc agg gac tac gac cgt cat gca tct aca gaa cgg         604
Gln Ala Gln Gly Leu Arg Asp Tyr Asp Arg His Ala Ser Thr Glu Arg
140                 145                 150 tca ttg tct gat agt ctg att cag caa tct gac gac tcg ttg gat ttc         652
Ser Leu Ser Asp Ser Leu Ile Gln Gln Ser Asp Asp Ser Leu Asp Phe
155                 160                 165 tct gac ctt ggg ccg ctt tct gtt tcc aat agt ttc tcg aga cct agt         700
Ser Asp Leu Gly Pro Leu Ser Val Ser Asn Ser Phe Ser Arg Pro Ser
170                 175                 180 gca cag cct gga cga gga act ttt gag gac gat ctt tcc tac atc tgt         748
Ala Gln Pro Gly Arg Gly Thr Phe Glu Asp Asp Leu Ser Tyr Ile Cys
185                 190                 195
```

| | | |
|---|---|---|
| agc gct tac ggt agt aga cct tcg gca tca gaa tat gag act tcg gcg<br>Ser Ala Tyr Gly Ser Arg Pro Ser Ala Ser Glu Tyr Glu Thr Ser Ala<br>200                   205                 210                215 | | 796 |
| gag gtg gaa caa gag aaa acg cca ctg ttt gaa tat ctt aca gac ata<br>Glu Val Glu Gln Glu Lys Thr Pro Leu Phe Glu Tyr Leu Thr Asp Ile<br>220                   225                 230 | | 844 |
| ctc atg gat gaa aac gta gag gaa aag aaa tgc atg ttc att gaa atg<br>Leu Met Asp Glu Asn Val Glu Glu Lys Lys Cys Met Phe Ile Glu Met<br>235                   240                 245 | | 892 |
| agc gct tat cag gcc atg gcg aaa gaa ctt gga gac ctt atc tca tac<br>Ser Ala Tyr Gln Ala Met Ala Lys Glu Leu Gly Asp Leu Ile Ser Tyr<br>250                   255                 260 | | 940 |
| gat cct cct cct atg cca ata cct gaa act aga aga tcg gat cct cac<br>Asp Pro Pro Pro Met Pro Ile Pro Glu Thr Arg Arg Ser Asp Pro His<br>265                   270                 275 | | 988 |
| ttt gaa gaa gat gtc aga ttc gtc gac agc tgg att gat gag att cta<br>Phe Glu Glu Asp Val Arg Phe Val Asp Ser Trp Ile Asp Glu Ile Leu<br>280                   285                 290                295 | | 1036 |
| agt ggt cct ctt cct gcg gat cgt acg gat agc cct ggt gca gaa gct<br>Ser Gly Pro Leu Pro Ala Asp Arg Thr Asp Ser Pro Gly Ala Glu Ala<br>300                   305                 310 | | 1084 |
| aag ctt gac atc aaa cac gga agc agt cct gaa gaa ctc tac tct cac<br>Lys Leu Asp Ile Lys His Gly Ser Ser Pro Glu Glu Leu Tyr Ser His<br>315                   320                 325 | | 1132 |
| aca gac gca gat cgt ggc agc tct gtc tgg aat gat acg gcg tct gat<br>Thr Asp Ala Asp Arg Gly Ser Ser Val Trp Asn Asp Thr Ala Ser Asp<br>330                   335                 340 | | 1180 |
| aca gca tca tac cta cat cca gac tcc acc tta tct ccc gtg gac ttt<br>Thr Ala Ser Tyr Leu His Pro Asp Ser Thr Leu Ser Pro Val Asp Phe<br>345                   350                 355 | | 1228 |
| ggg aac tcc cat gct ctt gaa aat ggt agt gga ggc agt tta caa gtt<br>Gly Asn Ser His Ala Leu Glu Asn Gly Ser Gly Gly Ser Leu Gln Val<br>360                   365                 370                375 | | 1276 |
| ggt act cgt cac cta agt agc ata tct tcg tca aat ggc aat ggg gtt<br>Gly Thr Arg His Leu Ser Ser Ile Ser Ser Ser Asn Gly Asn Gly Val<br>380                   385                 390 | | 1324 |
| cat gca ccg ccg gtg gac ttg act gat ctc ctc atc aga tgc gcg caa<br>His Ala Pro Pro Val Asp Leu Thr Asp Leu Leu Ile Arg Cys Ala Gln<br>395                   400                 405 | | 1372 |
| gca gtg gaa caa gcg gac tat cgg cat gcc aat gag ttg att cac gaa<br>Ala Val Glu Gln Ala Asp Tyr Arg His Ala Asn Glu Leu Ile His Glu<br>410                   415                 420 | | 1420 |
| ctg cgt cat cac tcg tcc gcg tat gga aat ggg tcc cag cgc atg gcc<br>Leu Arg His His Ser Ser Ala Tyr Gly Asn Gly Ser Gln Arg Met Ala<br>425                   430                 435 | | 1468 |
| cat tac ttc atg gaa gct ctg gtt gct aaa ata tct gga act ggc gga<br>His Tyr Phe Met Glu Ala Leu Val Ala Lys Ile Ser Gly Thr Gly Gly<br>440                   445                 450                455 | | 1516 |
| cag ctt tac tca gct cta tcc aac tac cgt cct tcc gag gcc caa atg<br>Gln Leu Tyr Ser Ala Leu Ser Asn Tyr Arg Pro Ser Glu Ala Gln Met<br>460                   465                 470 | | 1564 |
| ctg agg gcg caa atg ttg ttc tgc gag cat tgt cct ttc att caa gtg<br>Leu Arg Ala Gln Met Leu Phe Cys Glu His Cys Pro Phe Ile Gln Val<br>475                   480                 485 | | 1612 |
| cca cat att tat gct aat cat gca att atg gtg gcc ttc aag ggt gcc<br>Pro His Ile Tyr Ala Asn His Ala Ile Met Val Ala Phe Lys Gly Ala<br>490                   495                 500 | | 1660 |
| cca cga gtt cat att att gac tac ggc atc ctt tat gga att cag tgg<br>Pro Arg Val His Ile Ile Asp Tyr Gly Ile Leu Tyr Gly Ile Gln Trp<br>505                   510                 515 | | 1708 |

-continued

| | | |
|---|---|---|
| ctg tgc ctt att cat cag ctt tca caa cgt cct gag gga cca cca cac<br>Leu Cys Leu Ile His Gln Leu Ser Gln Arg Pro Glu Gly Pro Pro His<br>520                       525                    530                      535 | 1756 |
| ctt cgt att aca ggc atc gat agg cct caa cca gga ttc agg ccc tca<br>Leu Arg Ile Thr Gly Ile Asp Arg Pro Gln Pro Gly Phe Arg Pro Ser<br>540                       545                    550 | 1804 |
| gcg aga att caa gat act ggg cgg cgt ctg gct aag ctt gcg aag caa<br>Ala Arg Ile Gln Asp Thr Gly Arg Arg Leu Ala Lys Leu Ala Lys Gln<br>555                       560                    565 | 1852 |
| atg gga gtg ccg ttt gag ttt cat gca ata gct gag aaa tgg gag gca<br>Met Gly Val Pro Phe Glu Phe His Ala Ile Ala Glu Lys Trp Glu Ala<br>570                       575                    580 | 1900 |
| att acc cct gct cat ctc tta ctg cga gat gat gaa gtc ctc gca gtg<br>Ile Thr Pro Ala His Leu Leu Leu Arg Asp Asp Glu Val Leu Ala Val<br>585                       590                    595 | 1948 |
| aat tct atg ttc agg ttc cgt cat tta ttg gat gag tcc gtc aca gcc<br>Asn Ser Met Phe Arg Phe Arg His Leu Leu Asp Glu Ser Val Thr Ala<br>600                       605                    610                    615 | 1996 |
| gca agc cct cgc aat ctt gtg ctg agc aga ata aga agc ttg aat cca<br>Ala Ser Pro Arg Asn Leu Val Leu Ser Arg Ile Arg Ser Leu Asn Pro<br>620                       625                    630 | 2044 |
| aag atc ttc gtc caa gga gtc ctc aac gct ggc tac aac gca ccc ttt<br>Lys Ile Phe Val Gln Gly Val Leu Asn Ala Gly Tyr Asn Ala Pro Phe<br>635                       640                    645 | 2092 |
| ttt atg tcc cgc ttc cga gag gca ctg gct tac ttc tca aca ata ttc<br>Phe Met Ser Arg Phe Arg Glu Ala Leu Ala Tyr Phe Ser Thr Ile Phe<br>650                       655                    660 | 2140 |
| gac tct atg gag tgt tcg ttt cct gca gag cac ccg gac agg caa atc<br>Asp Ser Met Glu Cys Ser Phe Pro Ala Glu His Pro Asp Arg Gln Ile<br>665                       670                    675 | 2188 |
| ata gat cac gag att gta ggc aga gag att ttg aac gtg gtg gct tgt<br>Ile Asp His Glu Ile Val Gly Arg Glu Ile Leu Asn Val Val Ala Cys<br>680                       685                    690                    695 | 2236 |
| gaa ggc ccg gag agg gtg gag cgc tcg gaa acg tac aga cag tgg cag<br>Glu Gly Pro Glu Arg Val Glu Arg Ser Glu Thr Tyr Arg Gln Trp Gln<br>700                       705                    710 | 2284 |
| gca cgg acc atg cga gct ggc ttc cag cag aag ccc aac tct ccg aac<br>Ala Arg Thr Met Arg Ala Gly Phe Gln Gln Lys Pro Asn Ser Pro Asn<br>715                       720                    725 | 2332 |
| gtc atg gct aag att agg atg gca atg agg tca tat cac aga gac tac<br>Val Met Ala Lys Ile Arg Met Ala Met Arg Ser Tyr His Arg Asp Tyr<br>730                       735                    740 | 2380 |
| ggt att ggg gaa gac ggt gcc tgg ttc ttg ctc gga tgg aag gag cgc<br>Gly Ile Gly Glu Asp Gly Ala Trp Phe Leu Leu Gly Trp Lys Glu Arg<br>745                       750                    755 | 2428 |
| atc aca cat gcc atg act gtc tgg gag cct ctc ccc gac agc cct tga<br>Ile Thr His Ala Met Thr Val Trp Glu Pro Leu Pro Asp Ser Pro<br>760                       765                    770 | 2476 |
| ttgtcgccac atatttcctt gtggtcactt ctctgcacta ggaagtaatc acagtaccat | 2536 |
| gttccttctc attgggcaag tagagtgata attgtgttgt gattagatag atggccctga | 2596 |
| acaacgcctt atctcattaa tcttgagcaa tgccttacaa actgctgtgc tcaccttcgc | 2656 |
| ctgcagctct gtactatatc cgagctcgc | 2685 |

<210> SEQ ID NO 2
<211> LENGTH: 774
<212> TYPE: PRT
<213> ORGANISM: Physcomitrella patens

<400> SEQUENCE: 2

```
Met Ala Gly Ser Lys His Glu Arg Ser Gly Asp Ser Pro Val Gly Thr
 1               5                  10                  15
Gly Glu Val Ser Pro Leu Ala Ala Gln Leu Gln Gln Ala Trp Leu Gln
            20                  25                  30
Thr Gln Met Pro Lys Ala Gln Lys Arg Ser Phe Thr Ser Val Ala Asn
        35                  40                  45
Ala Gln Asn Gln Leu Pro Arg Leu Ser Pro Pro Gly Pro Gly Ser Glu
    50                  55                  60
Met Ser Ala Ser Ser Lys Pro Pro Ser Ser Val Leu Lys Ser Leu
65                  70                  75                  80
Ser Thr Leu Phe Pro Glu Leu Ala Asn Val Gln Glu Lys Lys Glu Ala
            85                  90                  95
Lys Ile Ser Ser Val Phe Glu Glu Gly Glu Gln Pro Ile Pro Ile His
100                 105                 110
Pro Glu Leu Arg Gln Lys Lys Ala Glu Cys Leu Glu Val Met Phe Gly
        115                 120                 125
Gln Asp Val Val Glu Gln Thr Gln Ala Gln Gly Leu Arg Asp Tyr Asp
    130                 135                 140
Arg His Ala Ser Thr Glu Arg Ser Leu Ser Asp Ser Leu Ile Gln Gln
145                 150                 155                 160
Ser Asp Asp Ser Leu Asp Phe Ser Asp Leu Gly Pro Leu Ser Val Ser
            165                 170                 175
Asn Ser Phe Ser Arg Pro Ser Ala Gln Pro Gly Arg Gly Thr Phe Glu
        180                 185                 190
Asp Asp Leu Ser Tyr Ile Cys Ser Ala Tyr Gly Ser Arg Pro Ser Ala
    195                 200                 205
Ser Glu Tyr Glu Thr Ser Ala Glu Val Glu Gln Lys Thr Pro Leu
210                 215                 220
Phe Glu Tyr Leu Thr Asp Ile Leu Met Asp Glu Asn Val Glu Glu Lys
            225                 230                 235                 240
Lys Cys Met Phe Ile Glu Met Ser Ala Tyr Gln Ala Met Ala Lys Glu
        245                 250                 255
Leu Gly Asp Leu Ile Ser Tyr Asp Pro Pro Met Pro Ile Pro Glu
    260                 265                 270
Thr Arg Arg Ser Asp Pro His Phe Glu Glu Asp Val Arg Phe Val Asp
275                 280                 285
Ser Trp Ile Asp Glu Ile Leu Ser Gly Pro Leu Pro Ala Asp Arg Thr
            290                 295                 300
Asp Ser Pro Gly Ala Glu Ala Lys Leu Asp Ile Lys His Gly Ser Ser
305                 310                 315                 320
Pro Glu Glu Leu Tyr Ser His Thr Asp Ala Asp Arg Gly Ser Ser Val
            325                 330                 335
Trp Asn Asp Thr Ala Ser Asp Thr Ala Ser Tyr Leu His Pro Asp Ser
        340                 345                 350
Thr Leu Ser Pro Val Asp Phe Gly Asn Ser His Ala Leu Glu Asn Gly
    355                 360                 365
Ser Gly Gly Ser Leu Gln Val Gly Thr Arg His Leu Ser Ser Ile Ser
370                 375                 380
Ser Ser Asn Gly Asn Gly Val His Ala Pro Pro Val Asp Leu Thr Asp
            385                 390                 395                 400
Leu Leu Ile Arg Cys Ala Gln Ala Val Glu Gln Ala Asp Tyr Arg His
        405                 410                 415
```

```
Ala Asn Glu Leu Ile His Glu Leu Arg His His Ser Ser Ala Tyr Gly
420                 425                 430

Asn Gly Ser Gln Arg Met Ala His Tyr Phe Met Glu Ala Leu Val Ala
435                 440                 445

Lys Ile Ser Gly Thr Gly Gln Leu Tyr Ser Ala Leu Ser Asn Tyr
    450                 455                 460

Arg Pro Ser Glu Ala Gln Met Leu Arg Ala Gln Met Leu Phe Cys Glu
465                 470                 475                 480

His Cys Pro Phe Ile Gln Val Pro His Ile Tyr Ala Asn His Ala Ile
    485                 490                 495

Met Val Ala Phe Lys Gly Ala Pro Arg Val His Ile Ile Asp Tyr Gly
500                 505                 510

Ile Leu Tyr Gly Ile Gln Trp Leu Cys Leu Ile His Gln Leu Ser Gln
515                 520                 525

Arg Pro Glu Gly Pro Pro His Leu Arg Ile Thr Gly Ile Asp Arg Pro
530                 535                 540

Gln Pro Gly Phe Arg Pro Ser Ala Arg Ile Gln Asp Thr Gly Arg Arg
545                 550                 555                 560

Leu Ala Lys Leu Ala Lys Gln Met Gly Val Pro Phe Glu Phe His Ala
565                 570                 575

Ile Ala Glu Lys Trp Glu Ala Ile Thr Pro Ala His Leu Leu Leu Arg
580                 585                 590

Asp Asp Glu Val Leu Ala Val Asn Ser Met Phe Arg Phe Arg His Leu
595                 600                 605

Leu Asp Glu Ser Val Thr Ala Ala Ser Pro Arg Asn Leu Val Leu Ser
610                 615                 620

Arg Ile Arg Ser Leu Asn Pro Lys Ile Phe Val Gln Gly Val Leu Asn
625                 630                 635                 640

Ala Gly Tyr Asn Ala Pro Phe Phe Met Ser Arg Phe Arg Glu Ala Leu
645                 650                 655

Ala Tyr Phe Ser Thr Ile Phe Asp Ser Met Glu Cys Ser Phe Pro Ala
660                 665                 670

Glu His Pro Asp Arg Gln Ile Ile Asp His Glu Ile Val Gly Arg Glu
675                 680                 685

Ile Leu Asn Val Val Ala Cys Glu Gly Pro Glu Arg Val Glu Arg Ser
690                 695                 700

Glu Thr Tyr Arg Gln Trp Gln Ala Arg Thr Met Arg Ala Gly Phe Gln
705                 710                 715                 720

Gln Lys Pro Asn Ser Pro Asn Val Met Ala Lys Ile Arg Met Ala Met
725                 730                 735

Arg Ser Tyr His Arg Asp Tyr Gly Ile Gly Glu Asp Gly Ala Trp Phe
740                 745                 750

Leu Leu Gly Trp Lys Glu Arg Ile Thr His Ala Met Thr Val Trp Glu
755                 760                 765

Pro Leu Pro Asp Ser Pro
770

<210> SEQ ID NO 3
<211> LENGTH: 2773
<212> TYPE: DNA
<213> ORGANISM: Physcomitrella patens
<220> FEATURE:
<221> NAME/KEY: CDS
<222> LOCATION: (569)..(2500)
<223> OTHER INFORMATION: Scarecrow-like gene PpSCL2 (EST 166)
```

<400> SEQUENCE: 3

```
gcgatatcgg cggtgatctc cgtttctggc tctcgcaaac ccctcttgtt gcacttcatt      60
gctttagaac caagtatctt aaatgctctc agaatttctc atcatgttca attgtagact     120
tatatgaggt gtcttttaga ctgcattctt tcagacgcag tgctagtgct gctttggtaa     180
tgaagggctt gcacgttgct tattttctgc tagagcttaa tctcgtctct ctgaaatttt     240
cttgatgctt cactagcgac tcgcggagtc catacgaggg gttcgtagct cttggacttg     300
cttaattgga cttttcgac gacggttgtg aaattagtct taagtgcag cttttggagg       360 gtctcatctg cgggctatct gccgcacgca acttagtgtt tacaaatcct gcttcccagt     420
tgatcattca cagctggact tggtaacagg gggaaaggat tttgaagttt gtttgagcac     480
atgtctgggt ttgtgaaaat ttacatttgg gaagctcgca actttgccat ttgaggaaga     540
tctctctgtc tgttcaatct ctgcaaca atg gct gcc act cac gtc gtt agc       592
                              Met Ala Ala Thr His Val Val Ser
                              1               5 aag aag agg tcg ccc act atc ttc tct gag gtc gcc aca gcc acc tgc      640
Lys Lys Arg Ser Pro Thr Ile Phe Ser Glu Val Ala Thr Ala Thr Cys
10              15                  20 aag cga tgg aaa tcc gaa gcg gcc tgg cac cac gtg gaa gaa atg gcc      688
Lys Arg Trp Lys Ser Glu Ala Ala Trp His His Val Glu Glu Met Ala
25              30                  35                  40 ccg gag cca cca ccc atc cag gac ttc gac ctc aag gtg aaa act tcg      736
Pro Glu Pro Pro Pro Ile Gln Asp Phe Asp Leu Lys Val Lys Thr Ser
    45              50                  55 tgc ttg aag atg gtg cag cca gaa ccc acg tcc gtg ctg gac ttg caa      784
Cys Leu Lys Met Val Gln Pro Glu Pro Thr Ser Val Leu Asp Leu Gln
60              65                  70 gcc agc cca ggt cgg tct tgt tcg tcg tcg acc agc ctg agc tcc ggg      832
Ala Ser Pro Gly Arg Ser Cys Ser Ser Ser Thr Ser Leu Ser Ser Gly
75              80                  85 acc gat tct ccc cac tcc atc tcc act gac tct cca aat ttc tcc acc      880
Thr Asp Ser Pro His Ser Ile Ser Thr Asp Ser Pro Asn Phe Ser Thr
90              95                  100 act gtg cag caa gtt gag ccg gtt gac atc gcc agc tgg gtc gac tgt      928
Thr Val Gln Gln Val Glu Pro Val Asp Ile Ala Ser Trp Val Asp Cys
105             110                 115                 120 atg gcc ctg ccc gaa ttt gaa gac tgc gac cgc cat ttg gag gaa gtt      976
Met Ala Leu Pro Glu Phe Glu Asp Cys Asp Arg His Leu Glu Glu Val
125             130                 135 ctt aag tcc gac atc gac ttc gcc agc aca gat ctg gac ttc ggc ttc     1024
Leu Lys Ser Asp Ile Asp Phe Ala Ser Thr Asp Leu Asp Phe Gly Phe
140             145                 150 gag ctt acg agc ttg gac cat tgt agc gtt gtg acc gag cat ggc tac     1072
Glu Leu Thr Ser Leu Asp His Cys Ser Val Val Thr Glu His Gly Tyr
155             160                 165 tct gtg agt ctc tta tcc gag ttt ctc ggg gat cct gat gag aat ctt     1120
Ser Val Ser Leu Leu Ser Glu Phe Leu Gly Asp Pro Asp Glu Asn Leu
170             175                 180 ctt ctt cca gag agc ttt cac gac gca aag agg ctg caa gag tta gac     1168
Leu Leu Pro Glu Ser Phe His Asp Ala Lys Arg Leu Gln Glu Leu Asp
185             190                 195                 200 gac tcg ctc tcg tca atg ttg agt gag gtt cga tcg agc ggt tca gac     1216
Asp Ser Leu Ser Ser Met Leu Ser Glu Val Arg Ser Ser Gly Ser Asp
205             210                 215 tcg ggg agt agc gta ccg aca aca gtc gag ctt gcg agg ctc gtc gaa     1264
Ser Gly Ser Ser Val Pro Thr Thr Val Glu Leu Ala Arg Leu Val Glu
```

```
                    220                 225                 230
tca ctg cct tgc tct gac ttg cga aga cac gga ggt gtt gac acg aaa    1312
Ser Leu Pro Cys Ser Asp Leu Arg Arg His Gly Gly Val Asp Thr Lys
235                 240                 245 cac cac cac cac cat agc cga tct gag agc tgg ggg tcg acg agc aaa    1360
His His His His Ser Arg Ser Glu Ser Trp Gly Ser Thr Ser Lys
250                 255                 260 ctg caa acc ttg cag cat ccg gag gac agc gga ttg cag ctg gtt cat    1408
Leu Gln Thr Leu Gln His Pro Glu Asp Ser Gly Leu Gln Leu Val His
265                 270                 275                 280 atg ttg tta gcg tgc gct gaa gcg att gaa aag tct gac ttc aac aaa    1456
Met Leu Leu Ala Cys Ala Glu Ala Ile Glu Lys Ser Asp Phe Asn Lys
285                 290                 295 gca aag cct atc tta gac cag tta ctc cga tcc tcc gac cca tat ggt    1504
Ala Lys Pro Ile Leu Asp Gln Leu Leu Arg Ser Ser Asp Pro Tyr Gly
300                 305                 310 gac ccc atg caa cga atc gcc ctt tac ttc ggt gaa gcc ctc act gat    1552
Asp Pro Met Gln Arg Ile Ala Leu Tyr Phe Gly Glu Ala Leu Thr Asp
315                 320                 325 cat ctt gcc ggg gtt gtc agc ccc agt gaa act cac ttg ctt tcg gat    1600
His Leu Ala Gly Val Val Ser Pro Ser Glu Thr His Leu Leu Ser Asp
330                 335                 340 tcc aag ctc gcg tac caa gcc ttc tac aaa gtg ctt cct ttc gcg aaa    1648
Ser Lys Leu Ala Tyr Gln Ala Phe Tyr Lys Val Leu Pro Phe Ala Lys
345                 350                 355                 360 ttt tca cat gtt acg gcg aac caa acc att tac gag gcg gtt gtg agg    1696
Phe Ser His Val Thr Ala Asn Gln Thr Ile Tyr Glu Ala Val Val Arg
365                 370                 375 agt cag aac gtt cat gtg gtt gat ttg gac atc caa cta ggg ctg cag    1744
Ser Gln Asn Val His Val Val Asp Leu Asp Ile Gln Leu Gly Leu Gln
380                 385                 390 tgg ccg tgc ttc ata cag tcc ttg gcc atg cga cca ggg ggt gct cct    1792
Trp Pro Cys Phe Ile Gln Ser Leu Ala Met Arg Pro Gly Gly Ala Pro
395                 400                 405 cat ctc aga att tcg gcc atc gga acg aat gcc gag aat ttg cag aca    1840
His Leu Arg Ile Ser Ala Ile Gly Thr Asn Ala Glu Asn Leu Gln Thr
410                 415                 420 acc aag cga cgg ctg tcc gaa ttt gcc gaa gct ctc aag gtg ccc ttc    1888
Thr Lys Arg Arg Leu Ser Glu Phe Ala Glu Ala Leu Lys Val Pro Phe
425                 430                 435                 440 gag ttc act cca gtg ctc tcg agc ttg gag aat ctc acc gcg gcg atg    1936
Glu Phe Thr Pro Val Leu Ser Ser Leu Glu Asn Leu Thr Ala Ala Met
445                 450                 455 ttg gac att cgg tca gag gag gat ttg gcc atc aat tgc tcc caa gtg    1984
Leu Asp Ile Arg Ser Glu Glu Asp Leu Ala Ile Asn Cys Ser Gln Val
460                 465                 470 ttg cat acg ctt tcc gga gaa gaa gct gtt tta gat aaa ttg ctc agc    2032
Leu His Thr Leu Ser Gly Glu Glu Ala Val Leu Asp Lys Leu Leu Ser
475                 480                 485 atg ttc cac aac ctg aaa ccg aat gtg gtg aca ctg ttg gag gcc gag    2080
Met Phe His Asn Leu Lys Pro Asn Val Val Thr Leu Leu Glu Ala Glu
490                 495                 500 gcc aat cat aat ggc gcc tcg ttc att gcg agg ttt gtc gaa gcg ctg    2128
Ala Asn His Asn Gly Ala Ser Phe Ile Ala Arg Phe Val Glu Ala Leu
505                 510                 515                 520 cac tat tac tgc gcc ctg ttt gat tcc ttg gag gga gct cta ggt cgc    2176
His Tyr Tyr Cys Ala Leu Phe Asp Ser Leu Glu Gly Ala Leu Gly Arg
525                 530                 535 gac agt gcg gat aga tac cat att gag agt aca gca ctc gct gct gag    2224
Asp Ser Ala Asp Arg Tyr His Ile Glu Ser Thr Ala Leu Ala Ala Glu
```

-continued

```
Asp Ser Ala Asp Arg Tyr His Ile Glu Ser Thr Ala Leu Ala Ala Glu
540                 545                 550 atc aag gag att gtt gct ttc aag gga aat agg cgg cgt gtg aga cat    2272
Ile Lys Glu Ile Val Ala Phe Lys Gly Asn Arg Arg Arg Val Arg His
555                 560                 565 gtg cgg tcg gag aca tgg cgg ggc ttg ttt gcg aaa gca gga ttt ctg    2320
Val Arg Ser Glu Thr Trp Arg Gly Leu Phe Ala Lys Ala Gly Phe Leu
570                 575                 580 tcc atg gct ttc agt tcg tat act gtg cag caa gcg cag atg ttg ctg    2368
Ser Met Ala Phe Ser Ser Tyr Thr Val Gln Gln Ala Gln Met Leu Leu
585                 590                 595                 600 gaa gtt ttg aca tcg aag cct atg cag caa gca aac gct aca atg cct    2416
Glu Val Leu Thr Ser Lys Pro Met Gln Gln Ala Asn Ala Thr Met Pro
605                 610                 615 tac aaa ctg tcg cag gaa tcg aca tcc ctg att tta ggg cgg caa gaa    2464
Tyr Lys Leu Ser Gln Glu Ser Thr Ser Leu Ile Leu Gly Arg Gln Glu
620                 625                 630 act ccc gtg att ggc gta tct gct tgg act tgc tag tggctaatca          2510
Thr Pro Val Ile Gly Val Ser Ala Trp Thr Cys
635                 640 aataccaatc ggagctagaa caattaggtt agaaattgtc cataattgta ccagtatatg  2570
tgattgtaga tttagaaaat gcgcctattg tagatttaga aaatgaatga ggactgcggt  2630
ggaaactctg aggcggtgat aattgccggt gatgagtagg cacatagcat gcgcaatctt  2690
caatcgacat gttaacgtaa tgaagtatca atgtacataa gttgatgtaa cagtgccaga  2750
caatctggac tatacgatat cgc                                          2773

<210> SEQ ID NO 4
<211> LENGTH: 643
<212> TYPE: PRT
<213> ORGANISM: Physcomitrella patens

<400> SEQUENCE: 4

Met Ala Ala Thr His Val Val Ser Lys Lys Arg Ser Pro Thr Ile Phe
1               5                   10                  15

Ser Glu Val Ala Thr Ala Thr Cys Lys Arg Trp Lys Ser Glu Ala Ala
            20                  25                  30

Trp His His Val Glu Glu Met Ala Pro Glu Pro Pro Ile Gln Asp
        35                  40                  45

Phe Asp Leu Lys Val Lys Thr Ser Cys Leu Lys Met Val Gln Pro Glu
    50                  55                  60

Pro Thr Ser Val Leu Asp Leu Gln Ala Ser Pro Gly Arg Ser Cys Ser
65                  70                  75                  80

Ser Ser Thr Ser Leu Ser Ser Gly Thr Asp Ser Pro His Ser Ile Ser
            85                  90                  95

Thr Asp Ser Pro Asn Phe Ser Thr Thr Val Gln Gln Val Glu Pro Val
        100                 105                 110

Asp Ile Ala Ser Trp Val Asp Cys Met Ala Leu Pro Glu Phe Glu Asp
    115                 120                 125

Cys Asp Arg His Leu Glu Glu Val Leu Lys Ser Asp Ile Asp Phe Ala
130                 135                 140

Ser Thr Asp Leu Asp Phe Gly Phe Glu Leu Thr Ser Leu Asp His Cys
145                 150                 155                 160

Ser Val Val Thr Glu His Gly Tyr Ser Val Ser Leu Leu Ser Glu Phe
            165                 170                 175

Leu Gly Asp Pro Asp Glu Asn Leu Leu Leu Pro Glu Ser Phe His Asp
```

-continued

```
            180                 185                 190
Ala Lys Arg Leu Gln Glu Leu Asp Asp Ser Leu Ser Ser Met Leu Ser
195                 200                 205

Glu Val Arg Ser Ser Gly Ser Asp Ser Gly Ser Ser Val Pro Thr Thr
210                 215                 220

Val Glu Leu Ala Arg Leu Val Glu Ser Leu Pro Cys Ser Asp Leu Arg
225                 230                 235                 240

Arg His Gly Gly Val Asp Thr Lys His His His His Ser Arg Ser
245                 250                 255

Glu Ser Trp Gly Ser Thr Ser Lys Leu Gln Thr Leu Gln His Pro Glu
260                 265                 270

Asp Ser Gly Leu Gln Leu Val His Met Leu Leu Ala Cys Ala Glu Ala
275                 280                 285

Ile Glu Lys Ser Asp Phe Asn Lys Ala Lys Pro Ile Leu Asp Gln Leu
290                 295                 300

Leu Arg Ser Ser Asp Pro Tyr Gly Asp Pro Met Gln Arg Ile Ala Leu
305                 310                 315                 320

Tyr Phe Gly Glu Ala Leu Thr Asp His Leu Ala Gly Val Val Ser Pro
325                 330                 335

Ser Glu Thr His Leu Leu Ser Asp Ser Lys Leu Ala Tyr Gln Ala Phe
340                 345                 350

Tyr Lys Val Leu Pro Phe Ala Lys Phe Ser His Val Thr Ala Asn Gln
355                 360                 365

Thr Ile Tyr Glu Ala Val Val Arg Ser Gln Asn Val His Val Val Asp
370                 375                 380

Leu Asp Ile Gln Leu Gly Leu Gln Trp Pro Cys Phe Ile Gln Ser Leu
385                 390                 395                 400

Ala Met Arg Pro Gly Gly Ala Pro His Leu Arg Ile Ser Ala Ile Gly
405                 410                 415

Thr Asn Ala Glu Asn Leu Gln Thr Thr Lys Arg Arg Leu Ser Glu Phe
420                 425                 430

Ala Glu Ala Leu Lys Val Pro Phe Glu Phe Thr Pro Val Leu Ser Ser
435                 440                 445

Leu Glu Asn Leu Thr Ala Ala Met Leu Asp Ile Arg Ser Glu Glu Asp
450                 455                 460

Leu Ala Ile Asn Cys Ser Gln Val Leu His Thr Leu Ser Gly Glu Glu
465                 470                 475                 480

Ala Val Leu Asp Lys Leu Leu Ser Met Phe His Asn Leu Lys Pro Asn
485                 490                 495

Val Val Thr Leu Leu Glu Ala Glu Ala Asn His Asn Gly Ala Ser Phe
500                 505                 510

Ile Ala Arg Phe Val Glu Ala Leu His Tyr Tyr Cys Ala Leu Phe Asp
515                 520                 525

Ser Leu Glu Gly Ala Leu Gly Arg Asp Ser Ala Asp Arg Tyr His Ile
530                 535                 540

Glu Ser Thr Ala Leu Ala Ala Glu Ile Lys Glu Ile Val Ala Phe Lys
545                 550                 555                 560

Gly Asn Arg Arg Arg Val Arg His Val Arg Ser Glu Thr Trp Arg Gly
565                 570                 575

Leu Phe Ala Lys Ala Gly Phe Leu Ser Met Ala Phe Ser Ser Tyr Thr
580                 585                 590

Val Gln Gln Ala Gln Met Leu Leu Glu Val Leu Thr Ser Lys Pro Met
595                 600                 605
```

```
Gln Gln Ala Asn Ala Thr Met Pro Tyr Lys Leu Ser Gln Glu Ser Thr
610                 615                 620

Ser Leu Ile Leu Gly Arg Gln Glu Thr Pro Val Ile Gly Val Ser Ala
625                 630                 635                 640

Trp Thr Cys

<210> SEQ ID NO 5
<211> LENGTH: 2281
<212> TYPE: DNA
<213> ORGANISM: Physcomitrella patens
<220> FEATURE:
<221> NAME/KEY: CDS
<222> LOCATION: (218)..(2191)
<223> OTHER INFORMATION: Scarecrow-like gene PpSCL3 (EST 512)

<400> SEQUENCE: 5
atcccgggaa gaagagcgtg aacgtgggag agactgagac atcgtccccg cggttctaca       60
cttgcaggag gtcacatgag agattgcacg tggatcacac tgcacagttt caagattcgg      120
gcgaagccat tttcttgacg accagcttgt gcaagggaga ataaacgta gtacaagctc       180 tgttcctgga acctccttga gttcagtttc cgcgagt atg agt gtg cag tat cga      235
                                        Met Ser Val Gln Tyr Arg
                                        1               5 ccg gag ctg ggt act atg gtt cta aca cct gga tat cca cca ggc aaa      283
Pro Glu Leu Gly Thr Met Val Leu Thr Pro Gly Tyr Pro Pro Gly Lys
10                  15                  20 gaa aga gag tat ttg tca gac act gct aat agt caa cag aca ccc agc      331
Glu Arg Glu Tyr Leu Ser Asp Thr Ala Asn Ser Gln Gln Thr Pro Ser
25                  30                  35 tat tat ggt gcg cag aag tct tat gcg gat ggt caa agg cag agt gca      379
Tyr Tyr Gly Ala Gln Lys Ser Tyr Ala Asp Gly Gln Arg Gln Ser Ala
40                  45                  50 tat ggt atg aaa aac aaa agt cac agt tcg cct gta tct ccc cta tct      427
Tyr Gly Met Lys Asn Lys Ser His Ser Ser Pro Val Ser Pro Leu Ser
55                  60                  65                  70 ccg caa gat tca tct cag gcc gct tcg gat aat gga caa agg atg tct      475
Pro Gln Asp Ser Ser Gln Ala Ala Ser Asp Asn Gly Gln Arg Met Ser
75                  80                  85 gca ggc tgg agc tct gca tct tat cag agc gaa tcc tcc tct cat agt      523
Ala Gly Trp Ser Ser Ala Ser Tyr Gln Ser Glu Ser Ser Ser His Ser
90                  95                  100 gat ggt tct tta gag ggt cct gga aaa ctg gaa gag gca gac tat tat      571
Asp Gly Ser Leu Glu Gly Pro Gly Lys Leu Glu Glu Ala Asp Tyr Tyr
105                 110                 115 gga cgc caa cat cgt cat ggt gag cag tta act ggg tca gta gca tat      619
Gly Arg Gln His Arg His Gly Glu Gln Leu Thr Gly Ser Val Ala Tyr
120                 125                 130 cat aat acg ccg tct tct gtt ttg aga ccc atg gga tat cca gct gaa      667
His Asn Thr Pro Ser Ser Val Leu Arg Pro Met Gly Tyr Pro Ala Glu
135                 140                 145                 150 act gct cag gct tat caa atg cct aac tat cag cag gcc gta cga tat      715
Thr Ala Gln Ala Tyr Gln Met Pro Asn Tyr Gln Gln Ala Val Arg Tyr
155                 160                 165 ata cca gag gag caa tat gcc cag tct cag agc aat tat gcg cag agg      763
Ile Pro Glu Glu Gln Tyr Ala Gln Ser Gln Ser Asn Tyr Ala Gln Arg
170                 175                 180 aac cca gaa atg gca cat atg ctg caa gtt ctg gag agc gcg ctt ttg      811
Asn Pro Glu Met Ala His Met Leu Gln Val Leu Glu Ser Ala Leu Leu
185                 190                 195
```

| | | |
|---|---|---|
| gat gac gac gat ggt gca gat ttg cca gga tct ctt ggg aat gga cat<br>Asp Asp Asp Asp Gly Ala Asp Leu Pro Gly Ser Leu Gly Asn Gly His<br>200                    205                    210 | 859 |
| gat cct gca tca gaa ggg aac tgg gca gac acg att gag gag ttt atg<br>Asp Pro Ala Ser Glu Gly Asn Trp Ala Asp Thr Ile Glu Glu Phe Met<br>215                    220                    225                    230 | 907 |
| gct gcc gat gcc tcg cca gct gat tca tcc act gta acg tca gct acc<br>Ala Ala Asp Ala Ser Pro Ala Asp Ser Ser Thr Val Thr Ser Ala Thr<br>235                    240                    245 | 955 |
| act cca cct gaa tat ggg aag cag tgt cgc aac ggg agt aca aac aac<br>Thr Pro Pro Glu Tyr Gly Lys Gln Cys Arg Asn Gly Ser Thr Asn Asn<br>250                    255                    260 | 1003 |
| tat act gga gcc gcc act gct aga gtg gaa gaa cca cct cct caa aaa<br>Tyr Thr Gly Ala Ala Thr Ala Arg Val Glu Glu Pro Pro Pro Gln Lys<br>265                    270                    275 | 1051 |
| ttg gtt gtg gga aca agg agt aga tca gaa cag ctg ctt gta gct tgc<br>Leu Val Val Gly Thr Arg Ser Arg Ser Glu Gln Leu Leu Val Ala Cys<br>280                    285                    290 | 1099 |
| gct gaa gct ctc tca aat aat gat atg ccg tta gcg aac gta cta atc<br>Ala Glu Ala Leu Ser Asn Asn Asp Met Pro Leu Ala Asn Val Leu Ile<br>295                    300                    305                    310 | 1147 |
| gct caa ctc aat caa gtg gtt tcc ata tat ggt gat cca atg cag cgt<br>Ala Gln Leu Asn Gln Val Val Ser Ile Tyr Gly Asp Pro Met Gln Arg<br>315                    320                    325 | 1195 |
| ttg gct gct tat atg gtc gag ggt ctt gtg gct cgg gtc gct gcc tca<br>Leu Ala Ala Tyr Met Val Glu Gly Leu Val Ala Arg Val Ala Ala Ser<br>330                    335                    340 | 1243 |
| gga aaa ggc att tat aga tca ctg aag tgt aaa gat cct ccg acc aga<br>Gly Lys Gly Ile Tyr Arg Ser Leu Lys Cys Lys Asp Pro Pro Thr Arg<br>345                    350                    355 | 1291 |
| gac cta ctt tca gca atg cag att ctg tac gaa gtc tgt cca tac ttt<br>Asp Leu Leu Ser Ala Met Gln Ile Leu Tyr Glu Val Cys Pro Tyr Phe<br>360                    365                    370 | 1339 |
| aaa ttt ggg tac atg gca gct aat gga tcc atc gct gaa gct ttt caa<br>Lys Phe Gly Tyr Met Ala Ala Asn Gly Ser Ile Ala Glu Ala Phe Gln<br>375                    380                    385                    390 | 1387 |
| aat gaa tct cgg gtt cat atc atc gac ttt caa ata gct caa ggc aca<br>Asn Glu Ser Arg Val His Ile Ile Asp Phe Gln Ile Ala Gln Gly Thr<br>395                    400                    405 | 1435 |
| caa tgg aca act ctt att caa gcc ttg gct gct cga cca ggg ggt cca<br>Gln Trp Thr Thr Leu Ile Gln Ala Leu Ala Ala Arg Pro Gly Gly Pro<br>410                    415                    420 | 1483 |
| cct cac ttg cga atc act ggt atc gat gat cct atg cct gga ccg aat<br>Pro His Leu Arg Ile Thr Gly Ile Asp Asp Pro Met Pro Gly Pro Asn<br>425                    430                    435 | 1531 |
| tcg aat gca ggt gtt gag atg gtt ggg aag cgg ctt gct aaa cta gcg<br>Ser Asn Ala Gly Val Glu Met Val Gly Lys Arg Leu Ala Lys Leu Ala<br>440                    445                    450 | 1579 |
| gaa gct gtt gga gtt ccc ttc gac ttc cat cct gta gcg aag aaa ggg<br>Glu Ala Val Gly Val Pro Phe Asp Phe His Pro Val Ala Lys Lys Gly<br>455                    460                    465                    470 | 1627 |
| cca gag gta gaa gca tgg atg ctg gag cgg cag ccg ggg gaa gct ctt<br>Pro Glu Val Glu Ala Trp Met Leu Glu Arg Gln Pro Gly Glu Ala Leu<br>475                    480                    485 | 1675 |
| gca gtc aat ttc gcc cta cat ctc cac cat atg cct gac gag agt gtc<br>Ala Val Asn Phe Ala Leu His Leu His His Met Pro Asp Glu Ser Val<br>490                    495                    500 | 1723 |
| tgc aca agc aat cct cgg gat cgt ata ctg cat atg gtc aaa gcc ctc<br>Cys Thr Ser Asn Pro Arg Asp Arg Ile Leu His Met Val Lys Ala Leu<br>505                    510                    515 | 1771 |

```
aac ccc aaa gtt gtg acc ctt gtc gag cag gag tct aat act aac act       1819
Asn Pro Lys Val Val Thr Leu Val Glu Gln Glu Ser Asn Thr Asn Thr
520                 525                 530 gct cca ttc ttt cca cgc ttt ttg gaa gct atg aat tac tac gct gca       1867
Ala Pro Phe Phe Pro Arg Phe Leu Glu Ala Met Asn Tyr Tyr Ala Ala
535                 540                 545                 550 ata ttt gag tct ctg gac att acc ttg gcc cgt gag agc aag gag cgt       1915
Ile Phe Glu Ser Leu Asp Ile Thr Leu Ala Arg Glu Ser Lys Glu Arg
555                 560                 565 gtg aat gtt gag caa caa tgt tta gct cgc gat atc gtc aac atc att       1963
Val Asn Val Glu Gln Gln Cys Leu Ala Arg Asp Ile Val Asn Ile Ile
570                 575                 580 gct tgt gaa ggt att gat aga gtt gaa agg cat gag atg atg ggg aaa       2011
Ala Cys Glu Gly Ile Asp Arg Val Glu Arg His Glu Met Met Gly Lys
585                 590                 595 tgg cgc gcg cgc ctg act atg gct ggt ttt cgt ccg tat cct tta agc       2059
Trp Arg Ala Arg Leu Thr Met Ala Gly Phe Arg Pro Tyr Pro Leu Ser
600                 605                 610 caa aca gtg aac aac aca ata aag aca ttg ctg gag tca tat agt gat       2107
Gln Thr Val Asn Asn Thr Ile Lys Thr Leu Leu Glu Ser Tyr Ser Asp
615                 620                 625                 630 aag tat aga ctt aaa gac gag ggc gga gca ctt tat ctg ggc tgg aag       2155
Lys Tyr Arg Leu Lys Asp Glu Gly Gly Ala Leu Tyr Leu Gly Trp Lys
635                 640                 645 aat cgg tcc ctc att gtt tcc tct gca tgg cag tag acctcgtctg            2201
Asn Arg Ser Leu Ile Val Ser Ser Ala Trp Gln
650                 655 ttctcactgt atatattctt atagtgtggt tcagcctcga gttatctgag gacctgtctc     2261
atttggtaag gcagtactgc                                                 2281

<210> SEQ ID NO 6
<211> LENGTH: 657
<212> TYPE: PRT
<213> ORGANISM: Physcomitrella patens

<400> SEQUENCE: 6

Met Ser Val Gln Tyr Arg Pro Glu Leu Gly Thr Met Val Leu Thr Pro
1               5                   10                  15

Gly Tyr Pro Pro Gly Lys Glu Arg Glu Tyr Leu Ser Asp Thr Ala Asn
            20                  25                  30

Ser Gln Gln Thr Pro Ser Tyr Tyr Gly Ala Gln Lys Ser Tyr Ala Asp
        35                  40                  45

Gly Gln Arg Gln Ser Ala Tyr Gly Met Lys Asn Lys Ser His Ser Ser
    50                  55                  60

Pro Val Ser Pro Leu Ser Pro Gln Asp Ser Ser Gln Ala Ala Ser Asp
65                  70                  75                  80

Asn Gly Gln Arg Met Ser Ala Gly Trp Ser Ser Ala Ser Tyr Gln Ser
                85                  90                  95

Glu Ser Ser Ser His Ser Asp Gly Ser Leu Glu Gly Pro Gly Lys Leu
            100                 105                 110

Glu Glu Ala Asp Tyr Tyr Gly Arg Gln His Arg His Gly Glu Gln Leu
        115                 120                 125

Thr Gly Ser Val Ala Tyr His Asn Thr Pro Ser Ser Val Leu Arg Pro
    130                 135                 140

Met Gly Tyr Pro Ala Glu Thr Ala Gln Ala Tyr Gln Met Pro Asn Tyr
145                 150                 155                 160
```

```
Gln Gln Ala Val Arg Tyr Ile Pro Glu Glu Gln Tyr Ala Gln Ser Gln
165                 170                 175

Ser Asn Tyr Ala Gln Arg Asn Pro Glu Met Ala His Met Leu Gln Val
180                 185                 190

Leu Glu Ser Ala Leu Leu Asp Asp Asp Gly Ala Asp Leu Pro Gly
195                 200                 205

Ser Leu Gly Asn Gly His Asp Pro Ala Ser Glu Gly Asn Trp Ala Asp
210                 215                 220

Thr Ile Glu Glu Phe Met Ala Ala Asp Ala Ser Pro Ala Asp Ser Ser
225                 230                 235                 240

Thr Val Thr Ser Ala Thr Thr Pro Pro Glu Tyr Gly Lys Gln Cys Arg
245                 250                 255

Asn Gly Ser Thr Asn Asn Tyr Thr Gly Ala Ala Thr Ala Arg Val Glu
260                 265                 270

Glu Pro Pro Pro Gln Lys Leu Val Val Gly Thr Arg Ser Arg Ser Glu
275                 280                 285

Gln Leu Leu Val Ala Cys Ala Glu Ala Leu Ser Asn Asn Asp Met Pro
290                 295                 300

Leu Ala Asn Val Leu Ile Ala Gln Leu Asn Gln Val Val Ser Ile Tyr
305                 310                 315                 320

Gly Asp Pro Met Gln Arg Leu Ala Ala Tyr Met Val Glu Gly Leu Val
325                 330                 335

Ala Arg Val Ala Ala Ser Gly Lys Gly Ile Tyr Arg Ser Leu Lys Cys
340                 345                 350

Lys Asp Pro Pro Thr Arg Asp Leu Leu Ser Ala Met Gln Ile Leu Tyr
355                 360                 365

Glu Val Cys Pro Tyr Phe Lys Phe Gly Tyr Met Ala Ala Asn Gly Ser
370                 375                 380

Ile Ala Glu Ala Phe Gln Asn Glu Ser Arg Val His Ile Ile Asp Phe
385                 390                 395                 400

Gln Ile Ala Gln Gly Thr Gln Trp Thr Thr Leu Ile Gln Ala Leu Ala
405                 410                 415

Ala Arg Pro Gly Gly Pro Pro His Leu Arg Ile Thr Gly Ile Asp Asp
420                 425                 430

Pro Met Pro Gly Pro Asn Ser Asn Ala Gly Val Glu Met Val Gly Lys
435                 440                 445

Arg Leu Ala Lys Leu Ala Glu Ala Val Gly Val Pro Phe Asp Phe His
450                 455                 460

Pro Val Ala Lys Lys Gly Pro Glu Val Glu Ala Trp Met Leu Glu Arg
465                 470                 475                 480

Gln Pro Gly Glu Ala Leu Ala Val Asn Phe Ala Leu His Leu His His
485                 490                 495

Met Pro Asp Glu Ser Val Cys Thr Ser Asn Pro Arg Asp Arg Ile Leu
500                 505                 510

His Met Val Lys Ala Leu Asn Pro Lys Val Val Thr Leu Val Glu Gln
515                 520                 525

Glu Ser Asn Thr Asn Thr Ala Pro Phe Phe Pro Arg Phe Leu Glu Ala
530                 535                 540

Met Asn Tyr Tyr Ala Ala Ile Phe Glu Ser Leu Asp Ile Thr Leu Ala
545                 550                 555                 560

Arg Glu Ser Lys Glu Arg Val Asn Val Glu Gln Gln Cys Leu Ala Arg
565                 570                 575

Asp Ile Val Asn Ile Ile Ala Cys Glu Gly Ile Asp Arg Val Glu Arg
```

His Glu Met Met Gly Lys Trp Arg Ala Arg Leu Thr Met Ala Gly Phe
595                 600                 605

Arg Pro Tyr Pro Leu Ser Gln Thr Val Asn Asn Thr Ile Lys Thr Leu
610                 615                 620

Leu Glu Ser Tyr Ser Asp Lys Tyr Arg Leu Lys Asp Glu Gly Gly Ala
625                 630                 635                 640

Leu Tyr Leu Gly Trp Lys Asn Arg Ser Leu Ile Val Ser Ser Ala Trp
645                 650                 655

Gln

<210> SEQ ID NO 7
<211> LENGTH: 2610
<212> TYPE: DNA
<213> ORGANISM: Glycine max
<220> FEATURE:
<221> NAME/KEY: CDS
<222> LOCATION: (124)..(2079)
<223> OTHER INFORMATION: Scarecrow-like gene GmSCL1 (GM59556757)

<400> SEQUENCE: 7

```
actaaaacac ccatactctc tctttctctt tcattctttg atgcctttct acaaaaacac    60
aaccttttaa ctgttatttt tttttttttc gtttgctcct tattttcttc gccgaatcct   120 aga atg tca tcg ccg ggg ttc cct ggc ggc ggt agt gcg tct gag ttt    168
    Met Ser Ser Pro Gly Phe Pro Gly Gly Gly Ser Ala Ser Glu Phe
    1               5                   10                  15 ttc gct gga gcg ggt gtt ttc ggc ggc aga tcc att ccg ggg gcc acc    216
Phe Ala Gly Ala Gly Val Phe Gly Gly Arg Ser Ile Pro Gly Ala Thr
 20                  25                  30 atg aac aac ccc aac gcc gcc gct tcc gcc acc atc aac aac ctc cac    264
Met Asn Asn Pro Asn Ala Ala Ala Ser Ala Thr Ile Asn Asn Leu His
 35                  40                  45 cct ctc tac cga acc caa caa caa cag aac ctt ccc gca atg ttt cta    312
Pro Leu Tyr Arg Thr Gln Gln Gln Gln Asn Leu Pro Ala Met Phe Leu
 50                  55                  60 gat cct tcc tcg cag atc gcc caa cgc caa aca cca acc ttc atc ggt    360
Asp Pro Ser Ser Gln Ile Ala Gln Arg Gln Thr Pro Thr Phe Ile Gly
 65                  70                  75 aag cgc acc cta acc gaa ttc caa gcc tac aac caa acc aac aac aac    408
Lys Arg Thr Leu Thr Glu Phe Gln Ala Tyr Asn Gln Thr Asn Asn Asn
 80                  85                  90                  95 ccc aac cac gtc ctc tcg aac ctc ctg ctt cgt tcc gtt aag ccc cgg    456
Pro Asn His Val Leu Ser Asn Leu Leu Leu Arg Ser Val Lys Pro Arg
100                 105                 110 acc agt tta tac cac acc tct atg gac ttt cct gtt ccc gaa ttg caa    504
Thr Ser Leu Tyr His Thr Ser Met Asp Phe Pro Val Pro Glu Leu Gln
115                 120                 125 aac caa aac ctt tat tcc aac caa acg cag cgt ttt ggt gtt ccg tta    552
Asn Gln Asn Leu Tyr Ser Asn Gln Thr Gln Arg Phe Gly Val Pro Leu
130                 135                 140 ctt cac cag ctt cgt cct cag ccc att aat ctc ccc aac aac ggg ccc    600
Leu His Gln Leu Arg Pro Gln Pro Ile Asn Leu Pro Asn Asn Gly Pro
145                 150                 155 gtg ccc atg aca ggc cca aat ttc ggt tac cgg aac tcg aat ttg ggc    648
Val Pro Met Thr Gly Pro Asn Phe Gly Tyr Arg Asn Ser Asn Leu Gly
160                 165                 170                 175 tta cca cag aac cag aac cgg gtt cgt gtt tct ctc cct gtt tct gtt    696
Leu Pro Gln Asn Gln Asn Arg Val Arg Val Ser Leu Pro Val Ser Val
180                 185                 190
```

-continued

```
ccg gtt cag gtt cac tca tct gaa ccg gaa aag aag atc atg gac cac      744
Pro Val Gln Val His Ser Ser Glu Pro Glu Lys Lys Ile Met Asp His
195                 200                 205 agg ctt ctg gaa ttg gag aag cag ctt ctg gaa gat aac gac gac gaa      792
Arg Leu Leu Glu Leu Glu Lys Gln Leu Leu Glu Asp Asn Asp Asp Glu
210                 215                 220 gga gaa gct gat gct gcg tct gtg ata acc acg agc gag tgg tcc gag      840
Gly Glu Ala Asp Ala Ala Ser Val Ile Thr Thr Ser Glu Trp Ser Glu
225                 230                 235 act tat cag aat tta atc agt ccc agt ccg gtt cag aaa ccg gtt ttg      888
Thr Tyr Gln Asn Leu Ile Ser Pro Ser Pro Val Gln Lys Pro Val Leu
240                 245                 250                 255 acg acg acg tcg ccg act tct tcc acg acg tcg tcc acg tca tct tct      936
Thr Thr Thr Ser Pro Thr Ser Ser Thr Thr Ser Ser Thr Ser Ser Ser
260                 265                 270 tcc tcc gtg gct tcg cct gct tcc gga tgc tcc aag caa acg ctc atg      984
Ser Ser Val Ala Ser Pro Ala Ser Gly Cys Ser Lys Gln Thr Leu Met
275                 280                 285 gaa gcc gca tct gca att gtt gaa ggt aaa cac gat gtt gcg gcg gag     1032
Glu Ala Ala Ser Ala Ile Val Glu Gly Lys His Asp Val Ala Ala Glu
290                 295                 300 atc ctg aac cgg ttg aac ggt gtg aac cgg agt gat agg ttg acg gat     1080
Ile Leu Asn Arg Leu Asn Gly Val Asn Arg Ser Asp Arg Leu Thr Asp
305                 310                 315 tgc atg gtt tcg gcg ttg aaa tcg agg atg aat ccg gtg gag tat cct     1128
Cys Met Val Ser Ala Leu Lys Ser Arg Met Asn Pro Val Glu Tyr Pro
320                 325                 330                 335 ccg ccg gtg gcg gag ctt ttc agg aag gag cac gcc gat tcg act cag     1176
Pro Pro Val Ala Glu Leu Phe Arg Lys Glu His Ala Asp Ser Thr Gln
340                 345                 350 atg ctc ttg gag aac tcg gtg tgc ttc acg gta ggg ttc atg gcg gcg     1224
Met Leu Leu Glu Asn Ser Val Cys Phe Thr Val Gly Phe Met Ala Ala
355                 360                 365 aat ctc gcg att ctg gaa gcc gca ttt gag gag aaa acg gag acg agc     1272
Asn Leu Ala Ile Leu Glu Ala Ala Phe Glu Glu Lys Thr Glu Thr Ser
370                 375                 380 agg ttc tgc gtg gtg gat ttt gag att gga caa ggg aag cag tat ttg     1320
Arg Phe Cys Val Val Asp Phe Glu Ile Gly Gln Gly Lys Gln Tyr Leu
385                 390                 395 cac ctc ctc aac gcg ctc tcg gcg cgt gga cag aac gtg gcg gtg aag     1368
His Leu Leu Asn Ala Leu Ser Ala Arg Gly Gln Asn Val Ala Val Lys
400                 405                 410                 415 atc gca gcc gta gca gaa aaa gga ggt gag gag aga gtg cgg gct gtg     1416
Ile Ala Ala Val Ala Glu Lys Gly Gly Glu Glu Arg Val Arg Ala Val
420                 425                 430 gga gac atg ctg aga tta ctc gcg gag agg ctg agg atc cgg ttc gag     1464
Gly Asp Met Leu Arg Leu Leu Ala Glu Arg Leu Arg Ile Arg Phe Glu
435                 440                 445 ttc aaa atc gtc gcg act cag aaa atc gcc gag ttg act cgt gag tcg     1512
Phe Lys Ile Val Ala Thr Gln Lys Ile Ala Glu Leu Thr Arg Glu Ser
450                 455                 460 ctg gga tgc gat gcg gac gat gtt ctc atg gtg aac ttc gcg ttc aag     1560
Leu Gly Cys Asp Ala Asp Asp Val Leu Met Val Asn Phe Ala Phe Lys
465                 470                 475 ctg aac aag att ccg gac gag agc gtc tcc ccg gaa aac cct cgg gac     1608
Leu Asn Lys Ile Pro Asp Glu Ser Val Ser Pro Glu Asn Pro Arg Asp
480                 485                 490                 495 gag ctt ctt cgg cgc gtg aag aga ctc gcg ccg cgc gtg gtg acg gtt     1656
Glu Leu Leu Arg Arg Val Lys Arg Leu Ala Pro Arg Val Val Thr Val
```

| | | |
|---|---|---|
| gtg gag cag gag ata aac ggg aac acg gcg ccg ttt ttg gcg cgc gtg<br>Val Glu Gln Glu Ile Asn Gly Asn Thr Ala Pro Phe Leu Ala Arg Val<br>515                     520                     525 | | 1704 |
| gcg gaa acg ctg tcg tat tac ggc gcg ttg ttg gag tcc att gag gcc<br>Ala Glu Thr Leu Ser Tyr Tyr Gly Ala Leu Leu Glu Ser Ile Glu Ala<br>530                     535                     540 | | 1752 |
| acc acg gtg ggg aaa gat aac agc att aac aac tca gac cga gtc aga<br>Thr Thr Val Gly Lys Asp Asn Ser Ile Asn Asn Ser Asp Arg Val Arg<br>545                     550                     555 | | 1800 |
| ctc gag gag gga ctg agt cga aaa ttg cat aac tcg gtg gcg tgc gaa<br>Leu Glu Glu Gly Leu Ser Arg Lys Leu His Asn Ser Val Ala Cys Glu<br>560                     565                     570                     575 | | 1848 |
| gga aga gat cgc gtg gaa cgg tgc gaa gtg ttt gga aaa tgg cgc gcg<br>Gly Arg Asp Arg Val Glu Arg Cys Glu Val Phe Gly Lys Trp Arg Ala<br>580                     585                     590 | | 1896 |
| cgt atg agc atg gcg ggg ttt gag tta aaa cca ctg agt caa agc atg<br>Arg Met Ser Met Ala Gly Phe Glu Leu Lys Pro Leu Ser Gln Ser Met<br>595                     600                     605 | | 1944 |
| gtc gag tca att aaa gcg cga ctc atc tct gcc aac aac cga gtc aac<br>Val Glu Ser Ile Lys Ala Arg Leu Ile Ser Ala Asn Asn Arg Val Asn<br>610                     615                     620 | | 1992 |
| tcg gga ctc acc gta aaa gaa gag aac gga ggg att tgc ttt ggt tgg<br>Ser Gly Leu Thr Val Lys Glu Glu Asn Gly Gly Ile Cys Phe Gly Trp<br>625                     630                     635 | | 2040 |
| atg gga aga aca ctc aca gtc gca tct gct tgg cgt taa cttggctcat<br>Met Gly Arg Thr Leu Thr Val Ala Ser Ala Trp Arg<br>640                     645                     650 | | 2089 |
| ttatttttct ttcttttttc tttttatttt ggttcggaat attattatat ataatatcac | | 2149 |
| attgttacta tattttaacg tcatctagag ataatggaaa ggcaaagaga atagatttgg | | 2209 |
| taaattatta ttattataaa tatagtatga taaaagggtg aaaagaaaat ctcaaggaaa | | 2269 |
| gcccctcctc ttggttctac cgaactaaaa ctaataaaga agtgtttgga ttccgagaag | | 2329 |
| actcatgtta catttattga ttcttctatg tattagttgt tgatatgctt ttttatttt | | 2389 |
| atttttatttt tttggtttat catcttcact tgggtgtgtg aaaggagttg gttgctgttt | | 2449 |
| ggtagatagc tgacttgtgt gtgatacaat ggattggttt gccctcgcat taccgacaaa | | 2509 |
| cgagggctcc acttatagga tgcatttttg ggggtttagt tggacttgga acttccctgt | | 2569 |
| tatccaaaaa aaaaaaaaaa aaagagagag accgacacgc a | | 2610 |

<210> SEQ ID NO 8
<211> LENGTH: 651
<212> TYPE: PRT
<213> ORGANISM: Glycine max

<400> SEQUENCE: 8

Met Ser Ser Pro Gly Phe Pro Gly Gly Gly Ser Ala Ser Glu Phe Phe
1                   5                     10                     15

Ala Gly Ala Gly Val Phe Gly Gly Arg Ser Ile Pro Gly Ala Thr Met
                 20                     25                     30

Asn Asn Pro Asn Ala Ala Ala Ser Ala Thr Ile Asn Asn Leu His Pro
        35                   40                     45

Leu Tyr Arg Thr Gln Gln Gln Asn Leu Pro Ala Met Phe Leu Asp
50                     55                     60

Pro Ser Ser Gln Ile Ala Gln Arg Gln Thr Pro Thr Phe Ile Gly Lys
65                     70                     75                     80

-continued

```
Arg Thr Leu Thr Glu Phe Gln Ala Tyr Asn Gln Thr Asn Asn Asn Pro
 85                  90                  95

Asn His Val Leu Ser Asn Leu Leu Leu Arg Ser Val Lys Pro Arg Thr
100                 105                 110

Ser Leu Tyr His Thr Ser Met Asp Phe Pro Val Pro Glu Leu Gln Asn
115                 120                 125

Gln Asn Leu Tyr Ser Asn Gln Thr Gln Arg Phe Gly Val Pro Leu Leu
130                 135                 140

His Gln Leu Arg Pro Gln Pro Ile Asn Leu Pro Asn Asn Gly Pro Val
145                 150                 155                 160

Pro Met Thr Gly Pro Asn Phe Gly Tyr Arg Asn Ser Asn Leu Gly Leu
165                 170                 175

Pro Gln Asn Gln Asn Arg Val Arg Val Ser Leu Pro Val Ser Val Pro
180                 185                 190

Val Gln Val His Ser Ser Glu Pro Glu Lys Lys Ile Met Asp His Arg
195                 200                 205

Leu Leu Glu Leu Glu Lys Gln Leu Leu Glu Asp Asn Asp Asp Glu Gly
210                 215                 220

Glu Ala Asp Ala Ala Ser Val Ile Thr Thr Ser Glu Trp Ser Glu Thr
225                 230                 235                 240

Tyr Gln Asn Leu Ile Ser Pro Ser Pro Val Gln Lys Pro Val Leu Thr
245                 250                 255

Thr Thr Ser Pro Thr Ser Ser Thr Thr Ser Ser Thr Ser Ser Ser Ser
260                 265                 270

Ser Val Ala Ser Pro Ala Ser Gly Cys Ser Lys Gln Thr Leu Met Glu
275                 280                 285

Ala Ala Ser Ala Ile Val Glu Gly Lys His Asp Val Ala Ala Glu Ile
290                 295                 300

Leu Asn Arg Leu Asn Gly Val Asn Arg Ser Asp Arg Leu Thr Asp Cys
305                 310                 315                 320

Met Val Ser Ala Leu Lys Ser Arg Met Asn Pro Val Glu Tyr Pro Pro
325                 330                 335

Pro Val Ala Glu Leu Phe Arg Lys Glu His Ala Asp Ser Thr Gln Met
340                 345                 350

Leu Leu Glu Asn Ser Val Cys Phe Thr Val Gly Phe Met Ala Ala Asn
355                 360                 365

Leu Ala Ile Leu Glu Ala Ala Phe Glu Glu Lys Thr Glu Thr Ser Arg
370                 375                 380

Phe Cys Val Val Asp Phe Glu Ile Gly Gln Gly Lys Gln Tyr Leu His
385                 390                 395                 400

Leu Leu Asn Ala Leu Ser Ala Arg Gly Gln Asn Val Ala Val Lys Ile
405                 410                 415

Ala Ala Val Ala Glu Lys Gly Gly Glu Glu Arg Val Arg Ala Val Gly
420                 425                 430

Asp Met Leu Arg Leu Leu Ala Glu Arg Leu Arg Ile Arg Phe Glu Phe
435                 440                 445

Lys Ile Val Ala Thr Gln Lys Ile Ala Glu Leu Thr Arg Glu Ser Leu
450                 455                 460

Gly Cys Asp Ala Asp Asp Val Leu Met Val Asn Phe Ala Phe Lys Leu
465                 470                 475                 480

Asn Lys Ile Pro Asp Glu Ser Val Ser Pro Glu Asn Pro Arg Asp Glu
485                 490                 495

Leu Leu Arg Arg Val Lys Arg Leu Ala Pro Arg Val Val Thr Val Val
```

```
                500                 505                 510
Glu Gln Glu Ile Asn Gly Asn Thr Ala Pro Phe Leu Ala Arg Val Ala
515                 520                 525

Glu Thr Leu Ser Tyr Tyr Gly Ala Leu Leu Glu Ser Ile Glu Ala Thr
530                 535                 540

Thr Val Gly Lys Asp Asn Ser Ile Asn Asn Ser Asp Arg Val Arg Leu
545                 550                 555                 560

Glu Glu Gly Leu Ser Arg Lys Leu His Asn Ser Val Ala Cys Glu Gly
565                 570                 575

Arg Asp Arg Val Glu Arg Cys Glu Val Phe Gly Lys Trp Arg Ala Arg
580                 585                 590

Met Ser Met Ala Gly Phe Glu Leu Lys Pro Leu Ser Gln Ser Met Val
595                 600                 605

Glu Ser Ile Lys Ala Arg Leu Ile Ser Ala Asn Asn Arg Val Asn Ser
610                 615                 620

Gly Leu Thr Val Lys Glu Glu Asn Gly Gly Ile Cys Phe Gly Trp Met
625                 630                 635                 640

Gly Arg Thr Leu Thr Val Ala Ser Ala Trp Arg
645                 650

<210> SEQ ID NO 9
<211> LENGTH: 18
<212> TYPE: DNA
<213> ORGANISM: Artificial
<220> FEATURE:
<223> OTHER INFORMATION: Sequencing primer
<220> FEATURE:
<221> NAME/KEY: misc_feature
<222> LOCATION: (1)..(18)

<400> SEQUENCE: 9
caggaaacag ctatgacc                                                 18

<210> SEQ ID NO 10
<211> LENGTH: 19
<212> TYPE: DNA
<213> ORGANISM: Artificial
<220> FEATURE:
<223> OTHER INFORMATION: Sequencing primer
<220> FEATURE:
<221> NAME/KEY: misc_feature
<222> LOCATION: (1)..(19)

<400> SEQUENCE: 10
ctaaagggaa caaaagctg                                                19

<210> SEQ ID NO 11
<211> LENGTH: 18
<212> TYPE: DNA
<213> ORGANISM: Artificial
<220> FEATURE:
<223> OTHER INFORMATION: Sequencing primer
<220> FEATURE:
<221> NAME/KEY: misc_feature
<222> LOCATION: (1)..(18)

<400> SEQUENCE: 11
tgtaaaacga cggccagt                                                 18

<210> SEQ ID NO 12
<211> LENGTH: 25
<212> TYPE: DNA
<213> ORGANISM: Artificial
```

<220> FEATURE:
<223> OTHER INFORMATION: 5' RACE PCR primer for PpSCL-1 (EST 386)
<220> FEATURE:
<221> NAME/KEY: misc_feature
<222> LOCATION: (1)..(25)

<400> SEQUENCE: 12
gagggaaagc tgtggcgagc taaaa                                    25

<210> SEQ ID NO 13
<211> LENGTH: 32
<212> TYPE: DNA
<213> ORGANISM: Artificial
<220> FEATURE:
<223> OTHER INFORMATION: RT-PCT primer RC896 for PpSCL-1 (EST 386)
<220> FEATURE:
<221> NAME/KEY: misc_feature
<222> LOCATION: (1)..(32)

<400> SEQUENCE: 13
atcccgggag acaagctaag caagtaagca ag                            32

<210> SEQ ID NO 14
<211> LENGTH: 34
<212> TYPE: DNA
<213> ORGANISM: Artificial
<220> FEATURE:
<223> OTHER INFORMATION: RT-PCR primer RC897 for PpSCL-1 (EST 386)
<220> FEATURE:
<221> NAME/KEY: misc_feature
<222> LOCATION: (1)..(34)

<400> SEQUENCE: 14
gcgagctcgg atatagtaca gagctgcagg cgaa                          34

<210> SEQ ID NO 15
<211> LENGTH: 25
<212> TYPE: DNA
<213> ORGANISM: Artificial
<220> FEATURE:
<223> OTHER INFORMATION: 5' Race PCR primer for PpSCL2 (EST 166)
<220> FEATURE:
<221> NAME/KEY: misc_feature
<222> LOCATION: (1)..(25)

<400> SEQUENCE: 15
gtcggaggat cggagtaact ggtct                                    25

<210> SEQ ID NO 16
<211> LENGTH: 34
<212> TYPE: DNA
<213> ORGANISM: Artificial
<220> FEATURE:
<223> OTHER INFORMATION: RT-PCR primer RC618 for PpSCL2 (EST 166)
<220> FEATURE:
<221> NAME/KEY: misc_feature
<222> LOCATION: (1)..(34)

<400> SEQUENCE: 16
gcgatatcgg cggtgatctc cgtttcctgg ctct                          34

<210> SEQ ID NO 17
<211> LENGTH: 34
<212> TYPE: DNA
<213> ORGANISM: Artificial
<220> FEATURE:
<223> OTHER INFORMATION: RT-PCR primer RC619 for PpSCL2 (EST 166)
<220> FEATURE:
<221> NAME/KEY: misc_feature

<222> LOCATION: (1)..(34)

<400> SEQUENCE: 17
gcgatatcgt atagtccaga ttgtctggca ctgt    34

<210> SEQ ID NO 18
<211> LENGTH: 25
<212> TYPE: DNA
<213> ORGANISM: Artificial
<220> FEATURE:
<223> OTHER INFORMATION: 5' Race PCR primer for PpSCL3 (EST 512)
<220> FEATURE:
<221> NAME/KEY: misc_feature
<222> LOCATION: (1)..(25)

<400> SEQUENCE: 18
gtgaaccccc tggtcgagca gccaa    25

<210> SEQ ID NO 19
<211> LENGTH: 28
<212> TYPE: DNA
<213> ORGANISM: Artificial
<220> FEATURE:
<223> OTHER INFORMATION: RT-PCR primer RC705 for PpSCL3 (EST 512)
<220> FEATURE:
<221> NAME/KEY: misc_feature
<222> LOCATION: (1)..(28)

<400> SEQUENCE: 19
cccgggaaga agagcgtgaa cgtgggat    28

<210> SEQ ID NO 20
<211> LENGTH: 32
<212> TYPE: DNA
<213> ORGANISM: Artificial
<220> FEATURE:
<223> OTHER INFORMATION: RT-PCR primer RC706 for PpSCL3 (EST 512)
<220> FEATURE:
<221> NAME/KEY: misc_feature
<222> LOCATION: (1)..(32)

<400> SEQUENCE: 20
agtactgcct taccaaatga gacaggtcct ca    32

<210> SEQ ID NO 21
<211> LENGTH: 5
<212> TYPE: PRT
<213> ORGANISM: Artificial
<220> FEATURE:
<223> OTHER INFORMATION: core of VHIID sequence motif
<220> FEATURE:
<221> NAME/KEY: MISC_FEATURE
<222> LOCATION: (1)..(5)

<400> SEQUENCE: 21

Val His Ile Ile Asp
1               5

<210> SEQ ID NO 22
<211> LENGTH: 5
<212> TYPE: PRT
<213> ORGANISM: Artificial
<220> FEATURE:
<223> OTHER INFORMATION: sequence motif
<220> FEATURE:
<221> NAME/KEY: MISC_FEATURE
<222> LOCATION: (1)..(5)

<400> SEQUENCE: 22

```
Pro Phe Tyr Arg Glu
1               5

<210> SEQ ID NO 23
<211> LENGTH: 6
<212> TYPE: PRT
<213> ORGANISM: Artificial
<220> FEATURE:
<223> OTHER INFORMATION: conserved sequence within VHIID motif
<220> FEATURE:
<221> NAME/KEY: MISC_FEATURE
<222> LOCATION: (1)..(6)

<400> SEQUENCE: 23

Pro Asn His Asp Gln Leu
1               5

<210> SEQ ID NO 24
<211> LENGTH: 5
<212> TYPE: PRT
<213> ORGANISM: Artificial
<220> FEATURE:
<223> OTHER INFORMATION: C-terminal portion of VHIID motif
<220> FEATURE:
<221> NAME/KEY: MISC_FEATURE
<222> LOCATION: (1)..(5)

<400> SEQUENCE: 24

Leu Arg Ile Thr Gly
1               5
```

SCARECROW-LIKE STRESS-RELATED POLYPEPTIDES AND METHODS OF USE IN PLANTS

CROSS-REFERENCE TO RELATED APPLICATIONS

This application is a divisional of allowed U.S. patent application Ser. No. 11/665,890, filed Apr. 19, 2007 and now U.S. Pat. No. 7,423,196, which is a National Phase application filed pursuant to 35 U.S.C. §371 of PCT/US2005/037478, filed Oct. 19, 2005, which claims the priority benefit of U.S. provisional patent application Ser. No. 60/620,601 filed Oct. 20, 2004, the entire contents of each of which are hereby incorporated by reference.

BACKGROUND OF THE INVENTION

1. Field of the Invention

This invention relates generally to nucleic acid sequences encoding polypeptides that are associated with growth and/or abiotic stress responses and/or abiotic stress tolerance in plants. In particular, this invention relates to nucleic acid sequences encoding polypeptides that increase plant growth under conditions of limited water availability and confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as soybean, rice, maize (corn), cotton, and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on development, growth, and yield of most crop plants are profound. Continuous exposure to drought conditions causes major alterations in the plant metabolism which ultimately lead to cell death and consequently yield losses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold, and salt tolerance in model drought- and/or salt-tolerant plants are complex in nature and involve multiple mechanisms of cellular adaptation and numerous metabolic pathways. This multi-component nature of stress tolerance has not only made breeding for tolerance largely unsuccessful, but has also limited the ability to genetically engineer stress tolerant plants using biotechnological methods.

Common damage from different stresses such as drought, salinity, and cold stress, appears to be mostly due to dehydration (Smirnoff, 1998, Curr. Opin. Biotech. 9:214-219). Drought (water stress)-tolerant and -sensitive plants can be clearly distinguished by the dramatic accumulation of ions and solutes in tolerant plants that leads to osmotic adjustments in the plants (Bohnert H. J and Jensen. R. G., 1996, TIBTECH 14:89-97). Drought and high salt conditions may correspond with mineral nutrition as a consequence of (1) reduced transport of ions through the soil to the roots; and/or (2) modified uptake of ions by the roots.

The SCARECROW (SCR) gene was identified in *Arabidopsis* and is expressed specifically in root progenitor tissues of plant embryos and in certain root and stem tissues. The SCR gene encodes a novel putative transcription factor and is required for asymmetric cell division in an *Arabidopsis* root. Modulation of SCR expression levels can be used to advantageously modify root and aerial structures of transgenic plants and enhance the agronomic properties of such plants. Mutation of the SCR gene results in a radial pattern defect and loss of a ground tissue layer in the root.

Pysh and co-workers identified a number of *Arabidopsis* expressed sequence tags (ESTs) that have similarity to the *Arabidopsis* SCR amino acid sequence and designated them the Scarecrow-like genes (SCL) (Pysh et al., 1999, Plant J. 18:111-119). The SCL genes comprise a novel gene family, referred to as the GRAS gene family, based on the locus designations of three genes: the gibberellin-acid insensitive (GAI) locus, the repressor of GAI (RGA) locus, and the scarecrow (SCR) locus. The GRAS/SCL gene products have been reported to be restricted to higher plants and are plant-specific proteins that participate in various developmental processes. Members of the GRAS/SCL family have a variable N-terminus and a highly conserved C-terminus that contains five recognizable motifs: the leucine heptad repeat I (LHR I), the VHIID motif, the leucine heptad repeat II (LHR II), the PFYRE motif, and the SAW motif.

The GRAS/SCL proteins function as transcription factors but are not restricted to their role in asymmetric cell division. For example, the PAT1 protein, has been shown to be involved in phytochrome A signal transduction of *Arabidopsis thaliana* (Bolle et al., Genes Dev., 2000, 14:1269-1278), and the tomato gene Lateral suppressor (Ls) functions in the formation of lateral branches. Two members of the GRAS family, the GAI and the RGA genes, play important roles in the gibberellin acid (GA) signal transduction pathway. *Arabidopsis* plants with a mutation at the GAI locus do not respond to exogenously applied GA and have a reduced stature (Koorneef et al., 1985, Physiol. Plant. 65:33-39). The SLR1 of rice has been identified as a GAI ortholog and has been demonstrated to be involved in the GA-signaling pathway in corn, rice, barley, grape, and wheat (Hynes et al., 2003, Transgenic Research 12:707-714). Overexpression of the *Arabidopsis* GAI in tobacco and rice produced a dwarf phenotype, as compared to a wild-type plant (Hynes et al., 2003, Transgenic Research 12:707-714).

There is a fundamental physiochemically-constrained trade-off, in all terrestrial photosynthetic organisms, between carbon dioxide ($CO_2$) absorption and water loss (Taiz and Zeiger, 1991, Plant Physiology, Benjamin/Cummings Publishing Co., p. 94). $CO_2$ needs to be in aqueous solution for the action of $CO_2$ fixation enzymes such as Rubisco (Ribulose 1,5-bisphosphate Carboxylase/Oxygenase) and PEPC (Phosphoenolpyruvate carboxylase). As a wet cell surface is required for $CO_2$ diffusion, evaporation will inevitably occur when the humidity is below 100% (Taiz and Zeiger, 1991, p. 257). Plants have numerous physiological mechanisms to reduce water loss (e.g. waxy cuticles, stomatal closure, leaf hairs, sunken stomatal pits). As these barriers do not discriminate between water and $CO_2$ flux, these water conservation measures will also act to increase resistance to $CO_2$ uptake (Kramer, 1983, Water Relations of Plants, Academic Press p.

305). Photosynthetic $CO_2$ uptake is absolutely required for plant growth and biomass accumulation in photoautotrophic plants.

Water Use Efficiency (WUE) is a parameter frequently used to estimate the trade off between water consumption and $CO_2$ uptake/growth (Kramer, 1983, Water Relations of Plants, Academic Press p. 405). WUE has been defined and measured in multiple ways. One approach is to calculate the ratio of whole plant dry weight, to the weight of water consumed by the plant throughout its life (Chu et al., 1992, Oecologia 89:580). Another variation is to use a shorter time interval when biomass accumulation and water use are measured (Mian et al., 1998, Crop Sci. 38:390). Another approach is to utilize measurements from restricted parts of the plant, for example, measuring only aerial growth and water use (Nienhuis et al 1994 Amer J Bot 81:943). WUE also has been defined as the ratio of $CO_2$ uptake to water vapor loss from a leaf or portion of a leaf, often measured over a very short time period (e.g. seconds/minutes) (Kramer, 1983, p. 406). The ratio of $^{13}C/^{12}C$ fixed in plant tissue, and measured with an isotope ratio mass-spectrometer, also has been used to estimate WUE in plants using $C_3$ photosynthesis (Martin et al., 1999, Crop Sci. 1775).

An increase in WUE is informative about the relatively improved efficiency of growth and water consumption, but this information taken alone does not indicate whether one of these two processes has changed or both have changed. In selecting traits for improving crops, an increase in WUE due to a decrease in water use, without a change in growth would have particular merit in an irrigated agricultural system where the water input costs were high. An increase in WUE driven mainly by an increase in growth without a corresponding jump in water use would have applicability to all agricultural systems. In many agricultural systems where water supply is not limiting, an increase in growth, even if it came at the expense of an increased water use (i.e. no change in WUE), could also increase yield. Therefore new methods to increase both WUE and biomass accumulation are required to improve agricultural productivity. As WUE integrates many physiological processes relating to primary metabolism and water use, it is typically a highly polygenic trait with a large genotype by environment interaction (Richards et al., 2002, Crop Sci. 42:111). For these and other reasons, few attempts to select for WUE changes in traditional breeding programs have been successful.

Although some genes that are involved in plant growth and/or stress responses in plants have been characterized, the characterization and cloning of plant genes that confer stress tolerance and/or increased growth under water-limited conditions remains largely incomplete and fragmented. For example, certain studies have indicated that drought and salt stress in some plants may be due to additive gene effects, in contrast to other research that indicates specific genes are transcriptionally activated in vegetative tissue of plants under osmotic stress conditions. Although it is generally assumed that stress-induced proteins have a role in stress tolerance, direct evidence is still lacking, and the functions of many stress-responsive genes are unknown.

There is a need, therefore, to identify additional genes expressed in stress tolerant plants and/or plants efficient in water use that have the capacity to confer stress resistance and or increased growth under water-limited conditions to the host plant and to other plant species. Newly generated stress tolerant plants and/or plants efficient in water use will have many advantages, such as increasing the range in which crop plants can be cultivated by, for example, decreasing the water requirements of a plant species. Plant and crop growth and yield is commonly limited by water availability. Increasing plant growth under conditions of limited water availability can increase crop yields in all the major global markets.

SUMMARY OF THE INVENTION

This invention fulfills in part the need to identify new, unique polypeptides and nucleic acids capable of increasing growth under water-limited conditions and/or conferring stress tolerance to plants upon modification of expression. The present invention describes a novel genus of Scarecrow-like Stress-Related Polypeptides (SLSRPs) and SLSRP coding nucleic acids that are important for plant growth and modulating a plant's response to an environmental stress. More particularly, modifying expression of these SLSRP coding nucleic acids in a plant results in the plant's increased growth under water-limited conditions and/or increased tolerance to an environmental stress.

Therefore, the present invention includes an isolated plant cell comprising an SLSRP coding nucleic acid, wherein expression of the nucleic acid sequence in the plant cell results in the plant's increased growth under water-limited conditions and/or increased tolerance to environmental stress as compared to a wild type variety of the plant cell. Preferably, the SLSRPs are from *Physcomitrella patens* or *Glycine max*. Namely, described herein are the *Physcomitrella patens* Scarecrow-like genes, PpSCL1 (SEQ ID NOs:1 and 2), PpSCL2 (SEQ ID NOs:3 and 4), PpSCL3 (SEQ ID NOs:5 and 6), and the *Glycine max* Scarecrow-like gene, GmSCL1 (SEQ ID NOs:7 and 8).

The invention provides in some embodiments that the SLSRPs and coding nucleic acids are those that are found in the genus *Physcomitrella* or *Glycine*. In another preferred embodiment, the nucleic acids and polypeptides are from a *Physcomitrella patens* plant or a *Glycine max* plant. In one embodiment, the invention provides that plants expressing the SLSRPs demonstrate an increase in growth under water-limited conditions. In another embodiment, the increase in plant growth is due to the plant's increase in Water Use Efficiency (WUE), as compared to a wild-type variety of the plant. In another embodiment, the invention provides that plants overexpressing the SLSRPs demonstrate increased plant Dry Weight (DW), as compared to a wild-type variety of the plant. In yet another embodiment, the invention provides that plants overexpressing the SLSRPs demonstrate increased tolerance to an environmental stress, as compared to a wild-type variety of the plant. The invention provides that the environmental stress can be salinity, drought, temperature, metal, chemical, pathogenic and oxidative stresses, or combinations thereof. In preferred embodiments, the environmental stress can be selected from one or more of the group consisting of drought, high salt, and low temperature.

The invention further provides seeds produced by transgenic plants transformed by SLSRP coding nucleic acids, wherein the seed comprises the SLSRP coding nucleic acid and wherein the plants are true breeding for increased growth under water-limited conditions and/or increased tolerance to an environmental stress as compared to a wild type variety of the plant. In a preferred embodiment, the invention provides seeds produced by a transgenic plant transformed with a PpSCL1, PpSCL2, PpSCL3, or GmSCL1 coding nucleic acid, wherein the plants are true breeding for increased growth under water-limited conditions and/or increased tolerance to an environmental stress as compared to a wild type variety of the plant.

The invention further provides an agricultural product produced by any of the below-described transgenic plants, plant parts, or seeds. The invention further provides isolated SLSRPs as described below. The invention further provides isolated SLSRP coding nucleic acids, wherein the SLSRP nucleic acid encodes an SLSRP as described below.

The invention further provides isolated recombinant expression vectors comprising SLSRP coding nucleic acids as described below, wherein expression of the vectors in a host cell results in increased growth under water-limited conditions and/or increased tolerance to an environmental stress as compared to a wild type variety of the host cell. The invention further provides host cells containing the vectors and plants containing the host cells.

The invention further provides methods of producing transgenic plants with an SLSRP coding nucleic acid, wherein expression of the nucleic acid in the plants results in increased growth under water-limited conditions and/or increased tolerance to an environmental stress as compared to a wild type variety of the plant comprising: (a) transforming a plant cell with an expression vector comprising an SLSRP coding nucleic acid, and (b) generating from the plant cell a transgenic plant with an increased growth under water-limited conditions and/or increased tolerance to an environmental stress as compared to a wild type variety of the plant. In a preferred embodiment, the SLSRPs and SLSRP coding nucleic acids are as described below.

The present invention further provides a method of identifying a novel SLSRP, comprising (a) raising a specific antibody response to an SLSRP, or fragment thereof, as described below; (b) screening putative SLSRP material with the antibody, wherein specific binding of the antibody to the material indicates the presence of a potentially novel SLSRP; and (c) identifying from the bound material a novel SLSRP in comparison to known SLSRPs. Alternatively, hybridization with nucleic acid probes as described below can be used to identify novel SLSRP coding nucleic acids.

The present invention also provides methods of modifying growth or stress tolerance of a plant comprising, modifying the expression of an SLSRP coding nucleic acid in the plant, wherein the SLSRP is as described below. The invention provides that this method can be performed such that the growth and/or stress tolerance is either increased or decreased. Preferably, growth and/or stress tolerance is increased in a plant via modifying expression of an SLSRP coding nucleic acid.

BRIEF DESCRIPTION OF THE DRAWINGS

FIG. 3 shows the detailed alignment of the disclosed PpSCL1, PpSCL2, PpSCL3, and GmSCL1 (SEQ ID NOs: 2, 4, 6, and 8) amino acid sequences with the sequences of six known members of the GRAS family. The alignment was generated using Align X of Vector NTI. White font on black is consensus residue derived from a block of similar residues at a given position. Black font on gray is consensus or similar amino acid at a position with a consensus of residues in at least 50% of the sequences. Non-similar residues at a given position are identified as black font on white.

DETAILED DESCRIPTION OF THE INVENTION

Figure 1:
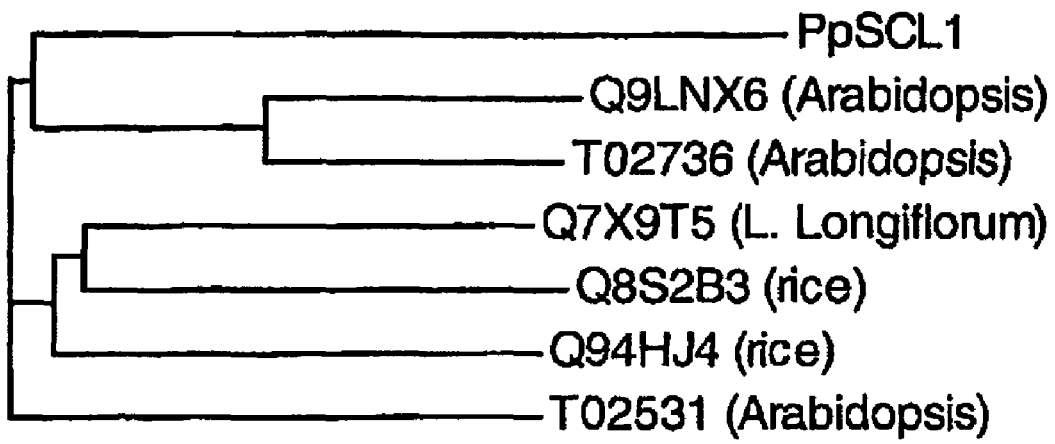
FIG. 1 shows the phylogenetic tree of the disclosed PpSCL1 (SEQ ID NO:2) amino acid sequence with sequences of six known members of the GRAS family. The diagram was generated using Align X of Vector NTI

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as "Scarecrow-Like Stress-Related Polypeptides," or "SLSRPs", in no way limits the functionality of those sequences.

The present invention describes a novel genus of SLSRPs and SLSRP coding nucleic acids that are important for increasing plant growth under water-limited conditions and/or modulating a plant's response to an environmental stress. More particularly, modifying expression of the SLSRP coding nucleic acids in a plant results in the plant's increased growth under water-limited conditions and/or increased tolerance to an environmental stress. A representative members of the SLSRP genus are PpSCL1 (SEQ ID NOs:1 and 2), PpSCL2 (SEQ ID NOs:3 and 4), PpSCL3 (SEQ ID NOs:5 and 6), and GmSCL1 (SEQ ID NOs:7 and 8).

Accordingly, the present invention encompasses SLSRP polynucleotides and polypeptides and their use for increasing a plant's growth under water-limited conditions and/or increasing the plant's tolerance to an environmental stress. In one embodiment, the SLSRPs are from a plant, preferably a *Physcomitrella* or *Glycine* plant, and more preferably a *Physcomitrella patens* or *Glycine max* plant. In another preferred embodiment, the SLSRPs are PpSCL1 as defined in SEQ ID NOs:1 and 2; PpSCL2 as defined in SEQ ID NOs:3 and 4; PpSCL3 as defined in SEQ ID NOs:5 and 6; or GmSCL1 as defined in SEQ ID NOs:7 and 8.

The disclosed SLSRP polypeptide sequences (SEQ ID NOs:2, 4, 6, and 8) have significant sequence homology to the sequence of known members of the GRAS family. For example, the PpSCL1 sequence has 42% sequence identity and 30% sequence similarity to the Q7X9T5 (*L. Longiflorum* SCL) protein sequence, 42% identity and 30% similarity to the Q8S2B3 (rice) protein sequence, 42% identity and 30% similarity to the T02531 (*Arabidopsis* scarecrow gene regulator) protein sequence, 39% identity and 27% similarity to the Q94HJ4 (rice putative scarecrow gene regulator) protein sequence, 21% identity and 15% similarity to the Q9LNX6 (*Arabidopsis*) protein sequence, and 24% identity and 16% similarity to the T02736 (*Arabidopsis* scarecrow gene regulator) protein sequence. The PpSCL2 sequence has 26% sequence identity and 39% sequence similarity to the NP190990 (*A. thaliana* scarecrow transcription factor, putative) protein sequence, 26% identity and 39% similarity to the T51244 (*A. thaliana* scrarecrow protein) protein sequence, 24% identity and 38% similarity to the Q6L5Z0 (*Oryza sativa* scarecrow) protein sequence, 24% identity and 38% similarity to the Q9FUZ7 (*Zea mays* scarecrow) protein sequence, and 20% identity and 31% similarity to the Q9AVK4 (*Pisum sativum* scarecrow) protein sequence. The PpSCL3 sequence has 40% sequence identity and 49% sequence similarity to the NP_199626 (*A. thaliana* phytochrome A signal transduction 1) protein sequence, 37% identity and 45% similarity to the Q8GYN7 (*A. thaliana* putative scrarecrow gene regulator) protein sequence, 42% identity and 54% similarity to the NP_175475 (*A. thaliana* scarecrow-like transcription factor 5) protein sequence, 40% identity and 51% similarity to the E966542 (*A. thaliana* scarecrow-like protein) protein sequence, and 41% identity and 54% similarity to the Q7EXH0 (*A. thaliana* putative scarecrow protein) protein sequence. The GmSCL1 sequence has 45% sequence identity and 58% sequence similarity to the NP_200064 (*A. thaliana* scarecrow-like transcription factor 8) protein sequence, 32% identity and 47% similarity to BAD27826 (*O. sativa* gibberellin-insensitive protein OsGAI) protein sequence, 28% identity and 40% similarity to NP_915059.1 (*O. sativa* scarecrow-like protein) protein sequence and 19% identity and 27% similarity to AF036300_1 (*A. thaliana* scarecrow-like 1) protein sequence.

The present invention provides a transgenic plant cell transformed by an SLSRP coding nucleic acid, wherein expression of the nucleic acid sequence in the plant cell results in increased growth under water-limited conditions and/or increased tolerance to an environmental stress as compared to a wild type variety of the plant cell. The invention further provides transgenic plant parts and transgenic plants containing the plant cells described herein. The term "plant" as used herein shall refer to whole plants, plant cells, and plant parts including seeds. Plant parts include, but are not limited to, stems, roots, ovules, stamens, leaves, embryos, meristematic regions, callus tissue, gametophytes, sporophytes, pollen, microspores, and the like. In one embodiment, the transgenic plant is male sterile. Also provided is a plant seed produced by a transgenic plant transformed by an SLSRP coding nucleic acid, wherein the seed contains the SLSRP coding nucleic acid, and wherein the plant is true breeding for increased growth under water-limited conditions and/or increased tolerance to an environmental stress as compared to a wild type variety of the plant. The invention further provides a seed produced by a transgenic plant expressing an SLSRP, wherein the seed contains the SLSRP, and wherein the plant is true breeding for increased growth under water-limited conditions and/or increased tolerance to an environmental stress as compared to a wild type variety of the plant. The invention also provides an agricultural product produced by any of the below-described transgenic plants, plant parts, and plant seeds. Agricultural products include, but are not limited to, plant extracts, proteins, amino acids, carbohydrates, fats, oils, polymers, vitamins, and the like.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety. As also used herein, the term "wild type variety" refers to a group of plants that are analyzed for comparative purposes as a control plant, wherein the wild type variety plant is identical to the test plant (plant transformed with an SLSRP or plant in which expression of the SLSRP coding nucleic acid has been modified) with the exception that the wild type variety plant has not been transformed with an SLSRP coding nucleic acid and/or expression of the SLSRP coding nucleic acid in the wild type variety plant has not been modified.

The present invention describes that *Physcomitrella patens* and *Glycine max* SLSRPs are useful for increasing a plant's growth under water-limited conditions and/or tolerance to environmental stress. As used herein, the term polypeptide refers to a chain of at least four amino acids joined by peptide bonds. The chain may be linear, branched, circular, or combinations thereof. Accordingly, the present invention provides isolated SLSRPs selected from PpSCL1, PpSCL2, PpSCL3, GmSCL1, and homologs thereof. In preferred embodiments, the SLSRPs are selected from PpSCL1 as defined in SEQ ID NO:2, PpSCL2 as defined in SEQ ID NO:4, PpSCL3 as defined in SEQ ID NO:6, GmSCL1 as defined in SEQ ID NO:8, and homologs and orthologs thereof. Homologs and orthologs of the amino acid sequences are defined below.

The SLSRPs of the present invention are preferably produced by recombinant DNA techniques. For example, a nucleic acid molecule encoding the polypeptide is cloned into an expression vector (as described below), the expression vector is introduced into a host cell (as described below) and the SLSRP is expressed in the host cell. The SLSRP can then be isolated from the cells by an appropriate purification scheme using standard polypeptide purification techniques. For the purposes of the invention, the term "recombinant polynucleotide" refers to a polynucleotide that has been altered, rearranged, or modified by genetic engineering. Examples include any cloned polynucleotide, and polynucleotides that are linked or joined to heterologous sequences. The term "recombinant" does not refer to alterations to polynucleotides that result from naturally occurring events, such as spontaneous mutations. Alternative to recombinant expression, an SLSRP, or peptide thereof, can be synthesized chemically using standard peptide synthesis techniques. Moreover, native SLSRPs can be isolated from cells (e.g., *Physcomitrella patens* and *Glycine max* cells), for example using an anti-SLSRP antibody, which can be produced by standard techniques utilizing an SLSRP or fragment thereof.

As used herein, the term "environmental stress" refers to sub-optimal conditions associated with salinity, drought, temperature, metal, chemical, pathogenic and oxidative stresses, or combinations thereof. In preferred embodiments, the environmental stress can be selected from one or more of the group consisting of salinity, drought, or temperature, or combinations thereof, and in particular, can be selected from one or more of the group consisting of high salinity, low water content, or low temperature. As also used herein, the term "water use efficiency" refers to the amount of organic matter produced by a plant divided by the amount of water used by the plant in producing it, i.e. the dry weight of a plant in relation to the plant's water use. As used herein, the term "dry weight" refers to everything in the plant other than water, and includes, for example, carbohydrates, proteins, oils, and mineral nutrients. It is also to be understood that as used in the specification and in the claims, "a" or "an" can mean one or more, depending upon the context in which it is used. Thus, for example, reference to "a cell" can mean that at least one cell can be utilized.

As also used herein, the term "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine, and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR, and in vitro or in vivo transcription.

An "isolated" nucleic acid molecule is one that is substantially separated from other nucleic acid molecules, which are present in the natural source of the nucleic acid (i.e., sequences encoding other polypeptides). Preferably, an "isolated" nucleic acid is free of some of the sequences, which naturally flank the nucleic acid (i.e. sequences located at the 5' and 3' ends of the nucleic acid) in its naturally occurring replicon. For example, a cloned nucleic acid is considered isolated. In various embodiments, the isolated SLSRP nucleic acid molecule can contain less than about 5 kb, 4 kb, 3 kb, 2 kb, 1 kb, 0.5 kb, or 0.1 kb of nucleotide sequences which naturally flank the nucleic acid molecule in genomic DNA of the cell from which the nucleic acid is derived (e.g., a *Physcomitrella patens* and *Glycine max* cell). A nucleic acid is also considered isolated if it has been altered by human intervention, or placed in a locus or location that is not its natural site, or if it is introduced into a cell by agroinfection. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule having a nucleotide sequence of SEQ ID NO:1, SEQ ID NO:3, SEQ ID NO:5, SEQ ID NO:7, or a portion thereof, can be isolated using standard molecular biology techniques and the sequence information provided herein. For example, *P. patens* SLSRP cDNAs can be isolated from a *P. patens* library using all or portion of SEQ ID NO:1, SEQ ID NO:3, SEQ ID NO:5. Moreover, a nucleic acid molecule encompassing all or a portion of the sequence of SEQ ID NO:1, SEQ ID NO:3, SEQ ID NO:5, or SEQ ID NO:7 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979, Biochemistry 18: 5294-5299), and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1, SEQ ID NO:3, SEQ ID NO:5, or SEQ ID NO:7. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to an SLSRP nucleotide sequence can be prepared by standard synthetic techniques, e.g., using an automated DNA synthesizer.

In a preferred embodiment, an isolated nucleic acid molecule of the invention comprises the nucleotide sequence shown in SEQ ID NO:1, SEQ ID NO:3, SEQ ID NO:5, or SEQ ID NO:7. The cDNAs may comprise sequences encoding the SLSRP, (i.e., the "coding region"), as well as 5' untranslated sequences and 3' untranslated sequences. It is to be understood that SEQ ID NO:1, SEQ ID NO:3, SEQ ID NO:5, or SEQ ID NO:7 comprises only the coding region of the SLSRP nucleotide sequence. Alternatively, the nucleic acid molecules of the present invention can comprise whole genomic fragments isolated from genomic DNA. The present invention also includes SLSRP coding nucleic acids that encode the SLSRPs as described herein. Preferred is an SLSRP coding nucleic acid that encodes PpSCL1 as defined in SEQ ID NO:2, PpSCL2 as defined in SEQ ID NO:4, PpSCL3 as defined in SEQ ID NO:6, or GmSCL1 as defined in SEQ ID NO:8.

Moreover, the nucleic acid molecule of the invention can comprise a portion of the coding region of the sequence shown in SEQ ID NO:1, SEQ ID NO:3, SEQ ID NO:5, or SEQ ID NO:7, for example, a fragment that can be used as a probe or primer or a fragment encoding a biologically active portion of an SLSRP. The nucleotide sequence determined from the cloning of an SLSRP gene from *P. patens* and *G. max* allows for the generation of probes and primers designed for use in identifying and/or cloning SLSRP homologs in other cell types and organisms, as well as SLSRP homologs from other mosses and related species. The portion of the coding region can also encode a biologically active fragment of an SLSRP.

As used herein, the term "biologically active portion of" an SLSRP is intended to include a portion, e.g., a domain/motif, of an SLSRP that participates in growth of a plant and/or modulation of stress tolerance in a plant. The stress tolerance is preferably drought tolerance, freeze tolerance, or salt tolerance. For the purposes of the present invention, the term "increased growth" of a transgenic plant comprising the SLSRP expression cassette (or expression vector) refers to at least a 10%, 15%, 20%, 25% or 30%, preferably at least 40%, 45%, 50%, 55% or 60%, more preferably at least 65%, 70%, 75%, 80%, 85%, 90%, 95% or more increase in Water Use Efficiency (WUE) and/or plant Dry Weight (DW) as compared to a non-transgenic or transgenic vector-only control plant. The modulation of stress tolerance refers to at least a 10%, 15%, 20%, 25% or 30%, preferably at least 40%, 45%, 50%, 55% or 60%, more preferably at least 65%, 70%, 75%, 80%, 85%, 90%, 95% or more increase or decrease in the stress tolerance of a transgenic plant comprising an SLSRP expression cassette (or expression vector) as compared to the stress tolerance of a non-transgenic control plant. Methods for quantitating plant growth and stress tolerance are provided at least in Example 7 below. In a preferred embodiment, the biologically active portion of an SLSRP increases a plant's growth under water-limited conditions and/or increases the plant's tolerance to an environmental stress.

Biologically active portions of an SLSRP include peptides comprising amino acid sequence derived from the amino acid sequence of an SLSRP, e.g., an amino acid sequence of SEQ ID NO:2, SEQ ID NO:4, SEQ ID NO:6, SEQ ID NO:8, or the amino acid sequence of a polypeptide identical to an SLSRP, which include fewer amino acids than a full length SLSRP or the full length polypeptide which is identical to an SLSRP, and exhibit at least one activity of an SLSRP. Typically, biologically active portions (e.g., peptides which are, for example, 5, 10, 15, 20, 30, 35, 36, 37, 38, 39, 40, 50, 100, or more amino acids in length) comprise a domain or motif with at least one activity of an SLSRP. Moreover, other biologically active portions in which other regions of the polypeptide are deleted, can be prepared by recombinant techniques and evaluated for one or more of the activities described herein. Preferably, the biologically active portions of an SLSRP include one or more selected sequence motifs or portions thereof having biological activity such as the LHR I, LHR II, VHIID (SEQ ID NO:21), PFYRE (SEQ ID NO:22), and SAW motifs. The LHR I and II motifs are leucine hepad repeats, and the VHIID (SEQ ID NO:21) motif contains the VHIID (SEQ ID NO:21) sequence that is readily recognizable in all members of the GRAS family. Within the VHIID (SEQ ID NO:21) motif, the P-N-H-D-Q-L (SEQ ID NO:23) residues are absolutely conserved. The spacing between the proline and asparagine residues is identical among all GRAS members, as is the spacing between the histidine, aspartate, glutamine, and leucine residues. The VIIID (SEQ ID NO:21) motif is bound at its C-terminus by a conserved sequence referred to as LRITG (SEQ ID NO:24). The PFYRE (SEQ ID NO:22) motif is not as well conserved at the sequence level (only the P is absolutely conserved). Within the PFYRE (SEQ ID NO:22) motif, the sequences are largely co-linear, and portions of this region show a high degree of sequence similarity among all members of the GRAS family. The SAW motif is characterized by three pairs of absolutely conserved residues: R-E, W-G, and W-W. The W-W pair is nearly at the C-terminus shows absolute conservation of spacing, as does the W-G pair; however, the spacing between the W-G and W-W pairs is not conserved.

In one embodiment, the present invention provides SLSRPs that have a scarecrow-like domain comprising the three most conserved motifs: the VHIID motif, the PFYRE motif, and the SAW motif. In another embodiment, the conserved scarecrow-like domain comprises at least one of the following four conserved regions.

The present invention includes homologs and analogs of naturally occurring SLSRPs and SLSRP encoding nucleic acids in a plant. "Homologs" are defined herein as two nucleic acids or polypeptides that have similar, or "identical," nucleotide or amino acid sequences, respectively. Homologs include allelic variants, orthologs, paralogs, agonists, and antagonists of SLSRPs as defined hereafter. The term "homolog" further encompasses nucleic acid molecules that differ from one of the nucleotide sequences shown in SEQ ID NO:1, SEQ ID NO:3, SEQ ID NO:5, or SEQ ID NO:7 (and portions thereof) due to degeneracy of the genetic code and thus encode the same SLSRP as that encoded by the nucleotide sequences shown in SEQ ID NO:1, SEQ ID NO:3, SEQ ID NO:5, or SEQ ID NO:7. As used herein, a "naturally occurring" SLSRP refers to an amino acid sequence that occurs in nature. Preferably, a naturally occurring SLSRP comprises an amino acid sequence of SEQ ID NO:2, SEQ ID NO:4, SEQ ID NO:6, or SEQ ID NO:8.

An agonist of the SLSRP can retain substantially the same, or a subset, of the biological activities of the SLSRP. An antagonist of the SLSRP can inhibit one or more of the activities of the naturally occurring form of the SLSRP.

Nucleic acid molecules corresponding to natural allelic variants and analogs, orthologs, and paralogs of an SLSRP cDNA can be isolated based on their identity to the *Physcomitrella patens* and *Glycine max* SLSRP nucleic acids described herein using SLSRP cDNAs, or a portion thereof, as a hybridization probe according to standard hybridization techniques under stringent hybridization conditions. In an alternative embodiment, homologs of the SLSRP can be identified by screening combinatorial libraries of mutants, e.g., truncation mutants, of the SLSRP for SLSRP agonist or antagonist activity. In one embodiment, a variegated library of SLSRP variants is generated by combinatorial mutagenesis at the nucleic acid level and is encoded by a variegated gene library. A variegated library of SLSRP variants can be produced by, for example, enzymatically ligating a mixture of synthetic oligonucleotides into gene sequences such that a degenerate set of potential SLSRP sequences is expressible as individual polypeptides, or alternatively, as a set of larger fusion polypeptides (e.g., for phage display) containing the set of SLSRP sequences therein. There are a variety of methods that can be used to produce libraries of potential SLSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential SLSRP sequences. Methods for synthesizing degenerate oligonucleotides are known in the art (See, e.g., Narang, 1983, Tetrahedron 39:3; Itakura et al., 1984, Annu. Rev. Biochem. 53:323; Itakura et al., 1984, Science 198:1056; Ike et al., 1983, Nucleic Acid Res. 11:477).

In addition, libraries of fragments of the SLSRP coding regions can be used to generate a variegated population of SLSRP fragments for screening and subsequent selection of homologs of an SLSRP. In one embodiment, a library of coding sequence fragments can be generated by treating a double stranded PCR fragment of an SLSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal, and internal fragments of various sizes of the SLSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of GAS/SCL homologs.

The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify SLSRP homologs (Arkin and Yourvan, 1992, PNAS 89:7811-7815; Delgrave et al., 1993, Polypeptide Engineering 6(3):327-331). In another embodiment, cell based assays can be exploited to analyze a variegated SLSRP library, using methods well known in the art. The present invention further provides a method of identifying a novel SLSRP, comprising (a) raising a specific antibody response to an SLSRP, or a fragment thereof, as described herein; (b) screening putative SLSRP material with the antibody, wherein specific binding of the antibody to the material indicates the presence of a potentially novel SLSRP; and (c) analyzing the bound material in comparison to known SLSRP, to determine its novelty.

As stated above, the present invention includes SLSRPs and homologs thereof. To determine the percent sequence identity of two amino acid sequences (e.g., the sequence of SEQ ID NO:2, SEQ ID NO:4, SEQ ID NO:6, SEQ ID NO:8, and a mutant form thereof), the sequences are aligned for optimal comparison purposes (e.g., gaps can be introduced in the sequence of one polypeptide for optimal alignment with the other polypeptide or nucleic acid). The amino acid residues at corresponding amino acid positions are then compared. When a position in one sequence (e.g., the sequence of SEQ ID NO:2, SEQ ID NO:4, SEQ ID NO:6, or SEQ ID NO:8) is occupied by the same amino acid residue as the corresponding position in the other sequence (e.g., a mutant form of the sequence of SEQ ID NO:2, SEQ ID NO:4, SEQ ID NO:6, or SEQ ID NO:8), then the molecules are identical at that position. The same type of comparison can be made between two nucleic acid sequences.

The percent sequence identity between the two sequences is a function of the number of identical positions shared by the sequences (i.e., percent sequence identity=numbers of identical positions/total numbers of positions×100). Preferably, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence shown in SEQ ID NO:2, SEQ ID NO:4, SEQ ID NO:6, or SEQ ID NO:8. In yet another embodiment, the isolated amino acid homologs included in the present invention are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to an entire amino acid sequence encoded by a nucleic acid sequence shown in SEQ ID NO:1, SEQ ID NO:3, SEQ ID NO:5, or SEQ ID NO:7. In other embodiments, the SLSRP amino acid homologs have sequence identity over at least 15 contiguous amino acid residues, more preferably at least 25 contiguous amino acid residues, and most preferably at least 35 contiguous amino acid residues of SEQ ID NO:2, SEQ ID NO:4, SEQ ID NO:6, or SEQ ID NO:8.

In another preferred embodiment, an isolated nucleic acid homolog of the invention comprises a nucleotide sequence which is at least about 40-60%, preferably at least about 60-70%, more preferably at least about 70-75%, 75-80%, 80-85%, 85-90%, or 90-95%, and even more preferably at least about 95%, 96%, 97%, 98%, 99%, or more identical to a nucleotide sequence shown in SEQ ID NO:1, SEQ ID NO:3, SEQ ID NO:5, or SEQ ID NO:7, or to a portion comprising at least 60 consecutive nucleotides thereof. The preferable length of sequence comparison for nucleic acids is at least 75 nucleotides, more preferably at least 100 nucleotides, and most preferably the entire length of the coding region. It is even more preferable that the nucleic acid homologs encode proteins having homology with SEQ ID NO:2, SEQ ID NO:4, SEQ ID NO:6, or SEQ ID NO:8 over the C-terminus that encodes five recognizable motifs as described above.

It is further preferred that the isolated nucleic acid homolog of the invention encodes an SLSRP, or portion thereof, that is at least 70% identical to an amino acid sequence of SEQ ID NO:2, SEQ ID NO:4, SEQ ID NO:6, or SEQ ID NO: 8 and that functions as a modulator of an environmental stress response in a plant. In a more preferred embodiment, modifying expression of the nucleic acid homolog in a plant increases growth and the tolerance of the plant to an environmental stress.

For the purposes of the invention, the percent sequence identity between two nucleic acid or polypeptide sequences is determined using the Vector NTI 9.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings. For purposes of a multiple alignment (Clustal W algorithm), the gap opening penalty is 10, and the gap extension penalty is 0.05 with blosum62 matrix. It is to be understood that for the purposes of determining sequence identity when comparing a DNA sequence to an RNA sequence, a thymidine nucleotide is equivalent to a uracil nucleotide.

In another aspect, the invention provides an isolated nucleic acid comprising a polynucleotide that hybridizes to the polynucleotide of SEQ ID NO:1, SEQ ID NO:3, SEQ ID NO:5, or SEQ ID NO:7 under stringent conditions. More particularly, an isolated nucleic acid molecule of the invention is at least 15 nucleotides in length and hybridizes under stringent conditions to the nucleic acid molecule comprising a nucleotide sequence of SEQ ID NO:1, SEQ ID NO:3, SEQ ID NO:5, or SEQ ID NO:7. In other embodiments, the nucleic acid is at least 30, 50, 100, 250, or more nucleotides in length. Preferably, an isolated nucleic acid homolog of the invention comprises a nucleotide sequence which hybridizes under highly stringent conditions to the nucleotide sequence shown in SEQ ID NO:1, SEQ ID NO:3, SEQ ID NO:5, or SEQ ID NO:7, and functions as a modulator of stress tolerance in a plant. In a further preferred embodiment, overexpression of the isolated nucleic acid homolog in a plant increases a plant's growth and tolerance to an environmental stress.

As used herein with regard to hybridization for DNA to a DNA blot, the term "stringent conditions" refers to hybridization overnight at 60° C. in 10× Denhart's solution, 6×SSC, 0.5% SDS, and 100 µg/ml denatured salmon sperm DNA. Blots are washed sequentially at 62° C. for 30 minutes each time in 3×SSC/0.1% SDS, followed by 1×SSC/0.1% SDS, and finally 0.1×SSC/0.1% SDS. In another embodiment, "stringent conditions" refers to hybridization in a 6×SSC solution at 65° C. As also used herein, "highly stringent conditions" refers to hybridization overnight at 65° C. in 10× Denharts solution, 6×SSC, 0.5% SDS, and 100 µg/ml denatured salmon sperm DNA. Blots are washed sequentially at 65° C. for 30 minutes each time in 3×SSC/0.1% SDS, followed by 1×SSC/0.1% SDS, and finally 0.1×SSC/0.1% SDS. Methods for nucleic acid hybridizations are described in Meinkoth and Wahl, 1984, Anal. Biochem. 138: 267-284; Current Protocols in Molecular Biology, Chapter 2, Ausubel et al. Eds., Greene Publishing and Wiley-Interscience, New York, 1995; and Tijssen, 1993, Laboratory Techniques in Biochemistry and Molecular Biology: Hybridization with Nucleic Acid Probes, Part I, Chapter 2, Elsevier, New York, 1993. Preferably, an isolated nucleic acid molecule of the invention that hybridizes under stringent or highly stringent conditions to a sequence of SEQ ID NO:1, SEQ ID NO:3, SEQ ID NO:5, or SEQ ID NO:7 corresponds to a naturally occurring nucleic acid molecule. As used herein, a "naturally occurring" nucleic acid molecule refers to an RNA or DNA molecule having a nucleotide sequence that occurs in nature (e.g., encodes a natural polypeptide). In one embodiment, the nucleic acid encodes a naturally occurring *Physcomitrella patens* SLSRP.

Using the above-described methods, and others known to those of skill in the art, one of ordinary skill in the art can isolate homologs of the SLSRPs comprising amino acid sequences shown in SEQ ID NO:2, SEQ ID NO:4, SEQ ID NO:6, or SEQ ID NO:8. One subset of these homologs is allelic variants. As used herein, the term "allelic variant" refers to a nucleotide sequence containing polymorphisms that lead to changes in the amino acid sequences of an SLSRP and that exist within a natural population (e.g., a plant species or variety). Such natural allelic variations can typically result in 1-5% variance in an SLSRP nucleic acid. Allelic variants can be identified by sequencing the nucleic acid sequence of interest in a number of different plants, which can be readily carried out by using hybridization probes to identify the same SLSRP genetic locus in those plants. Any and all such nucleic acid variations and resulting amino acid polymorphisms or variations in an SLSRP that are the result of natural allelic variation and that do not alter the functional activity of an SLSRP, are intended to be within the scope of the invention.

Moreover, nucleic acid molecules encoding SLSRPs from the same or other species such as SLSRP analogs, orthologs, and paralogs, are intended to be within the scope of the present invention. As used herein, the term "analogs" refers to two nucleic acids that have the same or similar function, but that have evolved separately in unrelated organisms. As used herein, the term "orthologs" refers to two nucleic acids from different species, but that have evolved from a common ancestral gene by speciation. Normally, orthologs encode polypeptides having the same or similar functions. As also used herein, the term "paralogs" refers to two nucleic acids that are related by duplication within a genome. Paralogs usually have different functions, but these functions may be related (Tatusov et al., 1997, Science 278(5338): 631-637). Analogs, orthologs, and paralogs of a naturally occurring SLSRP can differ from the naturally occurring SLSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably, 85-90% or 90-95%, and most preferably 95%, 96%, 97%, 98%, or even 99% identity, or 100% sequence identity, with all or part of a naturally occurring SLSRP amino acid sequence, and will exhibit a function similar to an SLSRP. Preferably, an SLSRP ortholog increases the growth and stress tolerance of a plant.

In addition to naturally-occurring variants of an SLSRP sequence that may exist in the population, the skilled artisan will further appreciate that changes can be introduced by mutation into a nucleotide sequence of SEQ ID NO:1, SEQ ID NO:3, SEQ ID NO:5, or SEQ ID NO:7, thereby leading to changes in the amino acid sequence of the encoded SLSRP, without altering the functional activity of the SLSRP. For example, nucleotide substitutions leading to amino acid substitutions at "non-essential" amino acid residues can be made in a sequence of SEQ ID NO:1, SEQ ID NO:3, SEQ ID NO:5, or SEQ ID NO:7. A "non-essential" amino acid residue is a residue that can be altered from the wild-type sequence of one of the SLSRPs without altering the activity of said SLSRP, whereas an "essential" amino acid residue is required for SLSRP activity. Other amino acid residues, however, (e.g., those that are not conserved or only semi-conserved in the domain having SLSRP activity) may not be essential for activity and thus are likely to be amenable to alteration without altering SLSRP activity.

Accordingly, another aspect of the invention pertains to nucleic acid molecules encoding SLSRPs that contain changes in amino acid residues that are not essential for SLSRP activity. Such SLSRPs differ in amino acid sequence from a sequence contained in SEQ ID NO:2, SEQ ID NO:4, SEQ ID NO:6, or SEQ ID NO:8, yet retain at least one of the SLSRP activities described herein. In one embodiment, the isolated nucleic acid molecule comprises a nucleotide sequence encoding a polypeptide, wherein the polypeptide comprises an amino acid sequence at least about 50% identical to an amino acid sequence of SEQ ID NO:2, SEQ ID NO:4, SEQ ID NO:6, or SEQ ID NO:8. Preferably, the polypeptide encoded by the nucleic acid molecule is at least about 50-60% identical to the sequence of SEQ ID NO:2, more preferably at least about 60-70% identical to the sequence of SEQ ID NO:2, SEQ ID NO:4, SEQ ID NO:6, or SEQ ID NO:8, even more preferably at least about 70-75%, 75-80%, 80-85%, 85-90%, or 90-95% identical to the sequence of SEQ ID NO:2, SEQ ID NO:4, SEQ ID NO:6, or SEQ ID NO:8, and most preferably at least about 96%, 97%, 98%, or 99% identical to the sequence of SEQ ID NO:2, SEQ ID NO:4, SEQ ID NO:6, or SEQ ID NO:8. The preferred SLSRP homologs of the present invention preferably participate in a plant's growth and stress tolerance response, or more particularly, participate in the transcription of a polypeptide involved in a plant's growth and stress tolerance response, and/or function as a transcription factor.

An isolated nucleic acid molecule encoding an SLSRP having sequence identity with a polypeptide sequence of SEQ ID NO:2, SEQ ID NO:4, SEQ ID NO:6, or SEQ ID NO:8 can be created by introducing one or more nucleotide substitutions, additions or deletions into a nucleotide sequence of SEQ ID NO:1, SEQ ID NO:3, SEQ ID NO:5, or SEQ ID NO:7, such that one or more amino acid substitutions, additions, or deletions are introduced into the encoded polypeptide. Mutations can be introduced into one of the sequences of SEQ ID NO: 1, SEQ ID NO:3, SEQ ID NO:5, or SEQ ID NO:7 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine). Thus, a predicted nonessential amino acid residue in an SLSRP is preferably replaced with another amino acid residue from the same side chain family. Alternatively, in another embodiment, mutations can be introduced randomly along all or part of an SLSRP coding sequence, such as by saturation mutagenesis, and the resultant mutants can be screened for an SLSRP activity described herein to identify mutants that retain SLSRP activity. Following mutagenesis of the sequence of SEQ ID NO:1, SEQ ID NO:3, SEQ ID NO:5, or SEQ ID NO:7, the encoded polypeptide can be expressed recombinantly and the activity of the polypeptide can be determined by analyzing the growth and stress tolerance of a plant expressing the polypeptide as described in Example 7.

Additionally, optimized SLSRP nucleic acids can be created. Preferably, an optimized SLSRP nucleic acid encodes an SLSRP that binds to a phosphate group and/or modulates a plant's tolerance to an environmental stress, and more preferably increases a plant's growth and tolerance to an environmental stress upon its overexpression in the plant. As used herein, "optimized" refers to a nucleic acid that is genetically engineered to increase its expression in a given plant or animal. To provide plant optimized SLSRP nucleic acids, the DNA sequence of the gene can be modified to: 1) comprise codons preferred by highly expressed plant genes; 2) comprise an A+T content in nucleotide base composition to that substantially found in plants; 3) form a plant initiation sequence; or 4) to eliminate sequences that cause destabilization, inappropriate polyadenylation, degradation and termination of RNA, or that form secondary structure hairpins or RNA splice sites. Increased expression of SLSRP nucleic acids in plants can be achieved by utilizing the distribution frequency of codon usage in plants in general or in a particular plant. Methods for optimizing nucleic acid expression in plants can be found in EPA 0359472; EPA 0385962; PCT Application No. WO 91/16432; U.S. Pat. No. 5,380,831; U.S. Pat. No. 5,436,391; Perlack et al., 1991, Proc. Natl. Acad. Sci. USA 88: 3324-3328; and Murray et al., 1989, Nucleic Acids Res. 17: 477-498.

An SLSRP nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized SLSRP nucleic acids of this invention also preferably have CG and TA doublet avoidance indices closely approximating those of the chosen host plant. More preferably these indices deviate from that of the host by no more than about 10-15%.

In addition to the nucleic acid molecules encoding the SLSRPs described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation, and/or stability of the target polynucleotide. Methods are described in the prior art for targeting the antisense polynucleotide to the chromosomal DNA, to a primary RNA transcript, or to a processed mRNA. Preferably, the target regions include splice sites, translation initiation codons, translation termination codons, and other sequences within the open reading frame.

The term "antisense," for the purposes of the invention, refers to a nucleic acid comprising a polynucleotide that is sufficiently complementary to all or a portion of a gene, primary transcript, or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide of SEQ ID NO:2, SEQ ID NO:4, SEQ ID NO:6, or SEQ ID NO:8.

The antisense nucleic acid can be complementary to an entire SLSRP coding strand, or to only a portion thereof. In one embodiment, an antisense nucleic acid molecule is antisense to a "coding region" of the coding strand of a nucleotide sequence encoding an SLSRP. The term "coding region" refers to the region of the nucleotide sequence comprising codons that are translated into amino acid residues. In another embodiment, the antisense nucleic acid molecule is antisense to a "noncoding region" of the coding strand of a nucleotide sequence encoding an SLSRP. The term "noncoding region" refers to 5' and 3' sequences that flank the coding region that are not translated into amino acids (i.e., also referred to as 5' and 3' untranslated regions). The antisense nucleic acid molecule can be complementary to the entire coding region of SLSRP mRNA, but more preferably is an oligonucleotide that is antisense to only a portion of the coding or noncoding region of SLSRP mRNA. For example, the antisense oligonucleotide can be complementary to the region surrounding the translation start site of SLSRP mRNA. An antisense oligonucleotide can be, for example, about 5, 10, 15, 20, 25, 30, 35, 40, 45, or 50 nucleotides in length. Typically, the antisense molecules of the present invention comprise an RNA having 60-100% sequence identity with at least 14 consecutive nucleotides of SEQ ID NO:1, SEQ ID NO:3, SEQ ID NO:5, or SEQ ID NO:7, or a polynucleotide encoding a polypeptide of SEQ ID NO:2, SEQ ID NO:4, SEQ ID NO:6, or SEQ ID NO:8. Preferably, the sequence identity will be at least 70%, more preferably at least 75%, 80%, 85%, 90%, 95%, or 98%, and most preferably 99%.

The antisense nucleic acid molecules of the invention are typically administered to a cell or generated in situ such that they hybridize with or bind to cellular mRNA and/or genomic DNA encoding an SLSRP to thereby inhibit expression of the polypeptide, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

As an alternative to antisense polynucleotides, ribozymes, sense polynucleotides, or double stranded RNA (dsRNA) can be used to reduce expression of an SLSRP polypeptide. As used herein, the term "ribozyme" refers to a catalytic RNA-based enzyme with ribonuclease activity that is capable of cleaving a single-stranded nucleic acid, such as an mRNA, to which it has a complementary region. Ribozymes (e.g., hammerhead ribozymes described in Haselhoff and Gerlach, 1988, Nature 334:585-591) can be used to catalytically cleave SLSRP mRNA transcripts to thereby inhibit translation of SLSRP mRNA. A ribozyme having specificity for an SLSRP-encoding nucleic acid can be designed based upon the nucleotide sequence of an SLSRP cDNA, as disclosed herein (i.e., SEQ ID NO:1, SEQ ID NO:3, SEQ ID NO:5, or SEQ ID NO:7) or on the basis of a heterologous sequence to be isolated according to methods taught in this invention. For example, a derivative of a Tetrahymena L-19 IVS RNA can be constructed in which the nucleotide sequence of the active site is complementary to the nucleotide sequence to be cleaved in an SLSRP-encoding mRNA. See, e.g., U.S. Pat. Nos. 4,987,071 and 5,116,742 to Cech et al. Alternatively, SLSRP mRNA can be used to select a catalytic RNA having a specific ribonuclease activity from a pool of RNA molecules. See, e.g., Bartel and Szostak, 1993, Science 261: 1411-1418. In preferred embodiments, the ribozyme will contain a portion having at least 7, 8, 9, 10, 12, 14, 16, 18, or 20 nucleotides, and more preferably 7 or 8 nucleotides, that have 100% complementarity to a portion of the target RNA. Methods for making ribozymes are known to those skilled in the art. See, e.g., U.S. Pat. Nos. 6,025,167; 5,773,260; and 5,496,698.

The term "dsRNA," as used herein, refers to RNA hybrids comprising two strands of RNA. The dsRNAs can be linear or circular in structure. In a preferred embodiment, dsRNA is specific for a polynucleotide encoding either the polypeptide of SEQ ID NO:2, SEQ ID NO:4, SEQ ID NO:6, or SEQ ID NO:8, or a polypeptide having at least 80% sequence identity with a polypeptide of SEQ ID NO:2, SEQ ID NO:4, SEQ ID NO:6, or SEQ ID NO:8. The hybridizing RNAs may be substantially or completely complementary. By "substantially complementary," it is meant that when the two hybridizing RNAs are optimally aligned using the BLAST program as described above, the hybridizing portions are at least 95% complementary. Preferably, the dsRNA will be at least 100 base pairs in length. Typically, the hybridizing RNAs will be of identical length with no over hanging 5' or 3' ends and no gaps. However, dsRNAs having 5' or 3' overhangs of up to 100 nucleotides may be used in the methods of the invention.

The dsRNA may comprise ribonucleotides, ribonucleotide analogs such as 2'-O-methyl ribosyl residues, or combinations thereof. See, e.g., U.S. Pat. Nos. 4,130,641 and 4,024,222. A dsRNA polyriboinosinic acid:polyribocytidylic acid is described in U.S. Pat. No. 4,283,393. Methods for making and using dsRNA are known in the art. One method comprises the simultaneous transcription of two complementary DNA strands, either in vivo, or in a single in vitro reaction mixture. See, e.g., U.S. Pat. No. 5,795,715. In one embodiment, dsRNA can be introduced into a plant or plant cell directly by standard transformation procedures. Alternatively, dsRNA can be expressed in a plant cell by transcribing two complementary RNAs.

Other methods for the inhibition of endogenous gene expression, such as triple helix formation (Moser et al., 1987, Science 238: 645-650 and Cooney et al., 1988, Science 241: 456-459) and co-suppression (Napoli et al., 1990, The Plant Cell 2:279-289) are known in the art. Partial and full-length cDNAs have been used for the co-suppression of endogenous plant genes. See, e.g., U.S. Pat. Nos. 4,801,340, 5,034,323, 5,231,020, and 5,283,184; Van der Kroll et al., 1990, The Plant Cell 2:291-299; Smith et al., 1990, Mol. Gen. Genetics 224:477-481; and Napoli et al., 1990, The Plant Cell 2:279-289.

For sense suppression, it is believed that introduction of a sense polynucleotide blocks transcription of the corresponding target gene. The sense polynucleotide will have at least 65% sequence identity with the target plant gene or RNA. Preferably, the percent identity is at least 80%, 90%, 95%, or more. The introduced sense polynucleotide need not be full length relative to the target gene or transcript. Preferably, the sense polynucleotide will have at least 65% sequence identity with at least 100 consecutive nucleotides of SEQ ID NO:1, SEQ ID NO:3, SEQ ID NO:5, or SEQ ID NO:7. The regions of identity can comprise introns and/or exons and untranslated regions. The introduced sense polynucleotide may be present in the plant cell transiently, or may be stably integrated into a plant chromosome or extrachromosomal replicon.

Alternatively, SLSRP gene expression can be inhibited by targeting nucleotide sequences complementary to the regulatory region of an SLSRP nucleotide sequence (e.g., an SLSRP promoter and/or enhancer) to form triple helical structures that prevent transcription of an SLSRP gene in target cells. See generally, Helene, 1991, Anticancer Drug Des. 6(6):569-84; Helene et al., 1992, Ann. N.Y. Acad. Sci. 660:27-36; and Maher, 1992, Bioassays 14(12):807-15.

In addition to the SLSRP nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50, or 75 consecutive nucleotides of a sense strand of the sequence set forth in SEQ ID NO:1, SEQ ID NO:3, SEQ ID NO:5, or SEQ ID NO:7; an anti-sense sequence of the sequence set forth in SEQ ID NO:1, SEQ ID NO:3, SEQ ID NO:5, or SEQ ID NO:7; or naturally occurring mutants thereof. Primers based on a nucleotide sequence of SEQ ID NO:1, SEQ ID NO:3, SEQ ID NO:5, or SEQ ID NO:7 can be used in PCR reactions to clone SLSRP homologs. Probes based on the SLSRP nucleotide sequences can be used to detect transcripts or genomic sequences encoding the same or substantially identical polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an SLSRP, such as by measuring a level of an SLSRP-encoding nucleic acid, in a sample of cells, e.g., detecting SLSRP mRNA levels or determining whether a genomic SLSRP gene has been mutated or deleted.

In particular, a useful method to ascertain the level of transcription of the gene (an indicator of the amount of mRNA available for translation to the gene product) is to perform a Northern blot (For reference, see, for example, Ausubel et al., 1988, Current Protocols in Molecular Biology, Wiley: New York). The information from a Northern blot at least partially demonstrates the degree of transcription of the transformed gene. Total cellular RNA can be prepared from cells, tissues, or organs by several methods, all well-known in the art, such as that described in Bormann et al., 1992, Mol. Microbiol. 6:317-326. To assess the presence or relative quantity of polypeptide translated from this mRNA, standard techniques, such as a Western blot, may be employed. These techniques are well known to one of ordinary skill in the art. (See, for example, Ausubel et al., 1988, Current Protocols in Molecular Biology, Wiley: New York).

The invention further provides an isolated recombinant expression vector comprising an SLSRP nucleic acid as described above, wherein expression of the vector in a host cell results in increased growth and tolerance to environmental stress as compared to a wild type variety of the host cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses, and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. As used herein with respect to a recombinant expression vector, "operatively linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel, 1990, Gene Expression Technology Methods in Enzymology 185, Academic Press, San Diego, Calif. and Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., SLSRPs, mutant forms of SLSRPs, fusion polypeptides, etc.).

The recombinant expression vectors of the invention can be designed for expression of SLSRPs in prokaryotic or eukaryotic cells. For example, SLSRP genes can be expressed in bacterial cells such as *C. glutamicum*, insect cells (using baculovirus expression vectors), yeast and other fungal cells (See Romanos et al., 1992, Foreign gene expression in yeast: a review, Yeast 8:423-488; Van den Hondel et al., 1991, Heterologous gene expression in filamentous fungi, in: More Gene Manipulations in Fungi, Bennet and Lasure, eds., p. 396-428: Academic Press: San Diego; and Van den Hondel and Punt, 1991, Gene transfer systems and vector development for filamentous fungi, in: Applied Molecular Genetics of Fungi, Peberdy et al., eds., p. 1-28, Cambridge University Press: Cambridge), algae (Falciatore et al., 1999, Marine Biotechnology 1(3): 239-251), ciliates of the types: *Holotrichia, Peritrichia, Spirotrichia, Suctoria, Tetrahymena, Paramecium, Colpidium, Glaucoma, Platyophrya, Potomacus, Pseudocohnilembus, Euplotes, Engelmaniella*, and *Stylonychia*, especially of the genus *Stylonychia lemnae* with vectors following a transformation method as described in PCT Application No. WO 98/01572, and multicellular plant cells (See Schmidt and Willmitzer, 1988, High efficiency *Agrobacterium tumefaciens*-mediated transformation of *Arabidopsis thaliana* leaf and cotyledon explants, Plant Cell Rep. 583-586; Plant Molecular Biology and Biotechnology, C Press, Boca Raton, Fla., chapter 6/7, S.71-119, 1993; White et al., 1993, Techniques for Gene Transfer, in: Transgenic Plants, Vol. 1, Engineering and Utilization, eds. Kung und R. Wu, 128-43, Academic Press; Potrykus, 1991, Annu. Rev. Plant Physiol. Plant Molec. Biol. 42:205-225 and references cited therein), or mammalian cells. Suitable host cells are discussed further in Goeddel, 1990, Gene Expression Technology: Methods in Enzymology 185, Academic Press: San Diego, Calif. Alternatively, the recombinant expression vector can be transcribed and translated in vitro, for example using T7 promoter regulatory sequences and T7 polymerase.

Expression of polypeptides in prokaryotes is most often carried out with vectors containing constitutive or inducible promoters directing the expression of either fusion or non-fusion polypeptides. Fusion vectors add a number of amino acids to a polypeptide encoded therein, usually to the amino terminus of the recombinant polypeptide but also to the C-terminus or fused within suitable regions in the polypeptides. Such fusion vectors typically serve three purposes: 1) to increase expression of a recombinant polypeptide; 2) to increase the solubility of a recombinant polypeptide; and 3) to aid in the purification of a recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion polypeptide. Such enzymes, and their cognate recognition sequences, include Factor Xa, thrombin, and enterokinase.

Typical fusion expression vectors include pGEX (Pharmacia Biotech Inc; Smith and Johnson, 1988, Gene 67: 31-40), pMAL (New England Biolabs, Beverly, Mass.), and pRIT5 (Pharmacia, Piscataway, N.J.) which fuse glutathione S-transferase (GST), maltose E binding polypeptide, or polypeptide A, respectively, to the target recombinant polypeptide. In one embodiment, the coding sequence of the SLSRP is cloned into a pGEX expression vector to create a vector encoding a fusion polypeptide comprising, from the N-terminus to the C-terminus, GST-thrombin cleavage site-X polypeptide. The fusion polypeptide can be purified by affinity chromatography using glutathione-agarose resin. Recombinant SLSRP unfused to GST can be recovered by cleavage of the fusion polypeptide with thrombin.

Examples of suitable inducible non-fusion *E. coli* expression vectors include pTrc (Amann et al., 1988, Gene 69:301-315) and pET 11d (Studier et al., 1990, Gene Expression Technology: Methods in Enzymology 185:60-89, Academic Press, San Diego, Calif.). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant polypeptide expression is to express the polypeptide in a host bacteria with an impaired capacity to proteolytically cleave the recombinant polypeptide (Gottesman, 1990, Gene Expression Technology: Methods in Enzymology 185:119-28, Academic Press, San Diego, Calif.). Another strategy is to alter the sequence of the nucleic acid to be inserted into an expression vector so that the individual codons for each amino acid are those preferentially utilized in the bacterium chosen for expression, such as *C. glutamicum* (Wada et al., 1992, Nucleic Acids Res. 20:2111-2118). Such alteration of nucleic acid sequences of the invention can be carried out by standard DNA synthesis techniques.

In another embodiment, the SLSRP expression vector is a yeast expression vector. Examples of vectors for expression in yeast *S. cerevisiae* include pYepSec1 (Baldari, et al., 1987, EMBO J. 6:229-234), pMFa (Kurjan and Herskowitz, 1982, Cell 30:933-943), pJRY 88 (Schultz et al., 1987, Gene 54:113-123), and pYES2 (Invitrogen Corporation, San Diego, Calif.). Vectors and methods for the construction of vectors appropriate for use in other fungi, such as the filamentous fungi, include those detailed in: Van den Hondel and Punt, 1991, "Gene transfer systems and vector development for filamentous fungi," in: Applied Molecular Genetics of Fungi, Peberdy, et al., eds., p. 1-28, Cambridge University Press: Cambridge.

In a preferred embodiment of the present invention, the SLSRPs are expressed in plants and plant cells such as unicellular plant cells (e.g. algae) (See Falciatore et al., 1999, Marine Biotechnology 1(3):239-251 and references therein) and plant cells from higher plants (e.g., the spermatophytes, such as crop plants). An SLSRP may be "introduced" into a plant cell by any means, including transfection, transformation or transduction, electroporation, particle bombardment, agroinfection, and the like. One transformation method known to those of skill in the art is the dipping of a flowering plant into an *Agrobacteria* solution, wherein the *Agrobacteria* contain the SLSRP nucleic acid, followed by breeding of the transformed gametes.

Other suitable methods for transforming or transfecting host cells including plant cells can be found in Sambrook, et al., 1989, Molecular Cloning: A Laboratory Manual. latest ed., Cold Spring Harbor Laboratory, Cold Spring Harbor Laboratory Press, Cold Spring Harbor, N.Y. and other laboratory manuals such as Methods in Molecular Biology, 1995, Vol. 44, *Agrobacterium* protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed, canola, *manihot*, pepper, sunflower, tagetes, solanaceous plants like potato, tobacco, eggplant, tomato, *Vicia* species, pea, alfalfa, bushy plants (coffee, cacao, tea), *Salix* species, trees (oil palm, coconut), perennial grasses, and forage crops, these crop plants are also preferred target plants for a genetic engineering as one further embodiment of the present invention. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover, and Sweet Clover.

In one embodiment of the present invention, transfection of an SLSRP into a plant is achieved by *Agrobacterium* mediated gene transfer. *Agrobacterium* mediated plant transformation can be performed using for example the GV3101 (pMP90) (Koncz and Schell, 1986, Mol. Gen. Genet. 204: 383-396) or LBA4404 (Clontech) *Agrobacterium tumefaciens* strain. Transformation can be performed by standard transformation and regeneration techniques (Deblaere et al., 1994, Nucl. Acids. Res. 13:4777-4788; Gelvin et al., 1995, Plant Molecular Biology Manual, $2^{nd}$ Ed.-Dordrecht: Kluwer Academic Publ.,-in Sect., Ringbuc Zentrale Signatur: BT11-P ISBN 0-7923-2731-4; Glick et al., 1993, Methods in Plant Molecular Biology and Biotechnology, Boca Raton: CRC Press, 360 S., ISBN 0-8493-5164-2). For example, rapeseed can be transformed via cotyledon or hypocotyl transformation (Moloney et al., 1989, Plant Cell Report 8:238-242; De Block et al., 1989, Plant Physiol. 91:694-701). Use of antibiotics for *Agrobacterium* and plant selection depends on the binary vector and the *Agrobacterium* strain used for transformation. Rapeseed selection is normally performed using kanamycin as the selectable plant marker. *Agrobacterium* mediated gene transfer to flax can be performed using, for example, a technique described by Mlynarova et al., 1994, Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543, or U.S. Pat. No. 5,169,770. Transformation of maize can be achieved by particle bombardment, polyethylene glycol mediated DNA uptake, or via the silicon carbide fiber technique. (See, for example, Freeling and Walbot, 1993, "The maize handbook" Springer Verlag: NY, ISBN 3-540-97826-7). A specific example of maize transformation is found in U.S. Pat. No. 5,990,387, and a specific example of wheat transformation can be found in PCT Application No. WO 93/07256.

According to the present invention, the introduced SLSRP may be maintained in the plant cell stably if it is incorporated into a non-chromosomal autonomous replicon or integrated into the plant chromosomes. Alternatively, the introduced SLSRP may be present on an extra-chromosomal non-replicating vector and may be transiently expressed or transiently active.

In one embodiment, a homologous recombinant microorganism can be created wherein the SLSRP is integrated into a chromosome, a vector is prepared which contains at least a portion of an SLSRP into which a deletion, addition, or substitution has been introduced to thereby alter, e.g., functionally disrupt, the SLSRP gene. Preferably, the SLSRPs are *Physcomitrella patens* and *Glycine max* SLSRP genes, but they can be homologs from a related plant or even from a mammalian, yeast, or insect source. In one embodiment, the vector is designed such that, upon homologous recombination, the endogenous SLSRP gene is functionally disrupted (i.e., no longer encodes a functional polypeptide; also referred to as a knock-out vector). Alternatively, the vector can be designed such that, upon homologous recombination, the endogenous SLSRP gene is mutated or otherwise altered but still encodes a functional polypeptide (e.g., the upstream regulatory region can be altered to thereby alter the expression of the endogenous SLSRP). To create a point mutation via homologous recombination, DNA-RNA hybrids can be used in a technique known as chimeraplasty (Cole-Strauss et al., 1999, Nucleic Acids Research 27(5):1323-1330 and Kmiec, 1999, Gene Therapy American Scientist 87(3):240-247). Homologous recombination procedures in *Physcomitrella patens* are also well known in the art and are contemplated for use herein.

Whereas in the homologous recombination vector, the altered portion of the SLSRP gene is flanked at its 5' and 3' ends by an additional nucleic acid molecule of the SLSRP gene to allow for homologous recombination to occur between the exogenous SLSRP gene carried by the vector and an endogenous SLSRP gene, in a microorganism or plant. The additional flanking SLSRP nucleic acid molecule is of sufficient length for successful homologous recombination with the endogenous gene. Typically, several hundreds of base pairs up to kilobases of flanking DNA (both at the 5' and 3' ends) are included in the vector (See e.g., Thomas and Capecchi, 1987, Cell 51:503 for a description of homologous recombination vectors or Strepp et al., 1998, PNAS, 95(8): 4368-4373 for cDNA based recombination in *Physcomitrella patens* and *Glycine max*). The vector is introduced into a microorganism or plant cell (e.g., via polyethylene glycol mediated DNA), and cells in which the introduced SLSRP gene has homologously recombined with the endogenous SLSRP gene are selected using art-known techniques.

In another embodiment, recombinant microorganisms can be produced that contain selected systems that allow for regulated expression of the introduced gene. For example, inclusion of an SLSRP gene on a vector placing it under control of the lac operon permits expression of the SLSRP gene only in the presence of IPTG. Such regulatory systems are well known in the art.

Whether present in an extra-chromosomal non-replicating vector or a vector that is integrated into a chromosome, the SLSRP polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693-8711). Examples of plant expression vectors include those detailed in: Becker et al., 1992, New plant binary vectors with selectable markers located proximal to the left border, Plant Mol. Biol. 20:1195-1197; and Bevan, 1984, Nucl. Acid. Res. 12:8711-8721; Vectors for Gene Transfer in Higher Plants; in: Transgenic Plants, Vol. 1, Engineering and Utilization, eds.: Kung and Wu, 1993, Academic Press, S. 15-38.

Plant gene expression should be operatively linked to an appropriate promoter conferring gene expression in a timely, cell specific, or tissue specific manner. Promoters useful in the expression cassettes of the invention include any promoter that is capable of initiating transcription in a plant cell. Such promoters include, but are not limited to, those that can be obtained from plants, plant viruses, and bacteria that contain genes that are expressed in plants, such as *Agrobacterium* and *Rhizobium*.

The promoter may be constitutive, inducible, developmental stage-preferred, cell type-preferred, tissue-preferred, or organ-preferred. Constitutive promoters are active under most conditions. Examples of constitutive promoters include the CaMV 19S and 35 S promoters (Odell et al., 1985, Nature 313:810-812), the sX CaMV 35S promoter (Kay et al., 1987, Science 236:1299-1302) the Sep1 promoter, the rice actin promoter (McElroy et al., 1990, Plant Cell 2:163-171), the *Arabidopsis* actin promoter, the ubiquitan promoter (Christensen et al., 1989, Plant Molec. Biol. 18:675-689), pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are preferentially active under certain environmental conditions, such as the presence or absence of a nutrient or metabolite, heat or cold, light, pathogen attack, anaerobic conditions, and the like. For example, the hsp80 promoter from *Brassica* is induced by heat shock; the PPDK promoter is induced by light; the PR-1 promoters from tobacco, *Arabidopsis*, and maize are inducible by infection with a pathogen; and the Adh1 promoter is induced by hypoxia and cold stress. Plant gene expression can also be facilitated via an inducible promoter (For review, see Gatz, 1997, Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992, Plant J. 2:397-404), and an ethanol inducible promoter (PCT Application No. WO 93/21334).

In one preferred embodiment of the present invention, the inducible promoter is a stress-inducible promoter. For the purposes of the invention, stress inducible promoters are preferentially active under one or more of the following stresses: sub-optimal conditions associated with salinity, drought, temperature, metal, chemical, pathogenic, and oxidative stresses. Stress inducible promoters include, but are not limited to, Cor78 (Chak et al., 2000, Planta 210:875-883; Hovath et al., 1993, Plant Physiol. 103:1047-1053), Cor15a (Artus et al., 1996, PNAS 93(23):13404-09), Rci2A (Medina et al., 2001, Plant Physiol. 125:1655-66; Nylander et al., 2001, Plant Mol. Biol. 45:341-52; Navarre and Goffeau, 2000, EMBO J. 19:2515-24; Capel et al., 1997, Plant Physiol. 115: 569-76), Rd22 (Xiong et al., 2001, Plant Cell 13:2063-83; Abe et al., 1997, Plant Cell 9:1859-68; Iwasaki et al., 1995, Mol. Gen. Genet. 247:391-8), cDet6 (Lang and Palve, 1992, Plant Mol. Biol. 20:951-62), ADH1 (Hoeren et al., 1998, Genetics 149:479-90), KAT1 (Nakamura et al., 1995, Plant Physiol. 109:371-4), KST1 (Müller-Röber et al., 1995, EMBO 14:2409-16), Rhal (Terryn et al., 1993, Plant Cell 5:1761-9; Terryn et al., 1992, FEBS Lett. 299(3):287-90), ARSK1 (Atkinson et al., 1997, GenBank Accession # L22302, and PCT Application No. WO 97/20057), PtxA (Plesch et al., GenBank Accession # X67427), SbHRGP3 (Ahn et al., 1996, Plant Cell 8:1477-90), GH3 (Liu et al., 1994, Plant Cell 6:645-57), the pathogen inducible PRPI-gene promoter (Ward et al., 1993, Plant. Mol. Biol. 22:361-366), the heat inducible hsp80-promoter from tomato (U.S. Pat. No. 5,187, 267), cold inducible alpha-amylase promoter from potato (PCT Application No. WO 96/12814), or the wound-inducible pinII-promoter (European Patent No. 375091). For other examples of drought, cold, and salt-inducible promoters, such as the RD29A promoter, see Yamaguchi-Shinozalei et al., 1993, Mol. Gen. Genet. 236:331-340.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue-preferred and organ-preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters, and the like. Seed-preferred promoters are preferentially expressed during seed development and/or germination. For example, seed-preferred promoters can be embryo-preferred, endosperm-preferred, and seed coat-preferred. See Thompson et al., 1989, BioEssays 10:108. Examples of seed preferred promoters include, but are not limited to, cellulose synthase (celA), Cim1, gamma-zein, globulin-1, maize 19 kD zein (cZ19B1), and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991, Mol. Gen. Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce-4-promoter from *Brassica* (PCT Application No. WO 91/13980), or the legumin B4 promoter (LeB4; Baeumlein et al., 1992, Plant Journal, 2(2): 233-9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, *Sorghum* kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the γ-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985, Cell 43: 729-736).

The invention further provides a recombinant expression vector comprising an SLSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to an SLSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus wherein antisense nucleic acids are produced under the control of a high efficiency regulatory region. The activity of the regulatory region can be determined by the cell type into which the vector is introduced. For a discussion of the regulation of gene expression using antisense genes, see Weintraub, H. et al., 1986, Antisense RNA as a molecular tool for genetic analysis, Reviews—Trends in Genetics, Vol. 1(1), and Mol et al., 1990, FEBS Letters 268: 427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an SLSRP can be expressed in bacterial cells such as *C. glutamicum*, insect cells, fungal cells, or mammalian cells (such as Chinese hamster ovary cells (CHO) or COS cells), algae, ciliates, plant cells, fungi, or other microorganisms like *C. glutamicum*. Other suitable host cells are known to those skilled in the art.

The nucleic acid molecules, polypeptides, polypeptide homologs, fusion polypeptides, primers, vectors, and host cells described herein can be used in one or more of the following methods: identification of *Physcomitrella patens* or *Glycine max* and related organisms; mapping of genomes of organisms related to *Physcomitrella patens* or *Glycine max*; identification and localization of *Physcomitrella patens* or *Glycine max* sequences of interest; evolutionary studies; determination of SLSRP regions required for function; modulation of an SLSRP activity; modulation of the metabolism of one or more cell functions; modulation of the transmembrane transport of one or more compounds; modulation of stress resistance; and modulation of expression of SLSRP nucleic acids. In one embodiment of these methods, the SLSRP functions as a active plant transcription factor.

The moss *Physcomitrella patens* or *Glycine max* represents one member of the mosses. It is related to other mosses such as *Ceratodon purpureus* that is capable of growth in the absence of light. Mosses like *Ceratodon* and *Physcomitrella* share a high degree of sequence identity on the DNA sequence and polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The SLSRP nucleic acid molecules of the invention have a variety of uses. Most importantly, the nucleic acid and amino acid sequences of the present invention can be used to transform plants, thereby increasing growth and inducing tolerance to stresses such as drought, high salinity, and cold. The present invention therefore provides a transgenic plant transformed with an SLSRP nucleic acid, wherein expression of the nucleic acid sequence in the plant results in the plant's increased growth and tolerance to environmental stress as compared to a wild type variety of the plant. The transgenic plant can be a monocot or a dicot. The invention further provides that the transgenic plant can be selected from maize, wheat, rye, oat, triticale, rice, barley, soybean, peanut, cotton, rapeseed, canola, *manihot*, pepper, sunflower, tagetes, solanaceous plants, potato, tobacco, eggplant, tomato, *Vicia* species, pea, alfalfa, coffee, cacao, tea, *Salix* species, oil palm, coconut, perennial grass, and forage crops, for example.

In particular, the present invention describes using the expression of PpSCL1, PpSCL2, PpSCL3, and GmSCL1 to engineer plants that increased growth and drought-tolerance, salt-tolerance, and/or cold-tolerance. This strategy has herein been demonstrated for *Arabidopsis thaliana*, but its application is not restricted to these plants. Accordingly, the invention provides a transgenic plant containing an SLSRP such as PpSCL1 as defined in SEQ ID NO:2, PpSCL2 as defined in SEQ ID NO:4, PpSCL3 as defined in SEQ ID NO:6, or GmSCL1 as defined in SEQ ID NO:8, wherein the plant has an increased growth and tolerance to an environmental stress selected from one or more of the group consisting of drought, increased salt, or decreased or increased temperature. In preferred embodiments, the environmental stress is drought or decreased temperature.

Accordingly, the invention provides a method of producing a transgenic plant with an SLSRP coding nucleic acid, wherein expression of the nucleic acid(s) in the plant results in increased growth and tolerance to environmental stress as compared to a wild type variety of the plant comprising: (a) introducing into a plant cell an expression vector comprising an SLSRP nucleic acid, and (b) generating from the plant cell a transgenic plant with a increased growth and tolerance to environmental stress as compared to a wild type variety of the plant. The plant cell includes, but is not limited to, a protoplast, gamete producing cell, and a cell that regenerates into a whole plant. As used herein, the term "transgenic" refers to any plant, plant cell, callus, plant tissue, or plant part, that contains all or part of at least one recombinant polynucleotide. In many cases, all or part of the recombinant polynucleotide is stably integrated into a chromosome or stable extra-chromosomal element, so that it is passed on to successive generations. In preferred embodiments, the SLSRP nucleic acid encodes a protein comprising the polypeptide of SEQ ID NO:2, SEQ ID NO:4, SEQ ID NO:6, or SEQ ID NO:8.

The present invention also provides a method of modulating a plant's growth and tolerance to an environmental stress comprising, modifying the expression of an SLSRP coding nucleic acid in the plant. The plant's growth and tolerance to the environmental stress can be increased or decreased as achieved by increasing or decreasing the expression of an SLSRP, respectively. Preferably, the plant's growth and tolerance to the environmental stress is increased by increasing expression of an SLSRP. Expression of an SLSRP can be modified by any method known to those of skill in the art. The methods of increasing expression of SLSRPs can be used wherein the plant is either transgenic or not transgenic. In cases when the plant is transgenic, the plant can be transformed with a vector containing any of the above described SLSRP coding nucleic acids, or the plant can be transformed with a promoter that directs expression of native SLSRP in the plant, for example. The invention provides that such a promoter can be tissue-preferred, developmentally regulated, stress inducible, or a combination thereof. Alternatively, non-transgenic plants can have native SLSRP expression modified by inducing a native promoter. The expression of PpSCL1 as defined in SEQ ID NO:1, PpSCL2 as defined in SEQ ID NO:3, PpSCL3 as defined in SEQ ID NO:5, or GmSCL1 as defined in SEQ ID NO:7 in target plants can be accomplished by, but is not limited to, one of the following examples: (a) constitutive promoter, (b) stress-inducible promoter, (c) chemical-induced promoter, and (d) engineered promoter overexpression with, for example, zinc-finger derived transcription factors (Greisman and Pabo, 1997, Science 275: 657).

In a preferred embodiment, transcription of the SLSRP is modulated using zinc-finger derived transcription factors (ZFPs) as described in Greisman and Pabo, 1997, Science 275:657 and manufactured by Sangamo Biosciences, Inc. These ZFPs comprise both a DNA recognition domain and a functional domain that causes activation or repression of a target nucleic acid such as an SLSRP nucleic acid. Therefore, activating and repressing ZFPs can be created that specifically recognize the SLSRP promoters described above and used to increase or decrease SLSRP expression in a plant, thereby modulating the stress tolerance of the plant. The present invention also includes identification of the homologs of PpSCL1 as defined in SEQ ID NO:1, PpSCL2 as defined in SEQ ID NO:3, PpSCL3 as defined in SEQ ID NO:5, or GmSCL1 as defined in SEQ ID NO:7 in a target plant, as well as the homolog's promoter. The invention also provides a method of increasing expression of a gene of interest within a host cell as compared to a wild type variety of the host cell, wherein the gene of interest is transcribed in response to an SLSRP, comprising: (a) transforming the host cell with an expression vector comprising an SLSRP coding nucleic acid, and (b) expressing the SLSRP within the host cell, thereby increasing the expression of the gene transcribed in response to the SLSRP, as compared to a wild type variety of the host cell.

In addition to introducing the SLSRP nucleic acid sequences into transgenic plants, these sequences can also be used to identify an organism as being *Physcomitrella patens, Glycine max*, or a close relative thereof. Also, they may be used to identify the presence of *Physcomitrella patens, Glycine max*, or a relative thereof in a mixed population of microorganisms. The invention provides the nucleic acid sequences of *Physcomitrella patens* and a *Glycine max* gene; by probing the extracted genomic DNA of a culture of a unique or mixed population of microorganisms under stringent conditions with a probe spanning a region of the *Physcomitrella patens* or *Glycine max* gene that is unique to this organism, one can ascertain whether this organism is present.

Further, the nucleic acid and polypeptide molecules of the invention may serve as markers for specific regions of the genome. This has utility not only in the mapping of the genome, but also in functional studies of *Physcomitrella patens* or *Glycine max* polypeptides. For example, to identify the region of the genome to which a particular *Physcomitrella patens* DNA-binding polypeptide binds, the *Physcomitrella patens* genome could be digested, and the fragments incubated with the DNA-binding polypeptide. Those fragments that bind the polypeptide may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the polypeptide binds. Further, the nucleic acid molecules of the invention may be sufficiently identical to the sequences of related species such that these nucleic acid molecules may serve as markers for the construction of a genomic map in related mosses.

The SLSRP nucleic acid molecules of the invention are also useful for evolutionary and polypeptide structural studies. The transcription and signal transduction processes in which the molecules of the invention participate are utilized by a wide variety of prokaryotic and eukaryotic cells; by comparing the sequences of the nucleic acid molecules of the present invention to those encoding similar proteins from other organisms, the evolutionary relatedness of the organisms can be assessed. Similarly, such a comparison permits an assessment of which regions of the sequence are conserved and which are not, which may aid in determining those regions of the polypeptide that are essential for the functioning of the transcription factor. This type of determination is of value for polypeptide engineering studies and may give an indication of what the polypeptide can tolerate in terms of mutagenesis without losing function.

Manipulation of the SLSRP nucleic acid molecules of the invention may result in the production of SLSRPs having functional differences from the wild-type SLSRPs. These polypeptides may be improved in efficiency or activity, may be present in greater numbers in the cell than is usual, or may be decreased in efficiency or activity.

There are a number of mechanisms by which the alteration of an SLSRP of the invention may directly affect stress response and/or stress tolerance. In the case of plants expressing SLSRPs, increased tolerance can lead to improved salt and/or solute partitioning within the plant tissue and organs.

The effect of the genetic modification in plants, *C. glutamicum*, fungi, algae, or ciliates on plant growth and/or stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, polypeptide synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter III: Product recovery and purification, page 469-714, VCH: Weinheim et al., 1988, Bioseparations: downstream processing for biotechnology, John Wiley and Sons; Kennedy and Cabral, 1992, Recovery processes for biological materials, John Wiley and Sons; Shaeiwitz and Henry, 1988, Biochemical separations, in: Ulmann's Encyclopedia of Industrial Chemistry, vol. B3, Chapter 11, page 1-27, VCH: Weinheim; and Dechow, 1989, Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stresses. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatula*, etc., using standard protocols. The resulting transgenic cells and/or plants derived there from can then be assayed for fail or alteration of their improved growth and/or tolerance to drought, salt, and temperature stresses.

The engineering of one or more SLSRP genes of the invention may also result in SLSRPs having altered activities which indirectly impact the growth and/or stress response and/or stress tolerance of algae, plants, ciliates, or fungi, or other microorganisms like *C. glutamicum*. For example, the normal biochemical processes of metabolism result in the production of a variety of products (e.g., hydrogen peroxide and other reactive oxygen species) which may actively interfere with these same metabolic processes.

Additionally, the sequences disclosed herein, or fragments thereof, can be used to generate knockout mutations in the genomes of various organisms, such as bacteria, mammalian cells, yeast cells, and plant cells (Girke, T., 1998, The Plant Journal 15:39-48). The resultant knockout cells can then be evaluated for their ability or capacity to tolerate various stress conditions, their response to various stress conditions, and the effect on the phenotype and/or genotype of the mutation. For other methods of gene inactivation, see U.S. Pat. No. 6,004,804 and Puttaraju et al., 1999, Nature Biotechnology 17:246-252.

The aforementioned mutagenesis strategies for SLSRPs resulting in increased growth and stress resistance are not meant to be limiting; variations on these strategies will be readily apparent to one skilled in the art. Using such strategies, and incorporating the mechanisms disclosed herein, the nucleic acid and polypeptide molecules of the invention may be utilized to generate algae, ciliates, plants, fungi, or other microorganisms like *C. glutamicum* expressing mutated SLSRP nucleic acid and polypeptide molecules such that the stress tolerance is improved.

The present invention also provides antibodies that specifically bind to an SLSRP, or a portion thereof, as encoded by a nucleic acid described herein. Antibodies can be made by many well-known methods (See, e.g., Harlow and Lane, 1988, "Antibodies; A Laboratory Manual," Cold Spring Harbor Laboratory, Cold Spring Harbor, N.Y.

The phrases "selectively binds" and "specifically binds" with the polypeptide refer to a binding reaction that is determinative of the presence of the polypeptide in a heterogeneous population of polypeptides and other biologics. Thus, under designated immunoassay conditions, the specified antibodies bound to a particular polypeptide do not bind in a significant amount to other polypeptides present in the sample. Selective binding of an antibody under such conditions may require an antibody that is selected for its specificity for a particular polypeptide. A variety of immunoassay formats may be used to select antibodies that selectively bind with a particular polypeptide. For example, solid-phase ELISA immunoassays are routinely used to select antibodies selectively immunoreactive with a polypeptide. See Harlow and Lane, 1988, "Antibodies, A Laboratory Manual" Cold Spring Harbor Publications, NY, for a description of immunoassay formats and conditions that could be used to determine selective binding.

In some instances, it is desirable to prepare monoclonal antibodies from various hosts. A description of techniques for preparing such monoclonal antibodies may be found in Stites et al., eds., "Basic and Clinical Immunology," (Lange Medical Publications, Los Altos, Calif., Fourth Edition) and references cited therein, and in Harlow and Lane, 1988, "Antibodies, A Laboratory Manual" Cold Spring Harbor Publications, NY.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of *Physcomitrella patens* Cultures

For this study, plants of the species *Physcomitrella patens* (Hedw.) B.S.G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55:438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days. These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromol $m^2$ $s^{-1}$ (white light; Philips TL 65W/25 fluorescent tube) and a light/dark change of 16/8 hours. The moss was either modified in liquid culture using Knop medium according to Reski and Abel (1985, Planta 165: 354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; and 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol, and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 µl of $H_2O$+RNAse (50 mg/ml final concentration). The DNA was dissolved overnight at 4° C., and the RNAse digestion was subsequently carried out at 37° C. for 1 hour. Storage of the DNA took place at 4° C.

Example 3

Isolation of Total RNA and Poly-(A)+ RNA and cDNA Library Construction from *Physcomitrella patens*

For the investigation of transcripts, both total RNA and poly-(A)$^+$ RNA were isolated. The total RNA was obtained from wild-type 9 day old protonemata following the GTC-method (Reski et al., 1994, Mol. Gen. Genet., 244: 352-359). The Poly(A)+ RNA was isolated using Dyna Beads$^R$ (Dynal, Oslo, Norway) following the instructions of the manufacturer's protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour), and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany), and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (See Sambrook et al., 1989, Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

```
5'-CAGGAAACAGCTATGACC-3'      SEQ ID NO:9

5'-CTAAAGGGAACAAAAGCTG-3'     SEQ ID NO:10

5'-TGTAAAACGACGGCCAGT-3'      SEQ ID NO:11
```

Sequences were processed and annotated using the software package EST-MAX commercially provided by Bio-Max (Munich, Germany). The program incorporates practically all bioinformatics methods important for functional and structural characterization of protein sequences. For reference, see the website at pedant.mips.biochem.mpg.de. The most important algorithms incorporated in EST-MAX are: FASTA (Very sensitive sequence database searches with estimates of statistical significance; Pearson, 1990, Rapid and sensitive sequence comparison with FASTP and FASTA, Methods Enzymol. 183:63-98); BLAST (Very sensitive sequence database searches with estimates of statistical significance; Altschul et al., Basic local alignment search tool, Journal of Molecular Biology 215:403-10); PREDATOR (High-accuracy secondary structure prediction from single and multiple sequences; Frishman and Argos, 1997, 75% accuracy in protein secondary structure prediction. Proteins 27:329-335); CLUSTAL W (Multiple sequence alignment; Thompson et al., 1994, CLUSTAL W (improving the sensitivity of progressive multiple sequence alignment through sequence weighting, position-specific gap penalties and weight matrix choice, Nucleic Acids Research 22:4673-4680); TMAP (Transmembrane region prediction from multiple aligned sequences; Persson and Argos, 1994, Prediction of transmembrane segments in proteins utilizing multiple sequence alignments. J. Mol. Biol. 237:182-192); ALOM2 (Transmembrane region prediction from single sequences; Klein et al., Prediction of protein function from sequence properties: A discriminate analysis of a database. Biochim. Biophys. Acta 787:221-226 (1984). Version 2 by Dr. K. Nakai); PROSEARCH (Detection of PROSITE protein sequence patterns; Kolakowski et al., 1992, ProSearch: fast searching of protein sequences with regular expression patterns related to protein structure and function. Biotechniques 13, 919-921); BLIMPS (Similarity searches against a database of ungapped blocks, Wallace and Henikoff, 1992); PAT-MAT (a searching and extraction program for sequence, pattern and block queries and databases, CABIOS 8:249-254. Written by Bill Alford).

Example 5

Identification of *Physcomitrella patens* ORFs Corresponding to PpSCL1, PpSCL2 and PpSCL3

The *P. patens* partial cDNAs (ESTS) were identified in the *P. patens* EST sequencing program using the program EST-MAX through BLAST analysis. The full-length nucleotide sequences of PpSCL1, PpSCL2, and PpSCL3 are defined in SEQ ID NO:1, SEQ ID NO:3, and SEQ ID NO:5, respectively. The predicted amino acid sequences of PpSCL1 (SEQ ID NO:2), PpSCL2 (SEQ ID NO:4) and PpSCL3 (SEQ ID NO:6) shared significant sequence identities and similarities with scarecrow-like gene products as shown in Tables 1, 2 and 3.

TABLE 1

Degree of Amino Acid Identity and Similarity of PpSCL1 (EST 386) and Other Homologous Proteins (GCG Gap Program was used: gap penalty: 10; gap extension penalty: 0.1; score matrix: blosum 62)

| Public Database Accession # | Protein Name | Species | Identity | Similarity |
|---|---|---|---|---|
| Q7X9T5 | SCARECROW-like protein | *L. Longiflorum* | 30 | 42 |
| Q8S2B3 | Putative protein | *O. sativa* | 30 | 42 |
| T02531 | Probable SCARECROW gene regulator | *A. thaliana* | 30 | 42 |
| Q94HJ4 | Putative SCARECROW gene regulator | *O. sativa* | 27 | 39 |
| Q9LNX6 | Putative protein | *A. thaliana* | 15 | 21 |
| T02736 | Probable SCARECROW gene regulator | *A. thaliana* | 16 | 24 |

TABLE 2

Degree of Amino Acid Identity and Similarity of PpSCL2 (EST 166) and Other Homologous Proteins (GCG Gap Program was used: gap penalty: 10; gap extension penalty: 0.1; score matrix: blosum 62)

| Public Database Accession # | Protein Name | Species | Identity | Similarity |
|---|---|---|---|---|
| NP 190990 | Scarecrow transcription factor, putative | *Arabidopsis thaliana* | 26.3 | 39.0 |
| T51244 | Scarecrow protein | *Arabidopsis thaliana* | 26.3 | 38.8 |
| Q6L5ZO | Scarecrow | *Oryza sativa* | 23.9 | 37.5 |
| Q9FUZ7 | Scarecrow | *Zea mays* | 24.2 | 37.9 |
| Q9AVK4 | Scarecrow | *Pisum sativum* | 19.6 | 30.9 |

TABLE 3

Degree of Amino Acid Identity and Similarity of PpSCL3 (EST 512) and Other Homologous Proteins (GCG Gap Program was used: gap penalty: 10; gap extension penalty: 0.1; score matrix: blosum 62)

| Public Database Accession # | Protein Name | Species | Identity | Similarity |
| --- | --- | --- | --- | --- |
| NP_199626 | Phytochrome A signal transduction 1 | Arabidopsis thaliana | 39.6 | 48.6 |
| Q8GYN7 | Putative scarecrow gene regulator | Arabidopsis thaliana | 36.9 | 44.5 |
| NP_175475 | Scarecrow-like transcription factor 5 | Arabidopsis thaliana | 41.9 | 53.7 |
| E966542 | Scarecrow-like protein | Arabidopsis thaliana | 39.8 | 50.5 |
| Q7EXH0 | Putative scarecrow protein | Arabidopsis thaliana | 41.4 | 53.6 |

Example 6
Cloning of the Full-Length *Physcomitrella patens* cDNA Encoding for PpSCL1, PpSCL2, and PpSCL3

To isolate the clones encoding the full-length PpSCL1 (SEQ ID NO:1), PpSCL2 (SEQ ID NO:3), and PpSCL3 (SEQ ID NO:5) from *P. patens*, cDNA libraries were created with SMART RACE cDNA Amplification kit (Clontech Laboratories) following manufacturer's instructions. Total RNA isolated as described in Example 3 was used as the template. The cultures were treated prior to RNA isolation as follows: Salt Stress: 2, 6, 12, 24, 48 hours with 1-M NaCl-supplemented medium; Cold Stress: 4° C. for the same time points as for salt; Drought Stress: cultures were incubated on dry filter paper for the same time points as for salt.

5' RACE Protocol

The EST sequences identified from the database search as described in Example 4 were used to design oligos for RACE (See Table 6). The extended sequences for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions. The sequences obtained from the RACE reactions corresponded to full-length coding region and were used to design oligos for full-length cloning of the respective gene (See below full-length amplification).

TABLE 4

Scheme and primers used for cloning of full-length clones

| Gene | Final Product Sites | Isolation Method | Primers Race | Primers RT-PCT |
| --- | --- | --- | --- | --- |
| PpSCL-1 (EST 386) | XmaI/SacI | 5' RACE and RT-PCR for Full-length clone | NVT: GAGGGAAAGCTGT GGCGAGCTAAAA (SEQ ID NO:12) | RC896: ATCCCGGGAGACAA GCTAAGCAAGTAAG CAAG (SEQ ID NO:13) RC897: GCGAGCTCGGATAT AGTACAGAGCTGCA GGCGAA (SEQ ID NO:14) |
| PpSCL2 (EST 166) | EcoRV/ EcoRV | 5' Race PCR for the full-length clone | NVT: (SEQ ID NO:15) GTCGGAGGATCG GAGTAACTGGTCT | RC618: (SEQ ID NO:16) GCGATATCGGCGGT GATCTCCGTTTCCT GGCTCT RC619: (SEQ ID NO:17) GCGATATCGTATAG TCCAGATTGTCTGG CACTGT |
| PpSCL3 (EST 512) | BbrPI/SpeI | 5' Race PCR for the full-length clone | NVT: (SEQ ID NO:18) GTGAACCCCCTGG TCGAGCAGCCAA | RC705: (SEQ ID NO:19) CCCGGGAAGAAGA GCGTGAACGTGGG AT RC706: (SEQ ID NO:20) AGTACTGCCTTACC AAATGAGACAGGT CCTCA |

Full-length Amplification

Full-length clones corresponding to PpSCL1 (SEQ ID NO:1), PpSCL2 (SEQ ID NO:3), or PpSCL3 (SEQ ID NO:5) were obtained by performing polymerase chain reaction (PCR) with gene-specific primers and the original EST as the template. The conditions for the reaction were standard conditions with PWO DNA polymerase (Roche) PCR was performed according to standard conditions and to manufacturer's protocols (Sambrook et al., 1989, Molecular Cloning, A Laboratory Manual. $2^{nd}$ Edition, Cold Spring Harbor Laboratory Press, Cold Spring Harbor, N.Y., Biometra T3 Thermocycler). The parameters for the reaction were: five minutes at 94° C. followed by five cycles of one minute at 94° C., one minute at 50° C., and 4 minutes at 72° C. This was followed by twenty-five cycles of one minute at 94° C., one minute at 65° C., and 4 minutes at 72° C. These parameters generated a fragment of 4.0 kb for PpSCL1, 2.8 kb for PpSCL2, and 2.3 kb for PpSCL3.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al., 1989, Molecular Cloning, A Laboratory Manual. $2^{nd}$ Edition, Cold Spring Harbor Laboratory Press, Cold Spring Harbor, N.Y.). Transformed cells were selected for on LB agar containing 100 µg/ml carbenicillin, 0.8 mg X-gal (5-bromo-4-chloro-3-indolyl-β-D-galactoside), and 0.8 mg IPTG (isopropylthio-1-D-galactoside) grown overnight at 37° C. White colonies were selected and used to inoculate 3 ml of liquid LB containing 100 µg/ml ampicillin and grown overnight at 37° C. Plasmid DNAs were extracted using the QIAprep Spin Miniprep Kit (Qiagen) following manufacturer's instructions. Analyses of subsequent clones and restriction mapping was performed according to standard molecular biology techniques (Sambrook et al., 1989, Molecular Cloning, A Laboratory Manual, 2nd Edition, Cold Spring Harbor Laboratory Press, Cold Spring Harbor, N.Y.).

Figure 2:
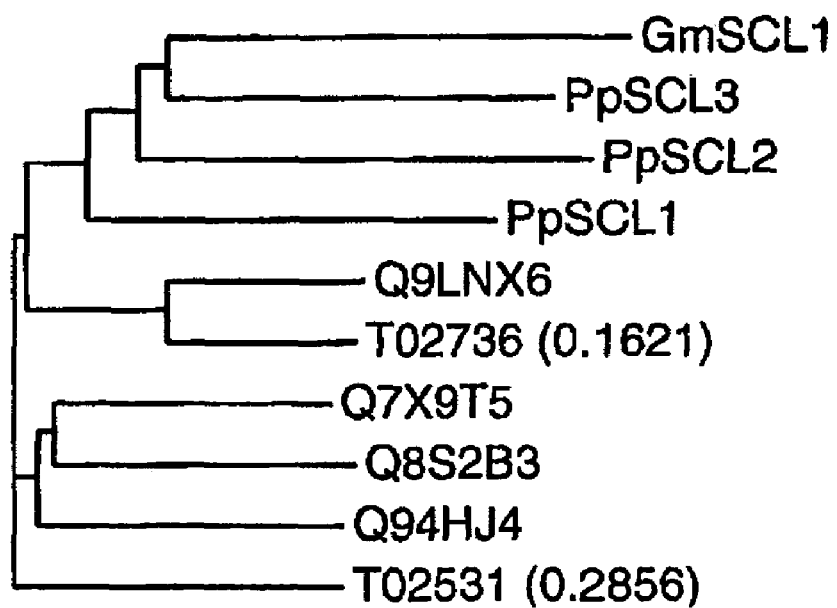
FIG. 2 shows the phylogenetic tree of the disclosed PpSCL1, PpSCL2, PpSCL3, and GmSCL1 (SEQ ID NOs: 2, 4, 6, and 8) amino acid sequence with the sequences of four known members of the GRAS family. The diagram was generated using Align X of Vector NTI.

Full-length nucleotide sequences of PpSCL1 (SEQ ID NO:1), PpSCL2 (SEQ ID NO:3), or PpSCL3 (SEQ ID NO:5) were analyzed with Biomax and Vector NTI. The amino acid sequences of PpSCL1 (SEQ ID NO:2), PpSCL2 (SEQ ID NO:4) and PpSCL3 (SEQ ID NO:6) have homologies to the GRS family of transcription factors. For instance, the PpSCL1 amino acid sequence (SEQ ID NO:2) has homology to the GRAS family of transcription factors. The three most conserved motifs in the GRAS gene family, the VHIID, PFYRE and SAW motifs are found in PpSCL1 (SEQ ID NO:2). A blast search of PpSCL1 (SEQ ID NO:2) in ERGO of sequences from 12 Archaea, 145 Bacteria and 84 Eukaryotes identified similar sequences in *Arabidopsis*, corn, and tomato (minimum strictness of 0.00001). A blast search of the PpSCL1 (SEQ ID NO:2), PpSCL2 (SEQ ID NO:4), and PpSCL3 (SEQ ID NO:6) protein sequences against the public NCBI database identified GRAS/SCR sequences from SwissProt (<e-40) as shown in Tables 1, 2 and 3. FIGS. 1, 2, and 3 show the relative homology and detailed alignment of PpSCL1, PpSCL2, PpSCL3 and GmSCL1 amino acid sequences (SEQ ID NO:2, 4, 6, and 8) with the sequences of six known members of the GRAS family.

Tissue Harvest, RNA Isolation, and cDNA Library Construction

Soybean plants were grown under a variety of conditions and treatments, and different tissues were harvested at various developmental stages. Plant growth and harvesting were done in a strategic manner such that the probability of harvesting all expressible genes in at least one or more of the resulting libraries is maximized. The mRNA was isolated as described in Example 3 from each of the collected samples, and cDNA libraries were constructed. No amplification steps were used in the library production process in order to minimize redundancy of genes within the sample and to retain expression information. All libraries were 3' generated from mRNA purified on oligo dT columns. Colonies from the transformation of the cDNA library into *E. coli* were randomly picked and placed into microtiter plates.

Probe Hybridization

Plasmid DNA was isolated from the *E. coli* colonies and then spotted on membranes. A battery of 288 $^{33}$P radiolabeled 7-mer oligonucleotides were sequentially hybridized to these membranes. To increase throughput, duplicate membranes were processed. After each hybridization, a blot image was captured during a phosphorimage scan to generate a hybridization profile for each oligonucleotide. This raw data image was automatically transferred via LIMS to a computer. Absolute identity was maintained by barcoding for the image cassette, filter, and orientation within the cassette. The filters were then treated using relatively mild conditions to strip the bound probes and returned to the hybridization chambers for another round of hybridization. The hybridization and imaging cycle was repeated until the set of 288 oligomers was completed.

After completion of the hybridizations, a profile was generated for each spot (representing a cDNA insert), as to which of the 288 $^{33}$P radiolabeled 7-mer oligonucleotides bound to that particular spot (cDNA insert), and to what degree. This profile is defined as the signature generated from that clone. Each clone's signature was compared with all other signatures generated from the same organism to identify clusters of related signatures. This process "sorts" all of the clones from an organism into clusters before sequencing.

The clones were sorted into various clusters based on their having identical or similar hybridization signatures. A cluster should be indicative of the expression of an individual gene or gene family. A by-product of this analysis is an expression profile for the abundance of each gene in a particular library. One-path sequencing from the 5' end was used to predict the function of the particular clones by similarity and motif searches in sequence databases.

The full-length DNA sequences of PpSCL1 (SEQ ID NO:1), PpSCL2 (SEQ ID NO:3), or PpSCL3 (SEQ ID NO:5) were blasted against proprietary contig BPS crop databases at E value of E-10. (Altschul, Stephen et al., Gapped BLAST and PSI_BLAST: a new generation of protein database search program, Nucleic Acids Res. 25:3389-3402). All the contig hits were analyzed for the putative full length sequences, and the longest clones representing the putative full length contigs were fully sequenced. One sequence, GmSCL1 (SEQ ID NO:7) from soybean was identified. The homology of the deduced amino acid sequence of GmSCL1 (SEQ ID NO:8) to the closest known prior art is indicated in Table 7. FIGS. 1, 2, and 3 show the relative homology and detailed alignment of PpSCL1 (SEQ ID NO:2), PpSCL2 (SEQ ID NO:4), PpSCL3 (SEQ ID NO:6), and GmSCL1 (SEQ ID NO:8) amino acid sequences with the sequences of other known members of the GRAS family.

TABLE 5

Degree of Amino Acid Identity and Similarity of GmSCL1 and a Similar Protein (Pairwise Comparison was used: gap penalty: 10; gap extension penalty: 0.1; score matrix: blosum62)

| Gene Name | Public Database Sequence | Protein Name | Species | Sequence Identity (%) | Sequence Similarity (%) |
| --- | --- | --- | --- | --- | --- |
| GmSCL1 | NP_200064 | Scarecrow-like transcription factor 8 | Arabidopsis thaliana | 44.7% | 57.5% |
| GmSCL1 | BAD27826 | Gibberellin-insensitive protein | Oryza sativa | 32% | 47% |
| GmSCL1 | NP_915059.1 | Scarecrow-like protein | Oryza sativa | 28% | 40% |
| GmSCL1 | AF036300_1 | Scarecrow-like 1 | Arabidopsis thaliana | 19% | 27% |

TABLE 6

Percent identity between amino acid sequences of GmSCL1, PpSCL1, PpSCL2 and PpSCL3 (SEQ ID NOs: 2, 4, 6, and 8)

|  | GmSCL1 | PpSCL1 | PpSCL2 | PpSCL3 |
| --- | --- | --- | --- | --- |
| GmSCL1 | 100 | 18 | 17 | 26 |
| PpSCL1 |  | 100 | 21 | 25 |
| PpSCL2 |  |  | 100 | 25 |
| PpSCL3 |  |  |  | 100 |

TABLE 7

Percent similarity between amino acid sequences of GmSCL1, PpSCL1, PpSCL2 and PpSCL3 (SEQ ID NOs: 2, 4, 6, and 8)

|  | GmSCL1 | PpSCL1 | PpSCL2 | PpSCL3 |
| --- | --- | --- | --- | --- |
| GmSCL1 | 100 | 29 | 29 | 41 |
| PpSCL1 |  | 100 | 32 | 38 |
| PpSCL2 |  |  | 100 | 37 |
| PpSCL3 |  |  |  | 100 |

Example 7

Engineering *Arabidopsis* Plants by Overexpressing PpSCL1, PpSCL2, PpSCL3, and GmSCL1 Genes Cloning of PpSCL1, PpSCL2, PpSCL3, or GmSCL1 Recombinant Vectors The fragments containing PpSCL1, PpSCL2, or PpSCL3 were subcloned from the recombinant PCR2.1 TOPO vector by double digestion with restriction enzymes (See Table 6) according to manufacturer's instructions. The subsequent fragments were excised from agarose gel with a QIAquick Gel Extraction Kit (Qiagen) according to manufacturer's instructions and ligated into the binary vector containing the selectable marker gene, the constitutive promoter and the terminator.

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*A. thaliana* ecotype C24 plants were grown and transformed according to standard conditions (Bechtold, 1993, Acad. Sci. Paris. 316:1194-1199; Bent et al., 1994, Science 265:1856-1860).

Screening of Transformed Plants

T1 plants were screened for resistance to the selection agent conferred by the selectable marker gene, and T1 seeds were collected. T1 seeds were sterilized according to standard protocols (Xiong et al., 1999, Plant Molecular Biology Reporter 17:159-170). Seeds were plated on ½ Murashige and Skoog media (MS) (Sigma-Aldrich) pH 5.7 with KOH, 0.6% agar and supplemented with 1% sucrose, 0.5 g/L 2-[N-Morpholino]ethansulfonic acid (MES) (Sigma-Aldrich), 50-150 µg/ml selection agent, 500 µg/ml carbenicillan (Sigma-Aldrich) and 2 µg/ml benomyl (Sigma-Aldrich). Seeds on plates were vernalized for four days at 4° C. The seeds were germinated in a climatic chamber at an air temperature of 22° C. and light intensity of 40 micromol $m^2s^{-1}$ (white light; Philips TL 65W/25 fluorescent tube) and 16 hours light and 8 hours dark day length cycle. Transformed seedlings were selected after 14 days and transferred to ½ MS media pH 5.7 with KOH 0.6% agar plates supplemented with 0.6% agar, 1% sucrose, 0.5 g/L MES (Sigma-Aldrich), and 2 µg/ml benomyl (Sigma-Aldrich) and allowed to recover for five to seven days.

Growth Screen Under Water-Limited Conditions

T1 plants were screened for resistance to the selection agent conferred by the selectable marker gene and seeds were collected. T2 and T3 seeds were screened for resistance to the selection agent conferred by the selectable marker gene on plates, and positive plants were transplanted into soil and grown in a growth chamber for 3 weeks. Soil moisture was maintained throughout this time at approximately 50% of the maximum water-holding capacity of soil.

The total water lost (transpiration) by the plant during this time was measured. After three weeks, the entire above-ground plant material was collected, dried at 65° C. for 2 days and weighed. The results are shown in Tables 8, 9, 10, and 11. The ratio of above-ground plant dry weight to plant water use is Water Use Efficiency (WUE). The Table 8 below shows mean WUE, standard error for WUE, plant dry weight (DW), and standard error for DW for PpSCL1 (SEQ ID NOs:1 and 2) overexpressing plants, wild-type controls, and transgenic vector-only controls. Data is from approximately 50 plants per genotype, 5 plants each of 10 independent transgenic lines, and 4 independent experiments.

TABLE 8

| Genotype | Assay | Mean WUE (g l⁻¹) | WUE Standard Error (g l⁻¹) | Mean DW (g) | DW Standard Error (g) |
|---|---|---|---|---|---|
| PpSCL1 (EST 386) | B | 2.19 | 0.09 | 0.218 | 0.007 |
| Wild-type control | B | 2.32 | 0.12 | 0.164 | 0.010 |
| Vector-only control | B | 2.19 | 0.08 | 0.193 | 0.006 |
| PpSCL1 (EST 386) | D | 2.21 | 0.08 | 0.117 | 0.004 |
| Wild-type control | D | 2.17 | 0.08 | 0.103 | 0.004 |
| Vector-only control | D | 1.90 | 0.06 | 0.072 | 0.003 |
| PpSCL1 (EST 386) | E | 1.70 | 0.08 | 0.097 | 0.007 |
| Wild-type control | E | 1.45 | 0.10 | 0.088 | 0.008 |
| Vector-only control | E | 1.53 | 0.05 | 0.098 | 0.005 |
| PpSCL1 (EST 386) | H | 1.76 | 0.04 | 0.102 | 0.003 |
| Wild-type control | H | 1.30 | 0.04 | 0.058 | 0.003 |
| Vector-only control | H | 1.55 | 0.03 | 0.088 | 0.003 |

The above data is summarized in Table 9 below by presenting the percent difference from vector-only and wild-type controls for the PpSCL1 (SEQ ID NO:2) overexpressing plants. The data show that PpSCL1 (SEQ ID NO:2) plants have a significant increase in DW and WUE, as compared to the controls. PpSCL1-overexpressing plants demonstrated an approximately 23-33% increase in dry weight as compared to the controls, and an approximately 10-12% increase in water use efficiency as compared to the controls.

TABLE 9

| Control | Assay | % difference from control | |
|---|---|---|---|
| | | WUE | DW |
| Vector-only control | B | 0 | +13 |
| | D | +16 | +63 |
| | E | +11 | −1 |
| | H | +14 | +17 |
| | mean | +10 | +23 |
| Wild-type control | B | −5 | +33 |
| | D | +2 | +13 |
| | E | +17 | +10 |
| | H | +35 | +76 |
| | mean | +12 | +33 |

Table 10 presents WUE and DW for independent transformation events (lines) for transgenic plants overexpressing PpSCL1 (SEQ ID NO:2) and PpSCL2 (SEQ ID NO:4). Least square means and standard errors of a line compared to wild-type controls from an Analysis of Variance are presented. The percent improvement from wild-type control plants for WUE and DW for PpSCL1 (EST 386) and PpSCL2 (EST 166) overexpressing plants are also presented.

TABLE 10

| Measurement | Genotype | Line | Least Square Mean | Standard Error | % Improvement |
|---|---|---|---|---|---|
| WUE | Wild-type | | 1.796 | 0.203 | |
| | PpSCL1 (EST 386) | 5 | 2.176 | 0.241 | 21 |
| DW | Wild-type | | 0.096 | 0.028 | |
| | PpSCL1 (EST 386) | 5 | 0.140 | 0.029 | 46 |
| WUE | Wild-type | | 1.650 | 0.170 | |
| | PpSCL2 (EST 166) | 4 | 1.840 | 0.191 | 12 |

TABLE 10-continued

| Measurement | Genotype | Line | Least Square Mean | Standard Error | % Improvement |
|---|---|---|---|---|---|
| DW | Wild-type | | 0.109 | 0.038 | |
| | PpSCL2 (EST 166) | 4 | 0.168 | 0.039 | 53 |

Table 11 represents WUE for independent transformation events (lines) for PpSCL3 (SEQ ID NO:6). Mean and standard errors of a line compared to transgenic controls are listed. In addition, an Analysis of Variance comparing all transgenic control lines with all PpSCL3 (SEQ ID NO:6) overexpressing lines for WUE is presented, showing least square means, standard errors and significance value (p). Improvement in mean in the combined analysis of PpSCL3 (SEQ ID NO:6) is also presented as percent stimulation, compared to the transgenic control.

TABLE 11

| Transgenic control Line | Least Square Mean | Standard error | PpSCL3 (EST512) Line | Least Square Mean | Standard error |
|---|---|---|---|---|---|
| 2 | 2.09 | 0.12 | 8 | 2.24 | 0.12 |
| 9 | 2.01 | 0.10 | 10 | 2.09 | 0.12 |
| 7 | 2.01 | 0.11 | 9 | 2.07 | 0.11 |
| 1 | 1.90 | 0.12 | 4 | 2.05 | 0.12 |
| 10 | 1.89 | 0.11 | 1 | 2.04 | 0.12 |
| 3 | 1.87 | 0.12 | 3 | 2.03 | 0 12 |
| 21 | 1.85 | 0.12 | 2 | 2.01 | 0.12 |
| 11 | 1.80 | 0.16 | 7 | 1.97 | 0.12 |
| 23 | 1.78 | 0.12 | 6 | 1.90 | 0.12 |
| 4 | 1.66 | 0.16 | 5 | 1.89 | 0.12 |

| Transgenic control | Least Square Mean | Standard error | EST512 | Least Square Mean | Standard error | % Stimulation | P |
|---|---|---|---|---|---|---|---|
| All Lines | 1.91 | 0.04 | All Lines | 2.03 | 0.04 | 6 | 0.037 |

Example 8

Engineering Stress-tolerant Corn Plants by Overexpressing SLSRP Genes

*Agrobacterium* cells harboring the genes and the maize ahas gene on the same plasmid were grown in YP medium supplemented with appropriate antibiotics for 1-3 days. A loop of *Agrobacterium* cells was collected and suspended in 2 ml M-LS-002 medium (LS-inf) and the tube containing *Agrobacterium* cells were kept on a shaker for 1-3 hrs at 1,200 rpm.

Corncobs [genotype J553x(HIIIAxA188)] were harvested at 7-12 days after pollination. The cobs were sterilized in 20% Clorox solution for 15 min followed by thorough rinse with sterile water. Immature embryos with size 0.8-2.0 mm were dissected into the tube containing *Agrobacterium* cells in LS-inf solution.

Agro-infection was carried out by keeping the tube horizontally in the laminar hood at room temperature for 30 min. Mixture of the agro infection was poured on to a plate containing the co-cultivation medium (M-LS-011). After the liquid agro-solution was piped out, the embryos were plated on the co-cultivation medium with schutellum side up and cultured in the dark at 22 C for 2-4 days.

Embryos were transferred to M-MS-101 medium without selection. 7-10 days later, embryos were transferred to M-LS- 401 medium containing 0.75 uM imazethapyr and grown for 4 weeks to select transformed callus cells.

Plant regeneration was initiated by transferring resistant calli to M-LS-504 medium supplemented with 0.75 μM imazethapyr and grown under light at 26° C. for two to three weeks. Regenerated shoots were then transferred to rooting box with M-MS-607 medium (0.5 μM imazethapyr).

Plantlets with roots were transferred to potting mixture and grown in a growth chamber for a week, then transplanted to larger pots and maintained in greenhouse till maturity.

---

We claim:

1. A transgenic plant transformed with a polynucleotide selected from the group consisting of:
   a) a polynucleotide sequence encoding a polypeptide comprising amino acids 1 to 657 of SEQ ID NO:6;
   b) a polynucleotide sequence comprising nucleotides 1 to 2281 of SEQ ID NO:5; and
   c) a polynucleotide sequence comprising nucleotides 218 to 2191 of SEQ ID NO:5;

wherein expression of the polynucleotide in the plant results in increased tolerance to drought stress, as compared to a wild type variety of the plant.

2. The transgenic plant of claim 1, wherein expression of the polynucleotide in the plant results in increased growth under water-limited conditions, as compared to a wild type variety of the plant.

3. The transgenic plant of claim 2, wherein the increased growth under water-limited conditions is due to the plant having increased Water Use Efficiency (WUE).

4. The transgenic plant of claim 3, wherein the increased WUE is due to the plant having increased dry weight.

5. The transgenic plant of claim 1, further defined as a monocot.

6. The transgenic plant of claim 1, further defined as a dicot.

7. The transgenic plant of claim 1, wherein the plant is selected from the group consisting of maize, wheat, rye, oat, triticale, rice, barley, soybean, peanut, cotton, rapeseed, canola, manihot, pepper, sunflower, tagetes, solanaceous plants, potato, tobacco, eggplant, tomato, Vicia species, pea, alfalfa, coffee, cacao, tea, Salix species, oil palm, coconut, perennial grass, wheatgrass, canarygrass, bromegrass, wild rye grass, bluegrass, orchardgrass, salfoin, birdsfoot trefoil, alsike clover, red clover, and sweet clover.

8. The transgenic plant of claim 7, which is maize.

9. The transgenic plant of claim 7, which is soybean.

10. The transgenic plant of claim 7, which is cotton.

11. The transgenic plant of claim 7, which is rapeseed or canola.

12. A transgenic seed which is true breeding for a polynucleotide selected from the group consisting of:
   a) a polynucleotide sequence encoding a polypeptide comprising amino acids 1 to 657 of SEQ ID NO:6;
   b) a polynucleotide sequence comprising nucleotides 1 to 2281 of SEQ ID NO:5; and
   c) a polynucleotide sequence comprising nucleotides 218 to 2191 of SEQ ID NO:5;

wherein a transgenic plant grown from said seed has increased tolerance to drought stress, as compared to a wild type variety of the plant.

13. The transgenic seed of claim 12, wherein the polynucleotide has the sequence encoding the polypeptide comprising amino acids 1 to 657 of SEQ ID NO:6.

14. The transgenic seed of claim 12, wherein the polynucleotide comprises nucleotides 1 to 2281 of SEQ ID NO:5.

15. The transgenic seed of claim 12, wherein the polynucleotide comprises nucleotides 218 to 2191 of SEQ ID NO:5.

16. An isolated polynucleotide selected from the group consisting of:
   a) a polynucleotide sequence encoding a polypeptide comprising amino acids 1 to 657 of SEQ ID NO:6;

b) a polynucleotide sequence comprising nucleotides 1 to 2281 of SEQ ID NO:5; and c) a polynucleotide sequence comprising nucleotides 218 to 2191 of SEQ ID NO:5.

17. A recombinant expression vector comprising a polynucleotide selected from the group consisting of:
   a) a polynucleotide sequence encoding a polypeptide comprising amino acids 1 to 657 of SEQ ID NO:6;
   b) a polynucleotide sequence comprising nucleotides 1 to 2281 of SEQ ID NO:5; and
   c) a polynucleotide sequence comprising nucleotides 218 to 2191 of SEQ ID NO:5.

18. A method of producing a drought-tolerant transgenic plant comprising the steps of:
   a) transforming a plant cell with an expression vector comprising a polynucleotide selected from the group consisting of:
      i) a polynucleotide sequence encoding a polypeptide comprising amino acids 1 to 657 of SEQ ID NO:6;
      ii) a polynucleotide sequence comprising nucleotides 1 to 2281 of SEQ ID NO:5; and
      iii) a polynucleotide sequence comprising nucleotides 218 to 2191 of SEQ ID NO:5; and
   b) generating a transgenic plant from the transformed plant cell, wherein the transgenic plant expressing the polynucleotide is drought tolerant.

* * * * *